United States Patent
Zhadkevich

(10) Patent No.: US 11,013,515 B2
(45) Date of Patent: May 25, 2021

(54) OCCLUDING CATHETER WITH AN OPTIONAL COMMON INFLATION AND GUIDEWARE CHANNEL AND METHOD OF USE

(71) Applicant: Michael Zhadkevich, Ninety Six, SC (US)

(72) Inventor: Michael Zhadkevich, Ninety Six, SC (US)

( * ) Notice: Subject to any disclaimer, the term of this patent is extended or adjusted under 35 U.S.C. 154(b) by 207 days.

(21) Appl. No.: 16/260,319

(22) Filed: Jan. 29, 2019

(65) Prior Publication Data

US 2019/0167271 A1 Jun. 6, 2019

Related U.S. Application Data

(60) Continuation-in-part of application No. 15/298,285, filed on Oct. 20, 2016, now Pat. No. 10,219,807, (Continued)

(51) Int. Cl.
  *A61B 17/12* (2006.01)
  *A61M 25/00* (2006.01)
  (Continued)

(52) U.S. Cl.
  CPC .... *A61B 17/12109* (2013.01); *A61B 17/1204* (2013.01); *A61B 17/12031* (2013.01);
  (Continued)

(58) Field of Classification Search
  CPC ...... A61M 25/10184; A61M 25/10187; A61B 17/12031; A61B 17/12036;
  (Continued)

(56) References Cited

U.S. PATENT DOCUMENTS

| | | | |
|---|---|---|---|
| 2,676,586 | A | 4/1954 | Coakwell, Jr. |
| 3,585,983 | A | 6/1971 | Kantrowitz |

(Continued)

FOREIGN PATENT DOCUMENTS

| | | |
|---|---|---|
| EP | 0 203 310 A2 | 3/1986 |
| EP | 1 891 902 A1 | 2/2008 |

(Continued)

OTHER PUBLICATIONS

European Patent Office; Extended European Search Report; European Application No. 14166170.2-1654; European Patent Office; pp. 1-7; publisher European Patent Office; Published Munich Germany; dated Jul. 28, 2014.

(Continued)

*Primary Examiner* — Tuan V Nguyen
(74) *Attorney, Agent, or Firm* — J. Bennett Mullinax, LLC

(57) ABSTRACT

An occluding catheter for preventing stroke by occluding blood flow to right and left carotid arteries is provided. The occluding catheter includes a shaft that has a proximal end and a distal end, and a proximal occluding balloon carried by the shaft. The proximal occluding balloon is inflated to occlude blood flow through one of the right carotid artery and the left carotid artery. A distal occluding balloon is carried by the shaft and is inflated to occlude blood flow through one of the right carotid artery and the left carotid artery that is not occluded by the proximal occluding balloon. The shaft has a segment that is located between the proximal occluding balloon and the distal occluding balloon. Also provided are alternative arrangements with a single or dual inflation and/or guidewire channel, single occluding balloon, and an associated method of diverting emboli from cerebral circulation.

14 Claims, 27 Drawing Sheets

Related U.S. Application Data which is a division of application No. 13/918,492, filed on Jun. 14, 2013, now Pat. No. 9,498,225.

(60) Provisional application No. 61/668,980, filed on Jul. 6, 2012, provisional application No. 62/651,210, filed on Apr. 1, 2018.

(51) Int. Cl.
  *A61M 25/10* (2013.01)
  *A61M 25/09* (2006.01)
  *A61B 17/22* (2006.01)

(52) U.S. Cl.
  CPC .. *A61B 17/12036* (2013.01); *A61B 17/12045* (2013.01); *A61B 17/12136* (2013.01); *A61M 25/09* (2013.01); *A61M 25/10* (2013.01); *A61M 25/1002* (2013.01); *A61M 25/1011* (2013.01); *A61M 25/10184* (2013.11); *A61B 2017/12127* (2013.01); *A61B 2017/22067* (2013.01); *A61M 25/1018* (2013.01); *A61M 2025/0003* (2013.01); *A61M 2025/1052* (2013.01); *A61M 2025/1063* (2013.01)

(58) Field of Classification Search
  CPC .......... A61B 17/12136; A61B 17/1204; A61B 17/12045; A61B 17/12109
  See application file for complete search history.

(56) References Cited

U.S. PATENT DOCUMENTS

| | | | |
|---|---|---|---|
| 3,587,584 A | | 6/1971 | Bourbon |
| 4,395,806 A | | 8/1983 | Wonder |
| 4,676,232 A | | 6/1987 | Olsson et al. |
| 4,745,924 A | | 5/1988 | Ruff |
| 4,813,934 A | * | 3/1989 | Engelson .......... A61M 25/0075 604/99.02 |
| 4,984,563 A | | 1/1991 | Renaud |
| 5,059,177 A | | 10/1991 | Towne |
| 5,271,409 A | | 12/1993 | Millay |
| 5,273,536 A | | 12/1993 | Savas |
| 5,360,403 A | | 11/1994 | Mische |
| 5,385,244 A | | 1/1995 | Kuing |
| 5,441,051 A | | 8/1995 | Hileman |
| 5,486,192 A | | 1/1996 | Walinsky |
| 5,514,079 A | | 5/1996 | Dilon |
| 5,662,671 A | | 9/1997 | Barbut |
| 5,741,295 A | | 4/1998 | McEwen |
| 5,766,151 A | * | 6/1998 | Valley ................ A61M 39/0247 604/103.07 |
| 5,817,001 A | | 10/1998 | Leschinsky |
| 5,908,407 A | * | 6/1999 | Frazee ................ A61M 25/1011 604/101.01 |
| 6,156,005 A | | 12/2000 | Theron |
| 6,168,579 B1 | | 1/2001 | Tsugita |
| 6,325,067 B1 | | 12/2001 | Sterman et al. |
| 6,425,916 B1 | | 7/2002 | Garrison et al. |
| 6,595,980 B1 | | 7/2003 | Barbut |
| 6,656,153 B1 | * | 12/2003 | Sakai ................ A61M 25/0075 604/164.13 |
| 7,250,025 B2 | | 7/2007 | Nigroni |
| 7,374,531 B1 | | 5/2008 | Kantrowitz |
| 7,458,980 B2 | | 12/2008 | Barbut |
| 7,727,254 B2 | | 6/2010 | Pab |
| 7,972,356 B2 | | 7/2011 | Boyle et al. |
| D643,536 S | | 8/2011 | Vivorizo |
| 7,998,104 B2 | | 8/2011 | Chang |
| 8,025,674 B2 | | 9/2011 | Barbut et al. |
| 8,034,043 B1 | | 10/2011 | Barbut |
| 8,061,562 B2 | | 11/2011 | Carpenter |
| 9,795,470 B2 | | 10/2017 | Ganesan |
| 2002/0072706 A1 | * | 6/2002 | Hiblar ................ A61M 25/0084 604/101.01 |
| 2002/0115982 A1 | | 8/2002 | Barbut |
| 2002/0173815 A1 | | 11/2002 | Hogendijk |
| 2003/0036728 A1 | | 2/2003 | Samson |
| 2003/0176884 A1 | | 9/2003 | Berrada |
| 2004/0193205 A1 | * | 9/2004 | Burgermeister .. A61M 25/0152 606/194 |
| 2005/0015048 A1 | | 1/2005 | Chiu |
| 2005/0038468 A1 | | 2/2005 | Panetta et al. |
| 2005/0059931 A1 | | 3/2005 | Garrison |
| 2005/0075531 A1 | | 4/2005 | Loeb et al. |
| 2005/0154344 A1 | | 7/2005 | Chang |
| 2005/0177130 A1 | * | 8/2005 | Konstantino ..... A61M 25/1038 604/509 |
| 2005/0197624 A1 | | 9/2005 | Goodson |
| 2006/0079740 A1 | | 4/2006 | Silver |
| 2006/0100639 A1 | | 5/2006 | Levin |
| 2008/0086081 A1 | * | 4/2008 | Eidenschink ..... A61M 25/1038 604/96.01 |
| 2009/0326575 A1 | | 12/2009 | Galdonik |
| 2010/0113939 A1 | | 5/2010 | Mashimo |
| 2010/0179583 A1 | | 7/2010 | Carpenter et al. |
| 2010/0222738 A1 | * | 9/2010 | Kassab ............. A61M 25/1011 604/99.04 |
| 2010/0324589 A1 | | 12/2010 | Carpenter et al. |
| 2011/0028934 A1 | | 2/2011 | Buckman et al. |
| 2011/0054322 A1 | | 3/2011 | Zanatta |
| 2011/0295114 A1 | | 12/2011 | Ahah et al. |
| 2011/0313445 A1 | | 12/2011 | Galdonik |
| 2012/0179195 A1 | | 7/2012 | Lashinski |
| 2012/0197194 A1 | * | 8/2012 | Osypka ............. A61M 25/104 604/103.07 |
| 2012/0203265 A1 | | 8/2012 | Heuser |
| 2013/0023909 A1 | | 1/2013 | Duhay |
| 2013/0184742 A1 | * | 7/2013 | Ganesan ................ A61F 2/01 606/200 |
| 2014/0012306 A1 | * | 1/2014 | Zhadkevich ..... A61B 17/12109 606/194 |
| 2014/0024955 A1 | | 1/2014 | Zhacikevich |
| 2014/0336690 A1 | | 11/2014 | Zhadkevich |

FOREIGN PATENT DOCUMENTS

| | | |
|---|---|---|
| EP | 2 260 776 A1 | 12/2010 |
| EP | 2 682 154 A1 | 1/2014 |
| WO | WO 98/47558 | 6/1996 |
| WO | WO 99/36028 | 7/1999 |
| WO | WO 00/32266 A1 | 6/2000 |
| WO | WO 01/13983 A2 | 3/2001 |
| WO | WO 2010/081025 A1 | 7/2010 |
| WO | WO 2011/017103 A2 | 2/2011 |
| WO | WO 2011/068946 A1 | 2/2011 |
| WO | WO 2012/083227 A1 | 6/2012 |

OTHER PUBLICATIONS

Wikipedia; "Pulmonary artery catheter Pulmonary artery catheter", Wikipedia, The Free Encyclopedia., May 12, 2012, XP055235920, Retrieved from the Internet:URLhttps://en.wikipedia.org/w/index.php?title=Pulmonary_artery_catheter&oldid+694424669 [retrieved on Feb. 18, 2017].

Joe Elbery; "Swan Ganz Physiology"; You Tube video retrieved from https://www.youtube.com/watch?v=7putxZN7jj4; Jan. 21, 2012; copyright 2012; published by Edwards Lifesciences, Irvine, California, USA.

Various Anonymous Authors; "Circle of Willis"; Wikipedia article retrieved from https://en.wikipedia.org/wiki/Circle_of_Willis; retrieved on Nov. 8, 2016; pp. 1-4; copyright 2016. Wikipedia Foundaton Inc.; San Francisco; California; USA.

European Patent Office; Extended European Search Report; European Application No. 13175517.5-1506; European Patent Office; pp. 1-10; publisher European Patent Office; Published Berlin Germany; dated Oct. 7, 2013.

United States Patent Office, Office Action; U.S. Appl. No. 15/333,076; United States Patent Office; pp. 1-15, publisher United States Patent Office; Published Alexandria, Virginia, USA; dated Sep. 5, 2018.

(56) References Cited

OTHER PUBLICATIONS

United States Patent Office, Office Action; U.S. Appl. No. 15/298,285; United States Patent Office; pp. 1-15, publisher United States Patent Office; Published Alexandria, Virginia, USA; dated May 3, 2018.

* cited by examiner

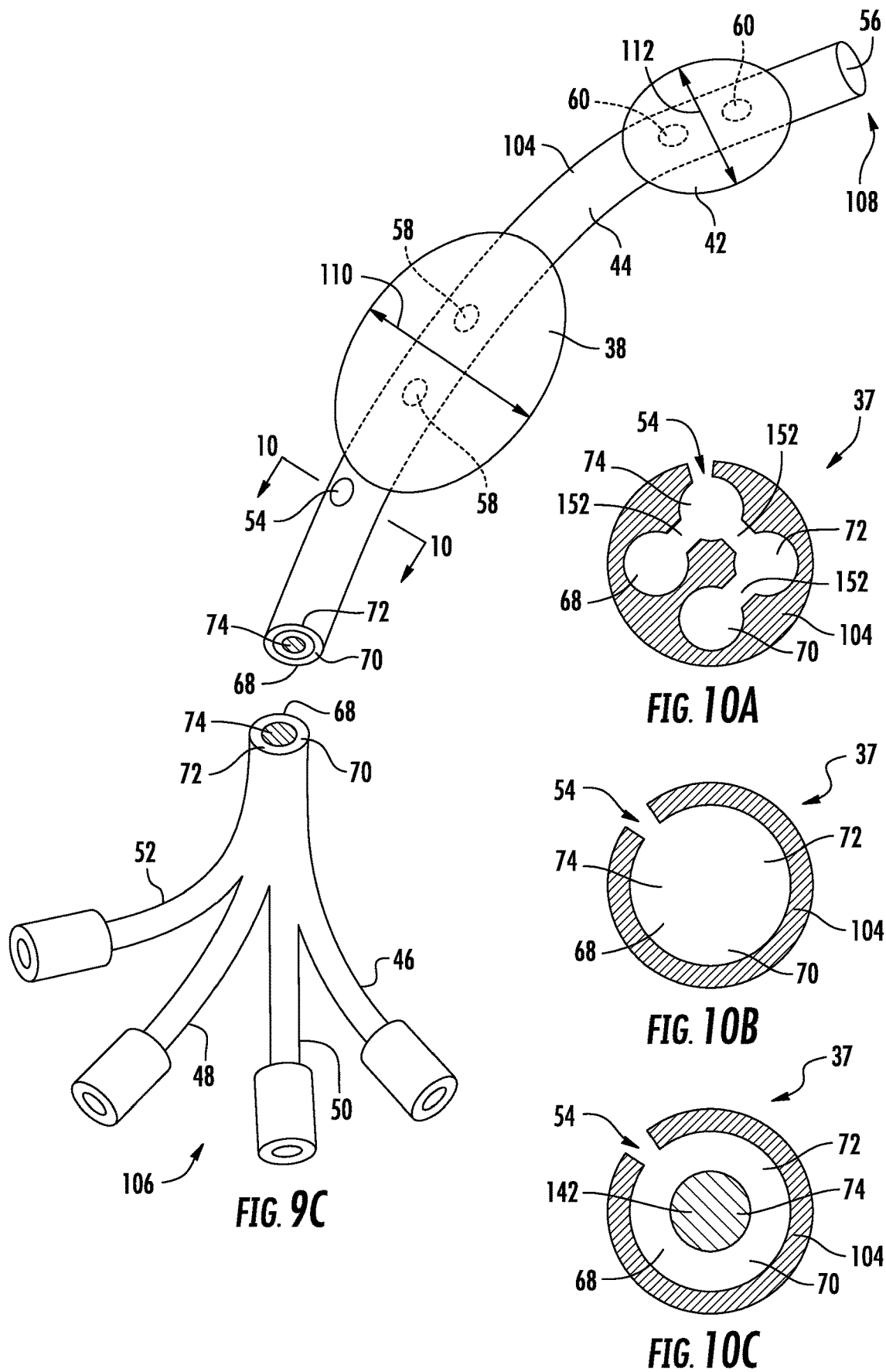

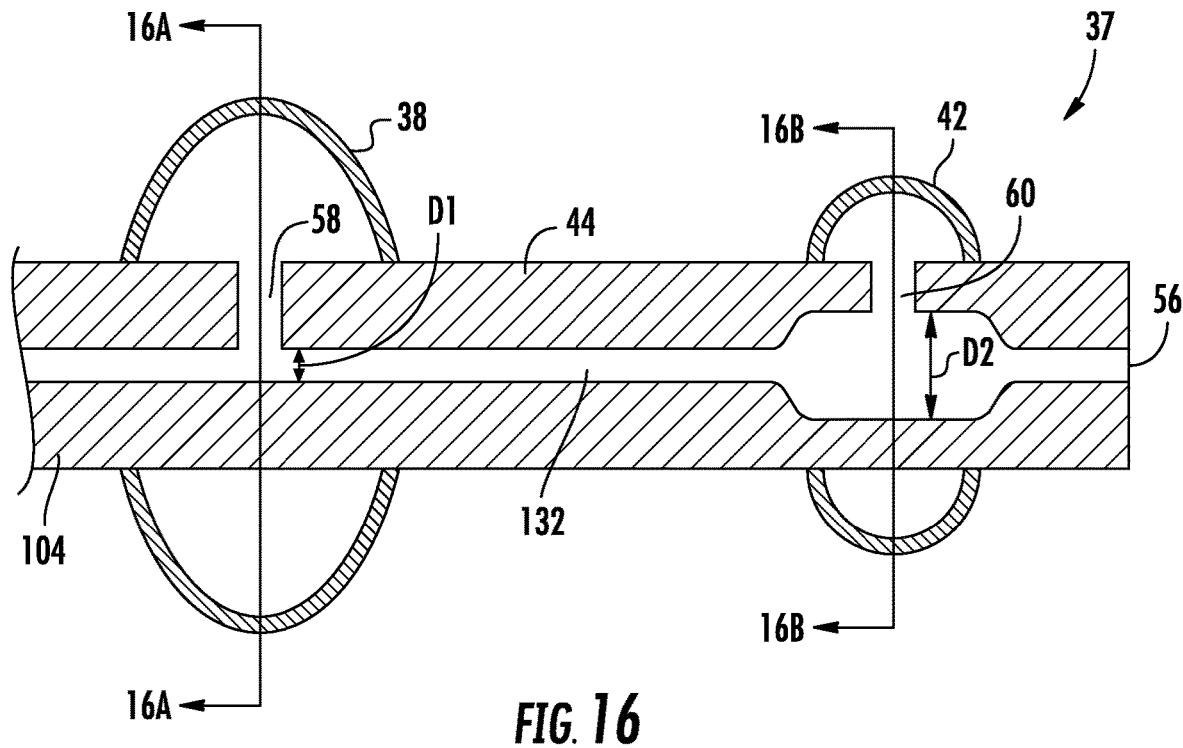
FIG. 16
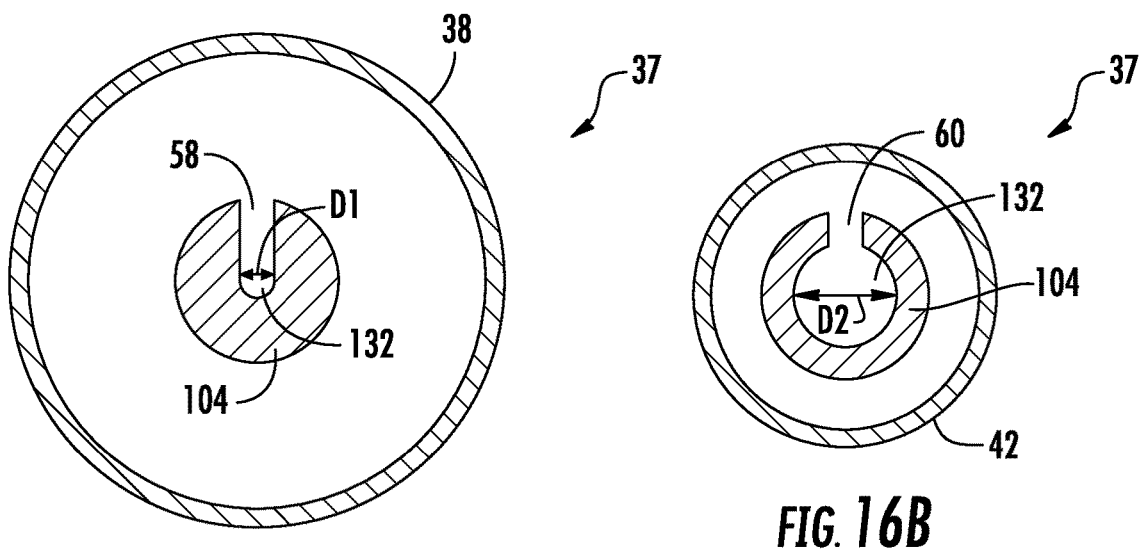
FIG. 16A
FIG. 16B

OCCLUDING CATHETER WITH AN OPTIONAL COMMON INFLATION AND GUIDEWARE CHANNEL AND METHOD OF USE

CROSS REFERENCE TO RELATED APPLICATIONS

The present application is a continuation-in-part application of and claims the benefit of U.S. application Ser. No. 15/298,285 filed on Oct. 20, 2016 and entitled "Occluding Catheter for Prevention of Stroke." U.S. application Ser. No. 15/298,285 is a divisional application of and claims the benefit of U.S. application Ser. No. 13/918,492 filed on Jun. 14, 2013 and entitled "Occluding Catheter and Method for Prevention of Stroke" that issued on Nov. 22, 2016 as U.S. Pat. No. 9,498,225. U.S. Ser. No. 13/918,492 is a non-provisional application and claims the benefit of U.S. Application Ser. No. 61/668,980 filed on Jul. 6, 2012 and entitled, "Device and method of prevention of embolic stroke." The present application is also a non-provisional application and claims the benefit of U.S. Application Ser. No. 62/651,210 filed Apr. 1, 2018 and entitled "Occluding Catheter with an Optional Common Inflation and Guidewire Channel and Method of Use." U.S. Application Ser. Nos. 62/651,210; 61/668,980; 13/918,492; 15/298,285 are incorporated by reference herein in their entireties for all purposes.

FIELD OF THE INVENTION

The present invention relates generally to devices and methods for deflection of emboli from cerebral arteries in order to prevent embolic stroke. More particularly, the present application involves a low profile occluding vascular catheter that may be inserted into the circulatory system of the patient through a vessel of a smaller caliber to occlude 2 vessels at the time of release of potential cerebral emboli and to prevent their entry into the brain through the carotid, subclavian and vertebral arteries during performance of procedures that may lead to formation of embolic particles leading to embolic stroke.

BACKGROUND

Intraoperative embolic stroke is one of the most dreadful complications of cardiac, aortic and vascular procedures, clinically diagnosed in 1-22% of patients undergoing cardiovascular surgery. Even more frequently, in up to 84% of cases, patients undergoing heart, valve, coronary artery bypass and aortic surgery experience subclinical embolic events as recorded by transcranial Doppler and MRI. Recent data showed an astounding incidence of stroke as detected by MRI in practically all groups of cardiac patients: in TAVR and Endovascular Thoracic Aortic Aneurysm surgery—84%, Aortic Valve Replacement—52%, emergent coronary intervention—49%, Balloon Aortic Valvuloplasty—40%, Cardiac Ablation 38% and Coronary Artery Bypass Surgery—20%. These embolic events lead to cognitive impairment and disability and have a significant impact on patients' recovery.

The main sources of cerebral emboli and stroke in this setting resides in the heart, heart valves, thoracic aorta, and great vessels when these structures are intervened thereon. Even simple cardiac catheterization with an endovascular catheter can induce trauma of the atherosclerotic thoracic aorta leading to formation of embolic particles with subsequent embolic brain injury ranging from latent ischemic foci to a massive or even fatal stroke.

Multiple devices are known that attempt to prevent embolization of the carotid arteries during endovascular and cardiac interventions. These anti-embolic devices, however, have not received wide acceptance in surgery of the heart, heart valves and thoracic aorta due to their complexity and invasive character with the risk of additional trauma to the inner vessel wall resulting in a high risk to benefit ratio. Known devices require insertion of additional hardware into the arterial system or aorta, a procedure that is known to be associated with all classical risks of endovascular intervention, including aortic dissection, bleeding, thrombosis, and carotid cerebral embolization and stroke. One known intra-aortic filter device that is inserted into the ascending portion of the thoracic aorta via an aortic cannula to capture potential embolic material released from the heart and aortic wall during heart surgery was found to be quite difficult to implement and was reported, to be associated with major trauma to aortic wall and acute aortic dissection.

Another such device for preventing emboli into the cerebral circulation includes a porous deflector/intra-aortic shield that captures or diverts potential emboli into the distal vascular. A yet additional device has also been proposed for use during aortic valve surgery and is an intra-aortic filter catheter that captures emboli during this procedure. It has been established that intravascular filters are not able to capture emboli smaller than the pore size of the available devices (currently 60-140 µm) resulting in cerebral microembolization. On the other hand, if the filter, pores are made smaller than 60-140 µm, then the flow of blood and blood elements become compromised leading to formation of microaggregates with clogging of filters and blocking the blood flow to the brain. Embolization may also occur due to poor apposition of the filter to the aortic or carotid arterial wall and or spillage of emboli during the filter closure and retrieval.

Furthermore, the placement of the filter by itself may produce cerebral emboli. For example, the mere passing of a guide wire into a carotid artery generates approximately 40,000 microemboli, with a significant percentage of small, less than 60 µm, particles that are not retained by standard filters. Therefore, in spite of multiple innovations in the field of anti-embolic devices, the problem of cerebral emboli and stroke during cardiovascular surgery is far from being resolved.

It is known to use balloon occlusion catheters for the prevention of embolic stroke. In this regard, the balloon occlusion catheter is placed inside of one of the carotid arteries when a procedure, for example carotid angioplasty and stenting, is conducted on the carotid artery in question. Although capable of preventing stroke when a single carotid artery is operated upon, this device cannot work to prevent stroke during procedures on the heart and aorta, endovascular or open, and cannot provide for bilateral occlusion. This device cannot simultaneously occlude the flow to both the left and right carotid arteries and/or subclavian arteries to prevent flow simultaneously through both of these arteries, and thus cannot prevent stroke should emboli flow into the non-blocked carotid artery.

Multiple cerebral protection devices used at the present time still have significant shortcomings, such as a significant size and large profile, precluding their safe insertion through the small peripheral artery, complex mechanism of actuation requiring an elaborate training and supervision, inability to actuate cerebral protection to multiple cerebral vessels simultaneously and difficulties with an access and catheterization of the left carotid artery, while using a radial artery approach. In case with the occluding catheters, such catheters tend to carry a large number of channels for inflation, perfusion and pressure measurement, thus contributing to the device complexity, larger size and higher profile, especially in the setting of a dual balloon configuration.

Additionally, the choice of occluding balloon material, shape, positioning and configuration have not been established to achieve the goal of a safe, effective, stable and technically feasible simultaneous occlusion of the innominate, carotid and/or subclavian arteries. Stable occlusion is defined as occlusion without the risk of balloon and/or catheter migration under the pressure of forward arterial flow. Blockade of flow to such arteries and/or vertebral arteries using a single shaft dual balloon catheter that achieves these various, goals may be desired. Therefore, there is room for variation and improvement within the art.

DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGS. in which:

FIG. 4-B is a font view of the patient of FIG. 1 that shows deflection of emboli with the proximal and distal occluding balloons having a configuration in which one portion of each balloon is wider than another portion.

FIG. 4-C is a front view of the patient of FIG. 1 that shows deflection of emboli with the proximal and distal occluding balloons being conical in shape.

FIG. 5-B is a front view of an occluding catheter in accordance with another alternative exemplary embodiment with an angled shaft, distal tip and points of fixation.

FIG. 5-C is a front view of an occluding catheter in accordance with yet another alternative exemplary embodiment comprising a unified pattern of internal channels and a balloon-dependent shaft-flexing mechanism.

FIG. 5-D is a front view of an occluding catheter of FIG. 5-C in accordance with an exemplary embodiment comprising an elongated proximal balloon and a balloon-dependent shaft-flexing mechanism in a monorail configuration.

FIG. 6-B is a cross-sectional view taken along, line 6-6 of FIG. 5-B.

FIG. 7-B is a cross-sectional view taken along line 7-7 of FIG. 5-B.

FIG. 8-B is a cross-sectional view taken along line 8-8 of FIG. 5-B

FIG. 6-C is a cross-sectional view taken along line 6-6 of FIG. 5-C.

FIG. 7-C is a cross-sectional view taken along line 7-7 of FIG. 5-C.

FIG. 8-C is a cross-sectional view taken along line 8-8 of FIG. 5-C.

FIG. 6-D is a cross-sectional view taken along line 6-6 of FIG. 5-D.

FIG. 7-D is a cross-sectional view taken along line 7-7 of FIG. 5-D.

FIG. 8-D is a cross-sectional view taken along line 8-8 of FIG. 5-D.

FIG. 9-B is a perspective view of the occluding catheter of FIG. 5-B in an inflated state with a section cut away to view interior portions.

FIG. 9-C is a perspective view of the occluding catheter of FIG. 5-C in an inflated state with a section cut away to view interior portions.

FIG. 10-A is a cross-sectioned view taken along line 10 of FIG. 9-A

FIG. 10-B is a cross-sectioned view taken along line 10 of FIG. 9-B.

FIG. 10-C is a cross-sectioned view taken along line 10 of FIG. 9-C.

FIG. 14-B is a front view of the patient with the occluding catheter in accordance with another exemplary embodiment.

FIG. 16 is a cross-sectional view of a portion of the catheter that has a channel of different diameters associated with different occluding balloons.

FIG. 16A is a cross-section along line 16A-16A of FIG. 16.

FIG. 16B is a cross-section along line 168-16B of FIG. 16.

Figure 1:
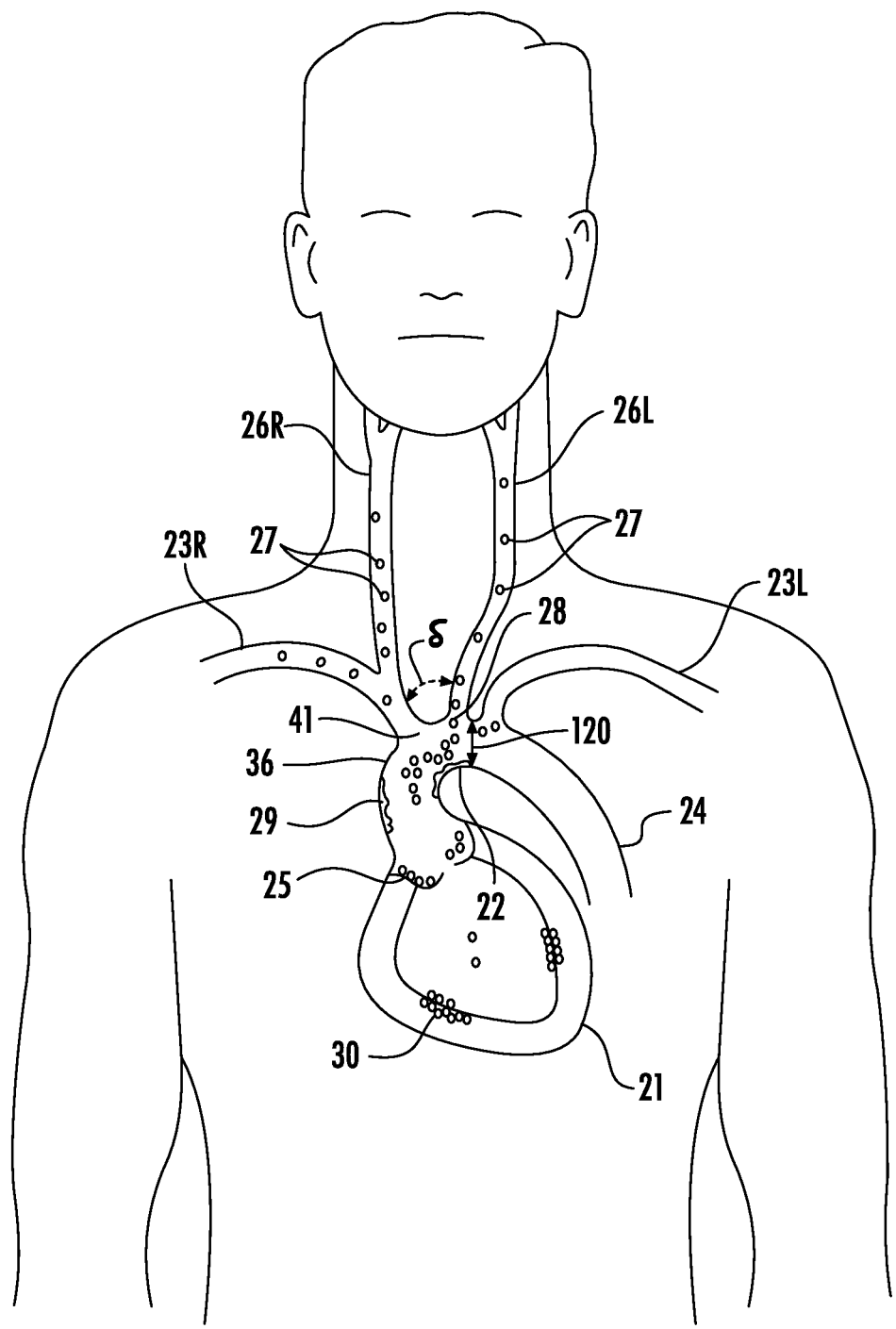
FIG. 1 is a front view of a patient with emboli in the heart and ascending thoracic aorta with subsequent propagation of emboli into both carotid arteries with the source of emboli being diseased aorta, aortic valve and the heart.

Repeat use of reference characters in the present specification and drawings is intended to represent the same or analogous features or elements of the invention.

DETAILED DESCRIPTION OF REPRESENTATIVE EMBODIMENTS

A recent development of an occluding balloon catheter for intraoperative cerebral protection by the author of this invention prompted further refinement of a double balloon or a single balloon vascular occluding catheter with the main goal to decrease its potential profile, to improve its efficacy and to simplify its use and design.

To achieve this goal one must create an occluding catheter with a lowest 5» possible profile, suitable for insertion into a small artery such as a radial, brachial or an ulnar artery, and having the most appropriate shape and curvature for an effortless access and catheterization of the subclavian, innominate and carotid arteries and other cerebral vessels. In addition it would require a system for simultaneous actuation and de-actuation of the occluding balloons achieved within a minimal amount of time, being able to provide an instantaneous response to the medical demands comprising detection and immediate deflection of embolic particles.

Further advancement in the catheter design and profile, would be minimizing the number of the catheter channels and creating a unified and synchronized mechanism of the balloon actuation, capable to achieve a prompt synchronous occlusion of the flow to the right and left carotid arteries, vertebral and/or subclavian arteries at any point of time in the course of cardiovascular procedure on demand, whether it is recommended and activated by the physician, or as a response to triggering signals, signifying an increased risk of cerebral embolization. Another important feature of such a mechanism would be a possibility to inflate and deflate both balloons much faster, using, if desired, a single injection and aspiration port and a single inflation-deflation source, ranging from a single-hand inflation by a medical professional to an automated inflation-deflation system actuated and synchronized with different physiological parameters and events, such as detection of embolic particles in the bloodstream, phase of surgery and/or cardiac cycle, and alterations of the parameters of the cerebral flow and the whole body perfusion. To achieve a timed, expeditious and most effective inflation and deflation of the occluding balloons, it would be desirable to make the processes of the balloon deflation and inflation—active, and, if needed, automated processes with active mechanical aspiration of the balloon contents (air, gas or fluid) leading to the fastest possible deflation of the balloon and reconstitution of the blood flow through the occluded artery.

In addition, such an arrangement would solve a problem of achieving a required degree of inflation with the balloon enlargement to an adequate size in order to achieve a desired degree of occlusion of a target artery, such as innominate, subclavian and/or carotid artery with a minimal or no trauma to the vessel and, a minimal amount of time required for inflation and deflation of occluding balloons. These goals can be achieved by creating a common inflation channel and assuring a fluid continuity of their lumens with each other and/or with the catheter channel designated for a guidewire 142, thus allowing using the same channel space for different purposes such as inflation, deflation, pressure measurements, blood sampling and/or insertion of a guidewire 142.

The degree of distention and completeness of occlusion (partial vs. full) of the target artery may be influenced by the degree of the balloon distention in the setting of a specific range and/or ratios of the balloon volumes, their shapes, configurations, positioning in relation to the specific shapes and configuration of the ostia of the aortic arch branches. Additionally, diameters, sizes and the degrees of compliance of the materials representing the distal vs. the proximal balloon can effect the degree of distention and the completeness of occlusion, with an optimal ratio of the proximal vs. distal balloon diameters being equal or approximate to the respective ratio of the diameters of the innominate and left carotid arteries as determined by CT or MRI scan, CT or MRI angiography, arteriography, ultrasound or a direct catheter intervention.

Reference will now be made in detail to embodiments of the invention, one or more examples of which are illustrated in the drawings 2-15. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for an occluding catheter 37 that may be introduced into the circulatory system of a patient in order to prevent emboli from entering the carotid arteries 26R, 26L and causing stroke. The occluding catheter 37 may be arranged so that has a pair of occluding balloons 38 and 42, OF one, three or more occluding balloons in accordance with different exemplary embodiments. The occluding catheter 37 can be positioned within the circulatory system in, a deflated state. When needed, the occluding catheter 37 can be inflated in order to block blood flow to the carotid arteries 26R, 26L and/or subclavian arteries 23R, 23L and hence prevent emboli 28 from flowing to the carotid arteries 26R, 26L, vertebral arteries coming off subclavian arteries 26R, 26L and into cerebral circulation. The occluding catheter 37 can be equipped with the capability of employing a guide wire 100 and/or pressure wire 74 (FIG. 10-A) with the ability to measure pressure at different levels of the catheter, upstream and downstream in one or more arteries of the patient to ensure proper blockage and to obtain blood sampling, if necessary. If needed or desired, flow may be blocked to both vertebral arteries by blocking flow to subclavian arteries 23R and 23L.

Figure 4A:
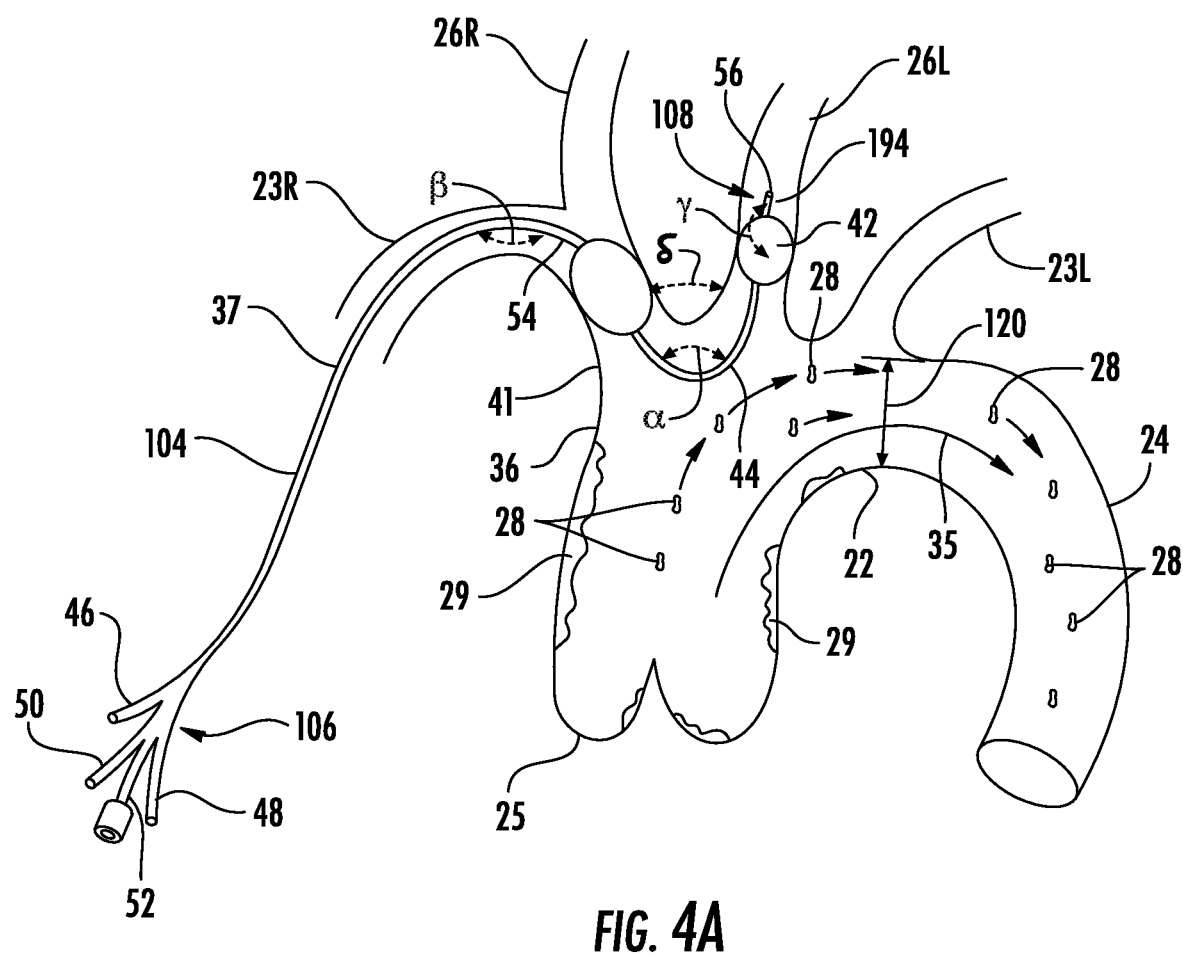
FIG. 4-A is a front view of the patient of FIG. 1 that shows the deflection of emboli into descending aorta, preventing their entry into carotid arteries when the occluding balloons are inflated.
Figure 4B:
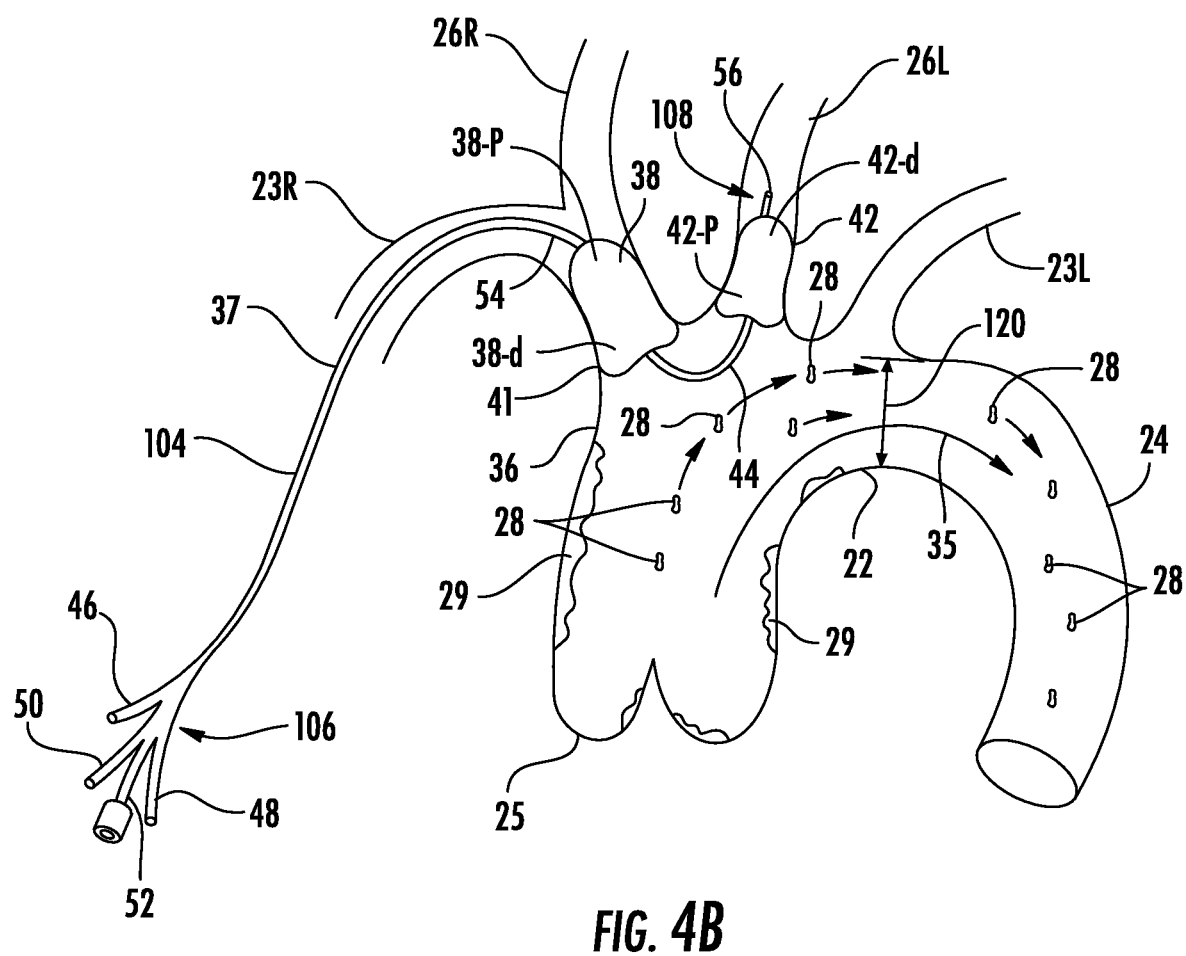

In some embodiments the occluding balloons 38, 42 may be designed in such a way that their actuation (distention) would lead to their better stabilization within the lumen of the ostium of the corresponding aortic arch branch or branches (such as Innominate, carotid 26R, 26L and/or subclavian arteries 23R, 23L) preventing the balloon 38, 42 and catheter migration into the more distal arterial segments under the pressure of the aortic arterial inflow into these branches (FIG. 4-B). This goal may be achieved by (1) using a combination of occluding balloon, where the proximal segment 42-*p* of a distal balloon 42 is wider and/or more compliant than the rest of said balloon 42, while a distal portion 38-*d* of a proximal balloon 38 is wider and/or more compliant than the part 38-*p* and/or the rest of a said balloon 38; (2) Using a highly compliant balloon material that would congruently "comply" to the inner shape of the ostia of the innominate, carotid 26R, 26L and/or subclavian arteries 23R, 23L upon their distention. This can be accomplished without leading to undue distention and/or rupture of underlying arteries by virtue of the compliance of the balloon material which would be protective of the integrity of the arterial vessel wall. (3) Using a conal shape of the occluding balloons in a disclosed specific configuration where the narrow portion 42-*n* of the cone of the distal balloon 42 is turned towards the distal end of the catheter 37, while the narrow portion of the cone 38-*n* of the proximal balloon 38 is turned towards the more proximal End of the catheter 37.

Figure 14A:
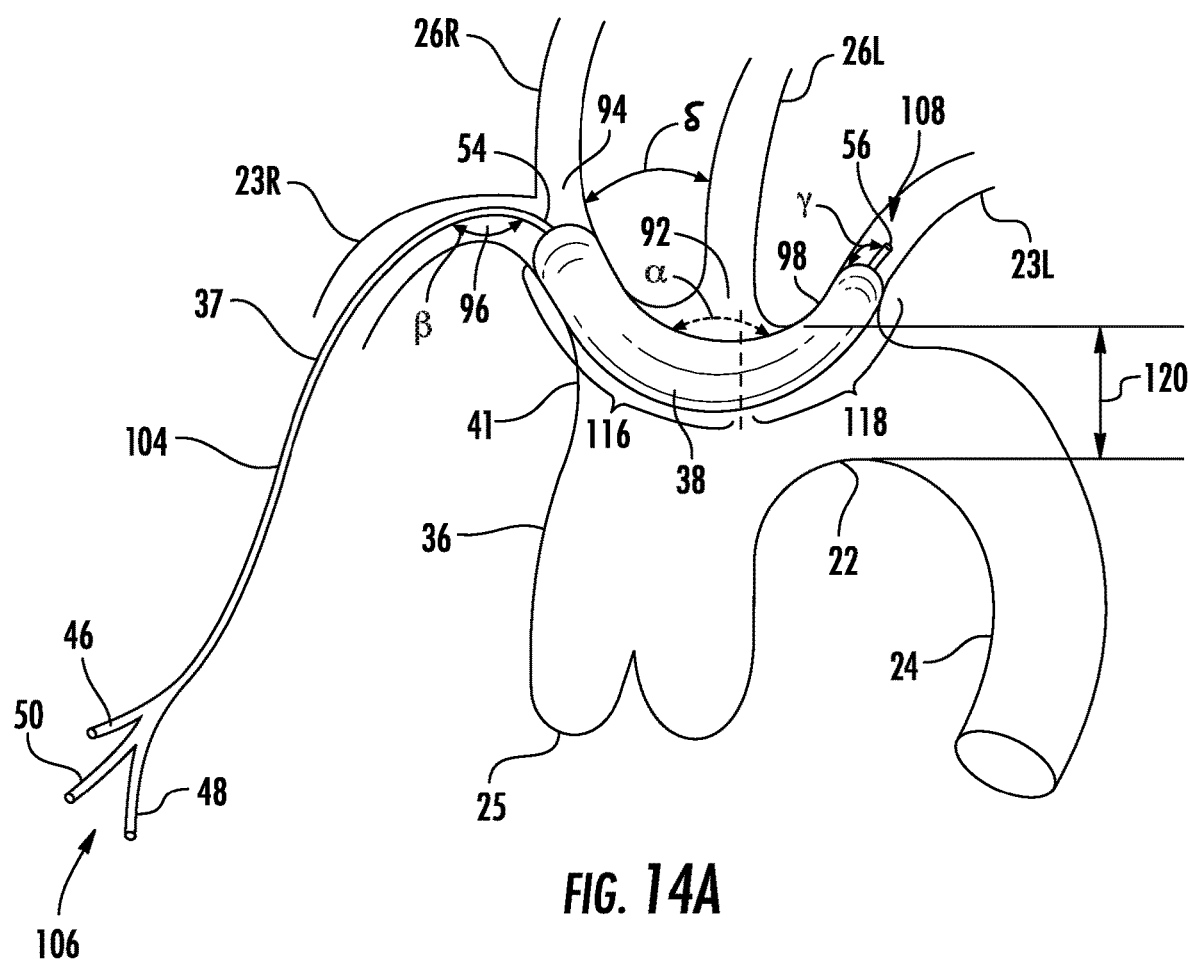
FIG. 14-A is a front view of the patient with the occluding catheter of FIG. 13 in an inflated state.
Figure 14B:
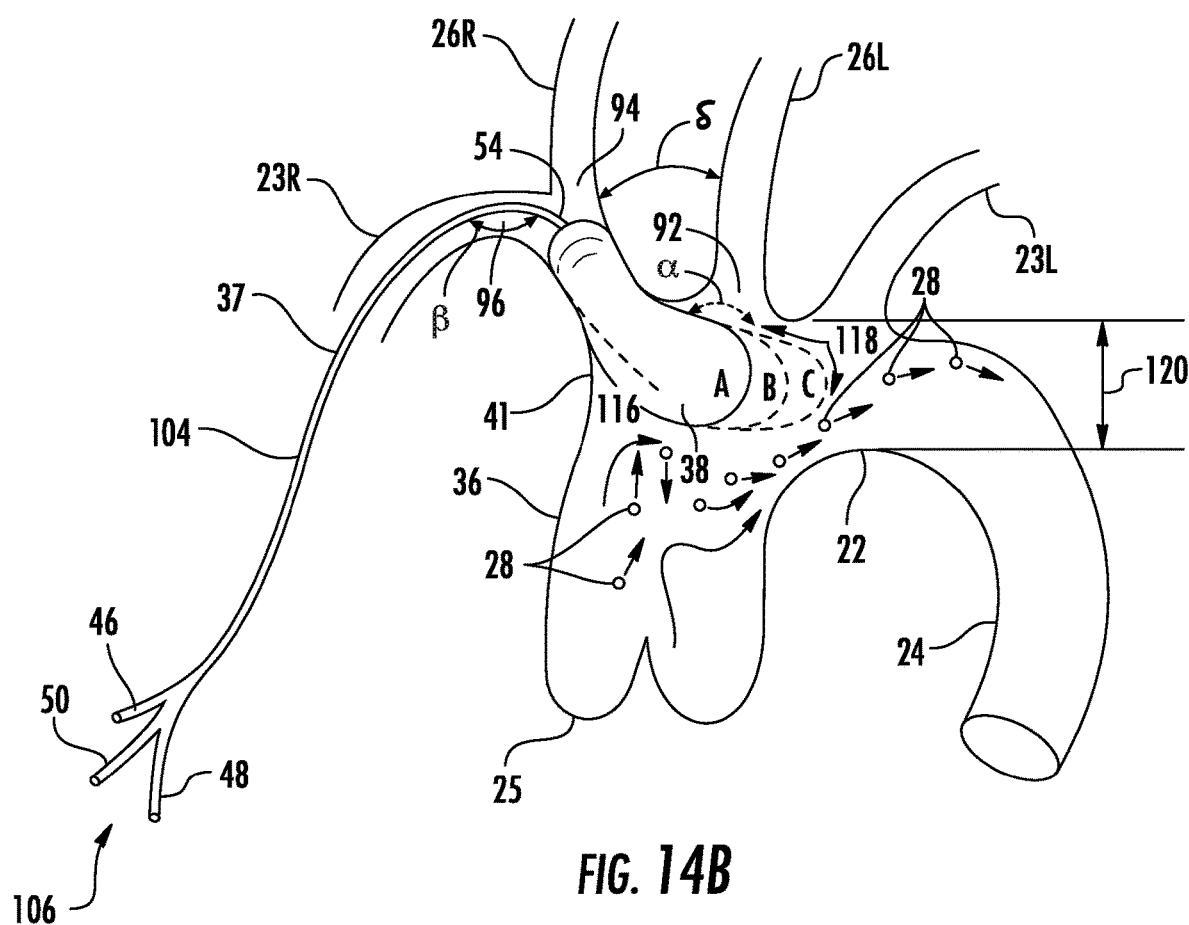

In addition, the occluding catheter, whether it is having a one or two balloon configuration, may have an embodiment, wherein just a proximal balloon 38 may protect both the innominate and left carotid and/or left subclavian arteries with or without having a distal balloon 42 and without direct occlusion or contact of the arteries 26L and/or 23L. In this embodiment (FIG. 14-B) a distal portion 118 of a proximal occluding balloon 38 may have a diameter that is at least 50% larger than a diameter of a proximal portion 116 of a proximal balloon 38 and at least 30% smaller than a diameter of the aortic arch 120, when inflated, wherein a distal portion 118 of a proximal occluding balloon 38, when inflated is located inside the aortic arch and/or is bulging into the lumen of the aortic arch, creating at least partial overlap of the ostium 92 of the left carotid artery 26L and/or at least partial barrier to the aortic flow towards the arteries 41, 26 and/or 23L and deflecting the emboli away from the innominate artery 41, left carotid artery 26L and/or left subclavian arteries 23L without occluding the left carotid and left subclavian arteries directly and without contacting the arterial walls of arteries 26L and 23L, by virtue of shielding said arteries from propagation of embolic particles 28 and preventing the embolic particles 28 from entering the orifices of the left carotid 26L and/or left subclavian 23L arteries by creating at least a partial barrier to the blood flow and hence the emboli 28 on the outer curvature of the aortic arch, that is bearing the ostia of arteries 41, 26L and 23L (FIG. 14-B). In some embodiments a similar result may be achieved by leaving a distal portion 118 of a proximal occluding balloon 38 inside the lumen of the aortic arch and keeping the proximal portion 116 of a balloon 38 inside an innominate artery. In this embodiment, especially if the balloon 38 is made out of a very compliant material and/or the distal portion 118 of balloon 38 is made of a material that is more compliant than its proximal portion 116, the inflation of such a balloon will lead to a more significant expansion of a distal portion of a balloon 38 inside the aortic arch (FIG. 14-B), leading to shielding of the orifice 92 of the left carotid 26L and/or orifice of a left subclavian 23L arteries from emboli 28 without their balloon occlusion. This result is obtained by virtue of creating a "flow-shadow" and "anti-embolic shadow" over ostia of a left carotid and/or left subclavian arteries on the path of emboli 28 released from the heart, aortic valve 25 and ascending aorta 36 towards the aortic arch branches 41, 26L and/or 23L (FIG. 14-B) where the emboli 28 would bounce off the hydraulic barrier created by the distal portion of the balloon 38 and will be deflected away from aortic arch branches 41, 26L and 23L towards the descending aorta 24 (as shown by arrows indicating the flow in the aorta and aortic arch on FIG. 14-B). The angle Alpha may be created in the medium-distal portion of a proximal balloon 38 ranging from 15 to 75 degrees thus assuring even more complete shielding of the orifice 92 of the left carotid artery 26L and/or artery 23L. The degree of expansion of the distal portion 118 of a proximal balloon 38 may vary from A to B to C and, may depend to the degree of compliance of the distal portion 118 of a balloon 38 in relation to its proximal portion as well—on the degree of balloon inflation (FIG. 14-B). In some embodiments the distal portion 118 of balloon 38 may not be inflated at all and, if made out of a floppy compliant material, may create a protective veil over the orifice 92 of the left carotid artery 26L and or left subclavian artery 23L, preventing emboli 28 from entering arteries 23L, 26L and/or 41. Such a veil may have an unfolding and recoil folding capacity and be expanded over the ostia of aortic branches 41, 26L and 23L with every cardiac contraction and ejection (systole) with an option of collapsing back to its folded position with each cardiac relaxation (diastole), thus creating hemodynamic conditions, preventing the entry of emboli into the arteries 41, 23*l* and 26L. In some embodiments such a veil may be made without a balloon at all and can be represented with a collapsible, expandable and/or unfolding or unrolling mesh carrying pores of variable configuration and size as we previously described in our previous art (ZHA-2-CIP)

An associated method for preventing emboli 28 from entering cerebral circulation is also provided.

With reference to FIG. 1, a front view of a patient is shown in which emboli 28 are transferred from the aortic arch 22 into the carotid arteries 26R, 26L. The emboli 27 that are present in the carotid arteries 26R, 26L can then be transferred into the cerebral circulation causing stroke of the patient. The emboli 27 may be fragments of atherosclerotic plaque 29 of the ascending aorta 36 that become dislodged during manipulation of the ascending thoracic aorta 36. Also shown in FIG. 1 is calcification of the aortic valve 25 and intracardiac emboli 30 of the heart 21 that can also be the origin of emboli 27 eventually present in the carotid arteries 26R, 26L. The intracardiac emboli 30 may include air, gas, thrombi, atherosclerotic and foreign body materials. Although all of the various emboli in the heart 21, aortic arch 22, ascending aorta 36, and, aortic valve 25 need not be present in all instances, they are all shown in FIG. 1 for sake of example. Trauma to the heart 21, aortic valve 25 and aortic structures during placement and removal of items such as aortic clamps, electrophysiological and other instruments, along with manipulations such as coronary artery bypass grafting, aortic and mitral valve replacement, catheter ablation, endovascular grafting of the aorta 22, balloon valvuloplasty, percutaneous implantation of the aortic or mitral valves, endovascular manipulations on the aorta 22, aortic branches and the heart 21 may give rise to the presence of emboli 27 in the carotid arteries 26R, 26L. Critical moments of the aforementioned procedures (for example during the aortic cross clamp manipulation, percutaneous aortic and mitral valvuloplasty or valve implantation, coronary interventions, endovascular grafting of the aorta 22 and its branches, and endovascular procedures on the aorta 22) may cause emboli 27 to form and cause stroke and are referred to as "emboligenic" events.

Figure 2:
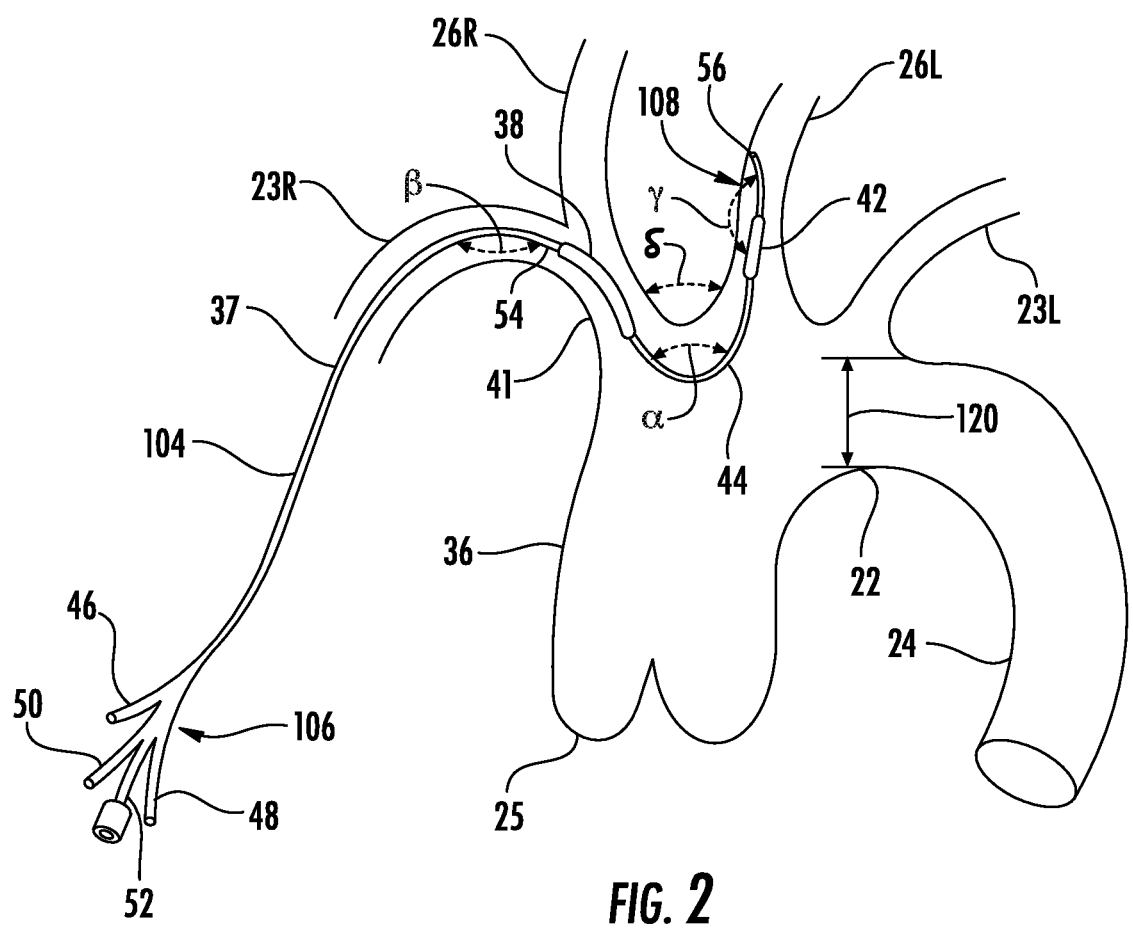
FIG. 2 is a front view of the patient with an occluding catheter in a deflated state positioned within the circulatory system of the patient.

FIG. 2 discloses an occluding catheter 37 positioned within the circulatory system of the patient. The occluding catheter 37 is introduced through the right radial artery and then advanced via the right subclavian artery 23R and has a shaft 104 with a proximal end 106 located outside of the patient, and a distal end 108 positioned within the left carotid artery 26L or left subclavian artery 23L. The occluding catheter 37 has a proximal occluding balloon 38 located closer to the health care provider and thus closer to the proximal end 106 than a distal occluding balloon 42 which is farther away from the health care provider and thus closer to the distal end 108. The proximal occluding balloon 38 may be located at least partially within an innominate artery 41 of the patient. The occluding catheter 37 can be arranged as shown in FIG. 2 so that no portion of it is located within the right carotid artery 26R. In other exemplary embodiments, some portion of the occluding catheter 37 may be located at the ostium or within the right carotid artery 26R. A segment 44 of the shaft 104 that is located between the proximal and distal occluding balloons 38, 42 may be located in the aortic arch 22, or may be partially or completely replaced by occluding balloon 38, 42 or a third intermediate balloon of a shape congruent to the inner surface of the aortic arch in the area of a take-off of the aortic arch branches and configured to cover at least one of their ostia (such as the ostium of the left carotid artery, when, the distal balloon 42 is positioned within the left subclavian artery), The occluding catheter 37 may be inserted into the right subclavian artery 23R via right radial, brachial, axillary or subclavian artery approach and can be advanced under fluoroscopic and arterial blood pressure guidance into the innominate artery 41, aortic arch 22 and finally into the left carotid artery 26L or left subclavian artery 23L. The ideal position of the distal occluding balloon 42 may be in the proximal segment of the left carotid artery 26L or left subclavian artery 23L, whereas the proximal occluding balloon 38 may be located at any level of the innominate artery 41 and the intermediate third balloon (at segment 44)—at the level of the take-off of the left carotid artery covering its ostium.

The insertion of the occluding catheter 37 may be performed when both the proximal 38 and distal 42 occluding balloons are deflated. However, once the distal occluding balloon 42 reaches the level of the aortic arch 22 it can be at least partially inflated to facilitate its advancement into the left carotid artery 26L and/or left subclavian artery 23L. In some embodiments it is possible to partially inflate the distal balloon without inducing significant distention of the proximal balloon due to an option of a more compliant material of a distal balloon compared to its proximal counterpart. Small amount of gas or fluid (0.5-3.5 cc or more) in this setting would allow achievement of a more substantial expansion of the balloon made out of a more compliant material, or having a larger volume, whereas both balloons may be in fluid communication with each other. The inflated distal occluding balloon 42 may be naturally propelled forward into the left carotid artery 26L and/or left subclavian artery 23L by arterial blood flow while facilitated by virtue of disclosed distal floating tip of the catheter and/or balloon with or without a guidewire 142, and also due to combination of specific curvatures Alpha ($\alpha$) Beta ($\beta$) and Gamma ($\gamma$), radiuses ($R_1$, $R_2$) shapes and points of fixation ($\alpha$, $\beta$, $\gamma$) of the distal, middle and other segments of the catheter (FIGS. 2, 3, 4, 5A, 5-B, 5-C). The adequacy of the position of a distal occluding balloon 42 is confirmed with fluoroscopy, ultrasound (with an optional ultrasound probe imbedded into the catheter shaft) and, if desired, by appearance of the dampened arterial pressure recorded from the end of a guidewire 142 channel and/or pressure measurement channel 70 that through the end pressure measurement port 50 with its distal tip opening 56 or and a guidewire 142 or a pressure wire 102 located distal from the tip of the distal occluding balloon 42 downstream from the area of occlusion of the left carotid artery 26L or left subclavian artery 23L, or proximal and downstream to the proximal end of the balloon 38—downstream from the points of occlusion of the innominate artery 41, right carotid artery 26R and right subclavian artery 23R.

Once an adequate position of the distal occluding balloon 42 in the left carotid artery 26L is achieved it may be deflated. A normal arterial blood pressure waveform as recorded from the distal tip opening 56 or a pressure wire 102 should reappear to confirm adequate perfusion via the left carotid artery 26L.

Figure 3:
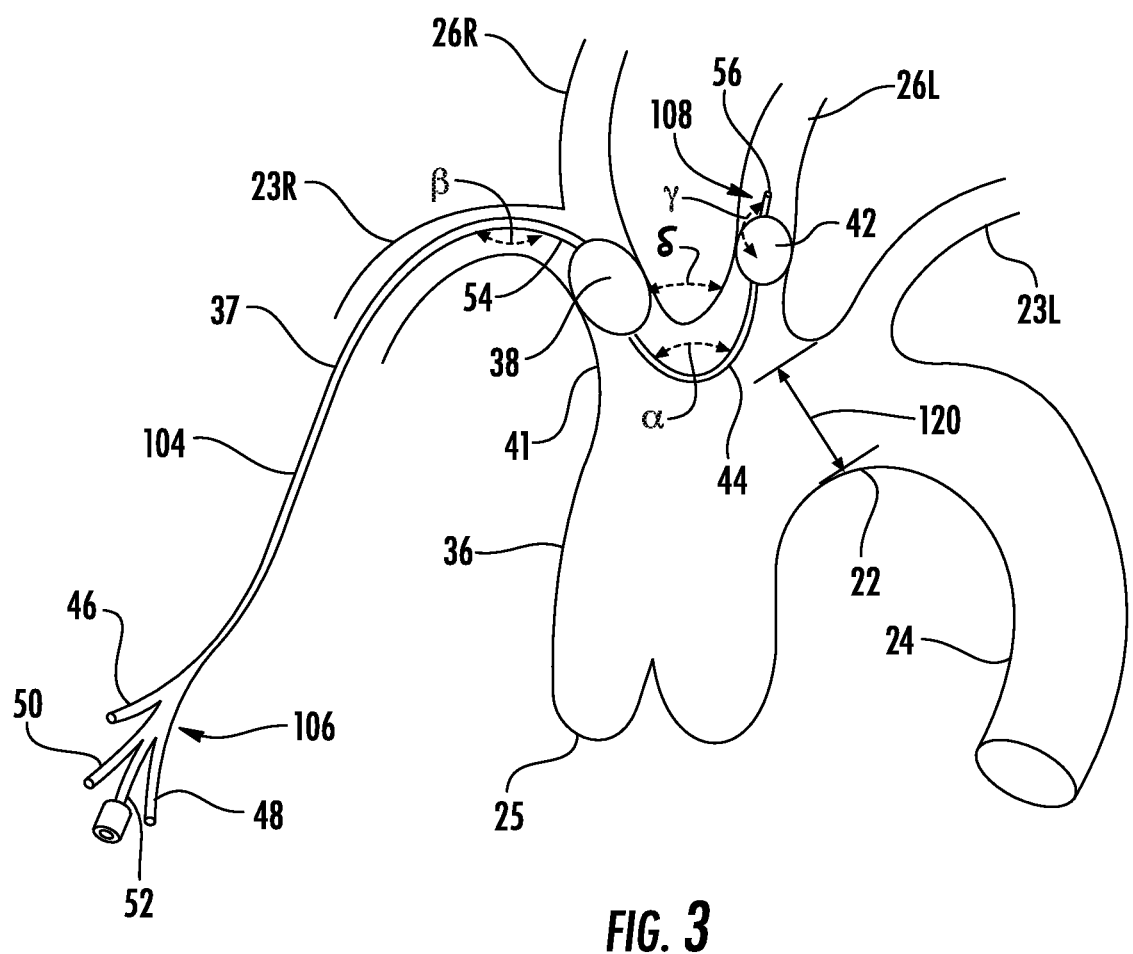
FIG. 3 is a front view of the patient of FIG. 2 with the occluding catheter in an inflated state.
Figure 12:
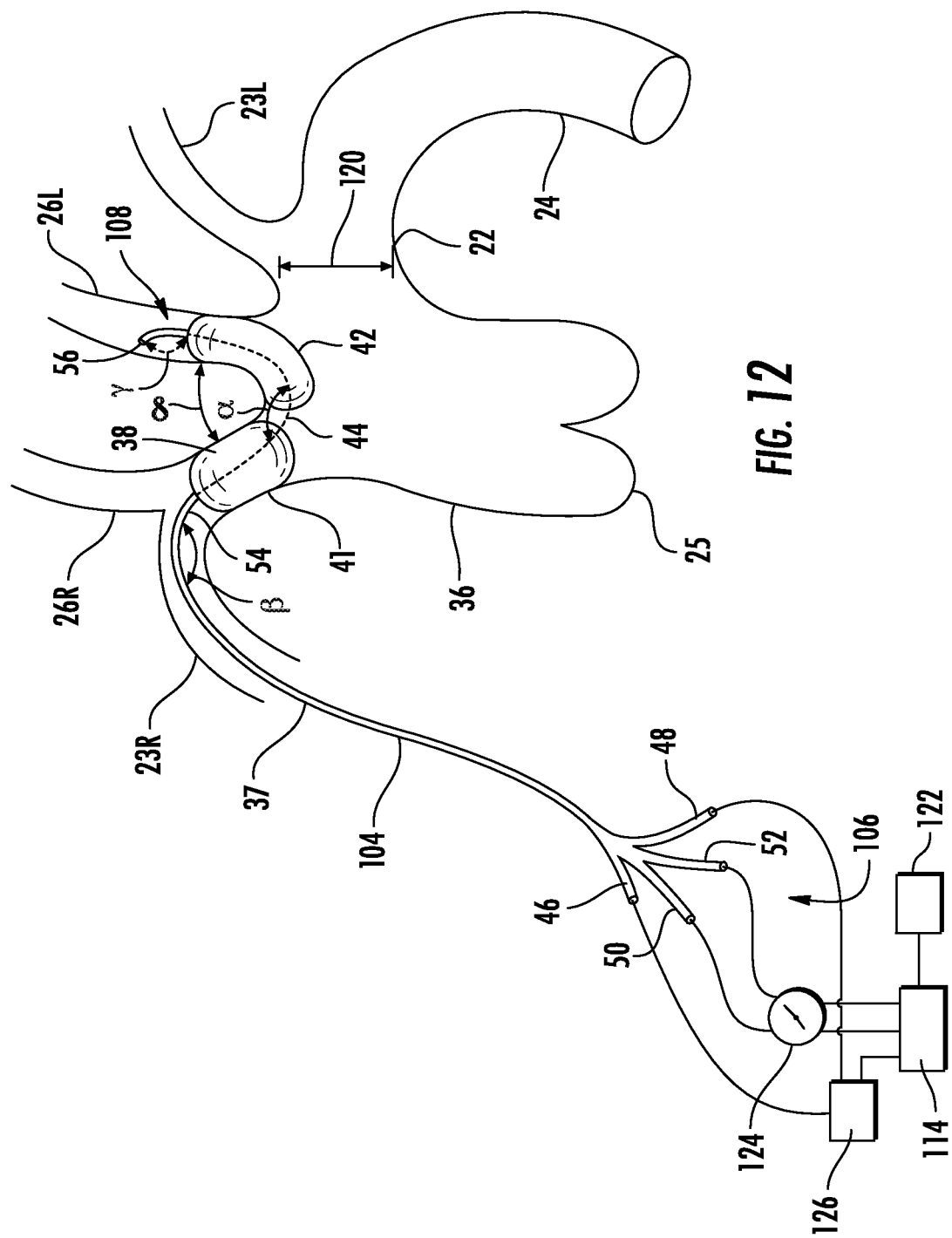
FIG. 12 is a front view of the patient with an inflated occluding catheter in accordance with a further exemplary embodiment.

Correct preferred placement of the distal occluding balloon 42 within the left carotid artery 26L may result in correct preferred placement of the proximal occluding balloon 38 within certain anatomical segments the innominate artery 41 and/or right subclavian artery 23R with a precise positioning of the segment 44 in the aortic arch at the level of the takeoff of the aortic arch branches such as arteries 41, 26L and 23L. This is achieved by choosing an occluding catheter 37 with the longitudinal length of segment 44 between proximal and distal occluding balloons 38, 42 to be equal, smaller or slightly larger than the distance between the innominate artery 41 and left carotid artery 26L, or left subclavian artery 23L, as estimated by preoperative CT scan, MRI or intraoperative Xray. According to some of our measurements, an optimal length of segment 44 should be either 0.5-2 cm shorter, or 0.5-6 cm longer than the distance between the innominate; artery 41 and the left carotid artery 26L or left subclavian artery 23L to allow for an adequate turn of the inter-balloon portion of the occluding catheter 37 within the aortic arch 22. Considering the fact that the average distance between the orifices of the innominate artery 41 and left carotid artery 26L in the normal aortic arch 22 configuration is from 0-2.5 cm, the length of segment 44 between the distal and proximal occluding balloons 38 and 42 should lie within the range between 0 cm and 8 cm depending on the angle Delta ($\delta$) of the takeoff of the left carotid artery 26L in relation to innominate artery 41 (FIGS. 2,3,12). The angle Delta ($\delta$) between the long axis of the left carotid artery 23L and innominate artery 41 according to our art may correspond, and approximate the angle Alpha ($\alpha$) of the curve of the catheter between the balloons 38 and 42 achieving the goal of congruency between the inner surface of the aortic arch adjacent to the ostia of aortic arch branches and the curve of the segment 44 of the catheter 37. Therefore, in practice several different sizes, shapes and curves of the occluding catheter 37 can be constructed where the length of the segment 44 between the proximal 38 and distal 42 occluding balloons vary from 0 to 8-12 cm and the angle Alpha ($\alpha$) would vary between 160 and 220 degrees corresponding to the angle Delta ($\delta$) of 0-45 degrees, while the radius of the distal catheter curve R1 would vary between 4 mm and 12 mm and the radius R2 of the mid-segment curvature of the catheter vary between 8 mm and 38 mm (FIGS. 5-A, 5-B). These measurements are derived from our anatomical studies of human aortas and their arch branches and are paramount to assure adequate positioning of the catheter by virtue of creating adequate points of fixation of the catheter segments against the arterial walls and adequate curvatures and angulations of the catheter in order to reach the desired target vessel such as left carotid, left subclavian, right carotid and/or innominate arteries.

The angle Delta ($\delta$) can be measured by measuring the angle between a central axis of the innominate artery 41 and the central axis of the left carotid artery 26L. Alternatively, the angle Delta (δ) could be measured by measuring the angle from external walls of the innominate artery 41 and left carotid artery 26L that are facing or closest to one another. The angle Delta (δ) can be expressed in units of degrees or can also be measured as a radius and expressed as a length. If a radius, the angle Delta (δ) is the radius of curvature of the curve at the outer surfaces of the innominate artery 41 and the left carotid artery 26L. The angle Delta (δ) can thus be a degree measurement or a radius of curvature length measurement. The angle Alpha (α) is measured by noting the bend in the segment 44 when the proximal and distal occluding balloons 38, 42 are inflated and measuring the angle between the central axis of the shaft 104 on one side of the bend to the central axis of the shaft on the other side of the bend. Alternatively, the outer surface of the segment 44 on one side of the bend could be measured against the outer surface on the outer side of the bend to determine the angle Alpha (α). The angle Alpha (α) could also be measured and expressed as a length instead of in degrees. Here the bend illustrates a curvature and this curvature has a radius of curvature that can be measured to either a curve of the central axis, or a curve of the inside portion of the shaft 104. The radius of curvature is R1 in FIG. 5A and this R1 is a length and is the angle Alpha (α). As such, the angle Alpha (α) may be measured either in degrees or in a length as a radius of curvature.

The angle Beta (β) is measured by noting the bend in the shaft 104 immediately proximal to the proximal occluding balloon 38 and measuring the angle between the central axis of the shaft 104 on one side of the bend to the central axis of the shaft 104 on the other side of the bend. Alternatively, the outer surface of the shaft 104 on one side of the bend could be measured against the outer surface on the outer side of the bend to determine the angle Beta (β). The angle Beta (β) could also be measured and expressed as a length instead of in degrees. Here the bend illustrates a curvature and this curvature has a radius of curvature that can be measured to either a curve of the central axis, or a curve of the inside portion of the shaft 104. The radius of curvature is R2 in FIG. 5A and this R2 is a length and is the angle Beta (β). As such, the angle Beta (β) may be measured either in degrees or in a length as a radius of curvature.

In addition, certain curvatures and bends of the shaft of the catheter, including a segment 44 may be constructed to achieve proper positioning of the distal tip of the catheter and distal occluding balloon in front of the points of takeoff of the left carotid artery 26L and/or left subclavian artery 23L, facing their respective ostia and assuming the shapes and curvatures amenable to coaxial course of the possible guidewire 142 or a wireless tip of the catheter with the central axis of the left carotid, artery 26L and/or left, subclavian artery 23L, thus allowing for an effortless access and advancement of the distal catheter tip and the distal occluding balloon into the left carotid artery with, or without use of the guidewire 142. At the same time such curvatures (Alpha, Beta, Gamma) and predetermined angles in the course of the catheter shaft (α, β, γ) would assure a coaxial course of the more proximal segments of the catheter carrying the proximal occluding balloon, thus achieving an optimal central coaxial position of the proximal balloon 38 in the innominate artery 41 avoiding an undue pressure or tension on the walls of the artery, and thus decreasing the chance of the vessel trauma during catheter positioning and inflation.

Compared to previous art, such an arrangement will substantially facilitate the process of catheterization of the innominate artery 41, left carotid artery 26L, and/or right and left subclavian arteries 23R, 23L, decreasing the time needed for insertion of the catheter into the left carotid artery 26L and other arteries (41, 26R, 23R, 23L), with the main goal of improving the learning curve and decreasing the risk of trauma to the vessel intima by the catheter tip and/or guidewire 142. As described in previous art, the process of entering the left carotid artery with the guidewire 142 and/or vascular catheter while using the right radial artery as an entry point, is very difficult due to the sharp angle Delta (FIGS. 2, 3, 4, 11) of takeoff of the left carotid artery from the aortic arch in relation to the takeoff of the innominate artery from the aortic arch. For this reason, the right radial access for catheterization of the left carotid artery was generally avoided. We may resolve this problem by combining different variations of several features disclosed in this application, such as: an optional floating capacity of the segment 44 and the distal segment of the catheter carrying the distal occluding balloon 42, pre-shaped curve of the segment 44 and/or distal segment of the catheter with an angulation congruent and conforming with the angle Delta (between the axes of the innominate 41 and left carotid artery 26L with or without the use of a guidewire 142) and angle Gamma (γ). Such angles could be measured and estimated by a dedicated assessment of patient's CT scan. In addition, the goal of an effortless access to the left carotid artery 26L, subclavian arteries 23R, 23L and innominate artery 41 may be achieved by creating several specific angulations throughout the length of the catheter such as angles and/or curves Alpha, Beta and Gamma (α, β, γ) and specific values of radii $R_1$ and $R_2$ as depicted on FIGS. 2, 3, 4, 5, 11-14 and points of fixation of the specific segments of the catheter shaft allowing for a safe and atraumatic contact of the catheter shaft with the parts of the blood vessels that are located downstream and/or away from cerebral vessels and, therefore, would not lead to cerebral embolization upon their instrumentation, while the innominate artery 41, left carotid artery 26L and adjacent area of the aortic arch will sustain minimal or no contact with the catheter. For example, when the point of catheter fixation β reaches the right subclavian artery 23R, the proximal occluding balloon 38 occupies an optimal central coaxial position at the innominate artery 41, while the segment 44 would form another curve at the angle Alpha(α) assuring its optimal coaxial position in the area of the aortic arch adjacent to the point of takeoff of the left subclavian 26L and left carotid 26L arteries, creating an optimal geometric position for their catheterization. Curvature angle Gamma (γ) can be measured when the distal occluding balloon 42 is inflated and is not inflated. The tip is the portion of the shaft 104 distal to the distal occluding balloon 42. The longitudinal axis of the shaft 104 in the tip is measured to the longitudinal axis of the shaft 104 that is surrounded by the distal occluding balloon 42 to arrive at the curvature angle Gamma (γ). If the distal occluding balloon 42 is not inflated, the curvature angle Gamma (γ) could alternatively be measured from the outer surface of the shaft 104 at the tip to the outer surface of the distal occluding balloon 42. The curvature angle the curvature angle Gamma (γ) could increase in size upon distal occluding balloon 42 inflation if the tip is angled all ready during insertion so that it is straightened out like in FIG. 3 after desired positioning is achieved. In other embodiments, the curvature angle Gamma (γ) decreases upon inflation of the distal occluding balloon 42.

According to our measurements the angle between the part of the catheter carrying the distal occluding balloon 42 and the part of the catheter, carrying the proximal balloon 38 should, range between 180 and 220 degrees with the distal part of the catheter aiming at the central axis of the proximal balloon and/or segment 44 of the shaft to assure adequate deflection of the distal part of the catheter upon insertion of the guidewire 142 in order not to over-extend the catheter to the point beyond the area of takeoff of the left carotid artery that may compromise a successful insertion of the guidewire 142 into the left carotid, artery. In addition the distal tip of the catheter located at the distal balloon 42 may have an angle Gamma (γ) ranging between 120 and 230 degrees in relation to the long axis of the catheter shaft that would increase the range of catheter deflection and provide more versatility during the catheter torqueing and further manipulation with, or without using a guidewire 142 in order to get an access to the ostia of the Left carotid and Left subclavian arteries.

In some embodiments the radius and the angulation of the catheter curvature can be predetermined to achieve an optimal positioning of the tip of the catheter carrying the distal occluding balloon 42 against the ostium of the left carotid artery 26L while, and as soon as the area of the proximal balloon 38 is positioned at the level of the ostium and/or proximal segment of the innominate artery 41. Based on multiple measurements and studies performed by the Applicant, the optimal radius of the catheter curvature located between the proximal 38 and distal 42 balloon is in the range of 6 mm+/−3.4 mm (Mean+/−SD) as the average distance between the axial centers of the innominate 41 and left 26L carotid arteries is 12+/−5.2 mm. This measurement analysis is with a more than 95% confidence interval irrespective of the patient's diagnosis, age (within the range between 20 and 92 years old), weight and other physical parameters. Thus if the radius of the distal curve of the catheter is 6 mm and the angle of the distal part of the curve of the catheter carrying, the distal balloon 42 in relation to the part of the catheter carrying a proximal balloon 38 is 180 degrees, there is more than a 95% chance to achieve a quick, efficient and successful catheterization of the left carotid artery 26L, irrespective of the patient's age, diagnosis, weight, and any other physical characteristics. This makes the procedure of simultaneous catheterization and occlusion of the ostia and/or proximal segments of innominate 41, left carotid 26L and/or left subclavian branches of the aoric arch 22 a much easier procedure than it was previously anticipated. To maintain the curvature of the distal tip of the catheter at the required angle and shape, a specifically designed nitinol (or any other material-based) coil 202 can be embedded into the distal end of the catheter, and/or catheter shaft material can be curved at the required angle of 180+/−30 degrees and a radius of 6.0+/−3.4 mm to achieve this goal. A coil 202 is shown with reference to FIG. 21 and is embedded in the shaft 104 imparting a curved distal tip 56.

In addition, an extension of a proximal balloon 38 and/or distal balloon 42 into the curvature of the curved segment 44 with an optional stretching of the balloons towards the pivot point of the segment 44 with creation, of a tension throughout the length of the catheter shaft covered by balloons 38, 42 would create an opportunity to achieve a desired angle of flexion (angle Alpha, a) of the segment 44 of the catheter to facilitate the entry of the ostia of the left carotid 26L and/or left subclavian 23L arteries with or without use of a guidewire by virtue of varying the degree of the proximal 38 and/or distal 42 balloon inflation and distention of the balloon tissue, thus exerting a desired degree of balloon stretching and leading to the appropriate angulation of respective areas of the segment 44 that may be partially or totally covered by the inflatable balloons 38 and 42.

Figure 11:
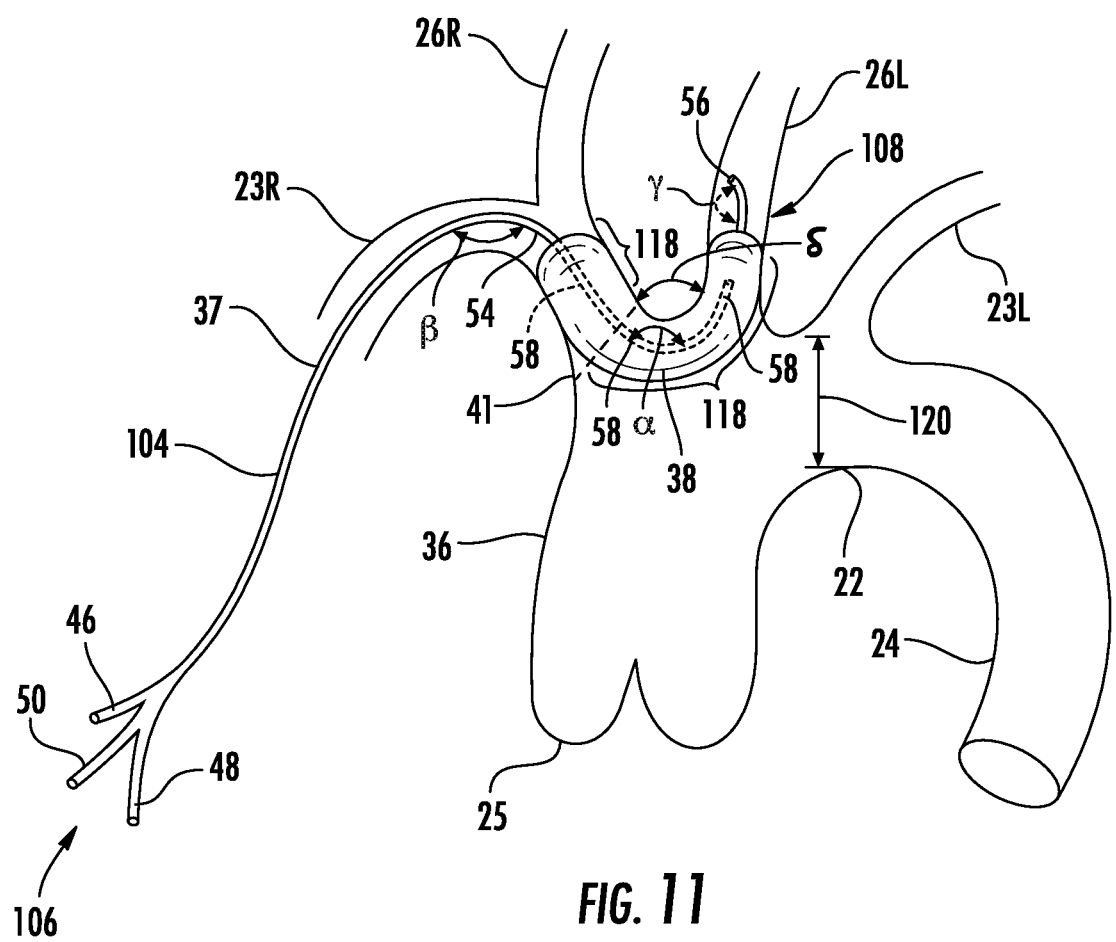
FIG. 11 is a front view of the patient with an inflated occluding catheter in accordance with another exemplary embodiment.

For example, in order to achieve a steeper curvature and flexion of the segment 44 of the catheter one may start inflating proximal balloon 38 and/or 42 leading to increased tension on the proximal and/or distal parts of segment 44 due to increased tension of the inflated balloons. Once the desired angle Alpha (α) of 180+/−30 degrees is obtained and the tip 56 of catheter 106 is positioned against the orifice of the left carotid 26L and/or left subclavian 23L artery, the catheter can be advanced reaching the orifice and the proximal segment of the artery to be occluded (23L and/or 26L), thus facilitating the process of catheterization (FIGS. 11, 12, 16). This arrangement will create a catheter 106, where all necessary and adequate manipulations, angulations and torqueing of the catheter will be strictly controlled by the operator and would not lead to undue contact or traumatize the innominate artery 41, right carotid artery 26R, left carotid artery 26L, and/or left subclavian artery 23L. The process of reaching the ostium and proximal segment of the left carotid artery 26L, left subclavian artery 23L or any other vessel of the thoracic aorta and its branches for a successful catheterization and balloon occlusion will be substantially shortened, facilitated and made much safer.

The diameter, length, size, volume, coaxiality (which can be concentric or eccentric) of the occluding balloons 38, 42 and the degree of their extension into the segment 44 and stretching of the balloon material may also vary according to he needs of the operator with the main goal being to achieve a desired angle of flexion Alpha (α) of the segment 44 and/or angles Gamma and Beta of more distal, and/or more proximal segments of the catheter 106 (FIGS. 4 and 5). These variables such as the desired angles and curvatures of the catheter may vary depending on the patient's anatomy with the proximal occluding balloon 38 in some embodiments being 50-250% longer and larger than its distal 42 counterpart, and/or positioned eccentrically in relation to the axis of the catheter with the larger area of the balloon being located either inside or outside of the curve of the catheter thus promoting further catheter flexion, extension, lateral bending and/or a combination of thereof by virtue of a different degree of the balloon inflation, thus creating a new disclosed method of catheterization of the left carotid 26L, innominate 41, and/or left subclavian 23L arteries by using a variable degree of balloon inflation leading to a desired degree of the catheter flexion to reach a target artery. The length of segment 44 may vary from 0 to 80 mm and may be selected in each particular patient in such a way that when the proximal occluding balloon 38 is located within the proximal, middle, distal or all segments of the innominate artery 41, the distal occluding balloon 42 would occupy a position within the ostium and/or proximal segment, or any desired segment of the left carotid artery 26L and/or left subclavian artery 23L.

The next step in the method of using the occluding catheter 37 may be further inflation through the common inflation port 130 and/or 138 (FIG. 5-D) and a common inflation channel 132 and/or unified channels 68, 70, 72 (FIGS. 6-10) to achieve an expansion of a proximal occluding balloon 38 in the lumen of the innominate artery 41 and an option of recording of pre- and/or post-occlusion pressure in the distal innominate artery 41. This pressure may be recorded via a pressure wire 74 of the shaft 104 located upstream and/or downstream from the proximal occluding balloon 38 and/or distal occluding balloon 42 in the direction of arterial blood flow. A pressure measurement wire 74 is in communication with the area 54 and with an intermediate pressure measurement port 52 at the proximal end 106. This port 52 can be used to confirm an adequate position of the proximal occluding balloon 38 by the appearance of the dampened arterial pressure waveform. Once the pressure measurement indicates that the proximal occluding balloon 38 is properly positioned, the proximal occluding balloon 38 can be deflated and the occluding catheter 37 is considered ready for use. The interruption of carotid and/or vertebral arterial flow or pulse may be assessed by angiography, arterial Doppler, transcranial Doppler, or arterial pressure and waveform patterns distal to the level of occlusion in accordance with certain exemplary embodiments. In addition, percutaneous cerebral oximetry, electroencephalography and transcranial Doppler monitoring can be applied. In other arrangements, it may not be the case that this monitoring is applied in order to confirm positioning of the proximal and distal occluding balloons 38, 42.

The proximal and distal occluding balloons 38, 42 may be inflated such that they are both inflated at the same time as shown with reference to FIG. 3. Simultaneous inflation may lead to temporary interruption of the carotid and/or vertebral arterial flow, preventing all potential emboli 28, released due to manipulations on atherosclerotic calcified plaques 29 of the ascending aorta 3 (or from other such embolignic events) from entering the cerebral circulation, and diverging them downstream from the cerebral circulation into the descending aorta 24, thus protecting the patient from embolic stroke.

An expeditious simultaneous inflation of both distal and proximal occluding balloons in anticipation and/or upon appearance of potential cerebral emboli, is paramount for an adequate prevention of cerebral emboli and embolic stroke as any delay in inflation of these balloons may cause the entry of emboli into cerebral circulation causing stroke. Such inflation is achieved by using a disclosed common inflation port 130 and/or 138 and a common inflation channel 132 connected to both proximal and distal balloons (FIG. 5-D), where an injection of gas or fluid from a single source will lead to synchronous actuation of all occluding balloons blocking the flow to both right and left carotid arteries and/or right and left subclavian and vertebral arteries simultaneously. Such injection can be easily carried out using a single injection syringe or an inflation apparatus, connected to the common inflation port 130 with the whole manipulation being performed single-handedly, if needed, and achieving a significant advantage compared to previous art, where the injection had to be performed separately trough 2 different ports. Similarly, a much quicker and more efficient deflation of both the proximal and distal occluding balloons 38 and 42 may be achieved by a single-handed or automated deflation via a common port 130 and common inflation channel 132, once the potential cerebral emboli have been deflected and the risk of cerebral embolization has been eliminated. The common inflation port 130 and inflation channel 132 have distal openings 58 at the proximal balloon 38 and distal openings 60 at distal balloon 42 and in some embodiments may represent the same port and channel for the insertion of a guidewire 142 with an opening 56 for the guidewire 142 at the distal tip of the catheter. In this particular embodiment the inflation channel 132 may also for at least some of its length serve as a guidewire 142 channel ending at the tip 56 of the catheter. The area 56 of the tip of the catheter may be a distal orifice allowing the guidewire 142 to pass through (with or without a possibility for air or fluid to leak between the guidewire 142 and the walls of it channel through the orifice 56 depending on the degree of approximation of the inner diameter of the catheter tip channel 70 and/or 72 and the outer diameter of the guidewire 142). However, in some embodiments the orifice 56 at the distal tip of the catheter may be completely closed with the guidewire 142 and/or balloon inflation channel ending at the point 56 of the catheter. This embodiment would achieve the goal of using a common inflation-guidewire channel 132 and/or 134, 136 for both insertion of a guidewire 142 and simultaneous inflation of the balloons. This function will be performed better with the inflation openings 58 and 60 being much narrower than the outer diameter of the guidewire 142 and with the inflation port 130 carrying a Tuohy-Borst type adaptor for using a single port 130 and/or 134, 136, 138 for both balloon inflation and insertion of a guidewire 142. In other embodiments, however, the catheter may have a separate port 50 for insertion of a guidewire 142 and a port 130 for balloon inflation (FIG. 5-A). In these embodiments the guidewire 142 port 50 may continue into a separate guidewire 142 channel 70 having a distal opening 56 or have a common channel with the inflation channel 132 with either opened distal orifice 56 or no distal opening at all. In some embodiments the difference in the disclosed balloon features allow for simultaneous vs. selective initial inflation of the distal balloon vs. proximal balloon and vice versa in spite of a common inflation channel 132 and inflation port 130. This is achieved by virtue of a variety of the disclosed combinations and values of the relative balloon features, such as balloon compliance, size, volumes, diameters and shapes.

For example, in one embodiment both balloons can be made of the same material and have the same volume. As such, their inflation via the common port 130 and channel 132 will lead to their simultaneous inflation, where the proximal balloon 38 may be inflated in the innominate artery, while the distal balloon 42 may get inflated in the left carotid artery. Considering the differences in the diameters of the Innominate (41) and Left carotid (26L) arteries which, as disclosed in our art, averages the ratio of 2:1, the corresponding dimensions of the distal balloon 42 in relation to the proximal balloon 38 should vary proportionally to the degree of diminution of its diameter according to the formulas of the volume of the sphere, cylinder or any other geometric with a proportional increase in its length in order to maintain its volume similar to the volume of the proximal balloon 38. Such dimensions may be calculated using mathematical formulas for calculations of the volume of sphere vs. the volumes of different types of cylinder, cones, pear shape, and other shapes of balloons. For example, if one desires to build a 2-balloon catheter with both proximal balloon 38 and distal balloon 42 made out of the same material, or a material with a similar compliance and inflated simultaneously via the same port 130 and channel 132, where the desired inflation diameter of a proximal balloon 38 is 2 cm and the inflation diameter of a distal balloon 42 is 1 cm, then according to the formula and assuming that a distal balloon 42 is a cylinder, then the optimal length of the distal balloon 42 should approximate 5.3 cm in order to match the volume of the proximal balloon 38, where the diameter of the proximal balloon is 2 cm.

Similar calculation may be made for any shape of the distal and proximal balloon, including mixed shapes and combination of shapes and compliance values by adding the most suitable calculations to estimate the volume, diameter, and other dimension parameters of the balloons with an option of a software program allowing for an instantaneous suggestion of an adequate dimension of the distal balloon in relation to the proximal balloon, when calculating a desired balloon diameter leading to the vessel occlusion. Such software may include a variety of parameters influencing the degree of expansion of 2 or more balloons made out of similar or non-similar material with a specific degree of compliance, volume and shape.

Figure 13:
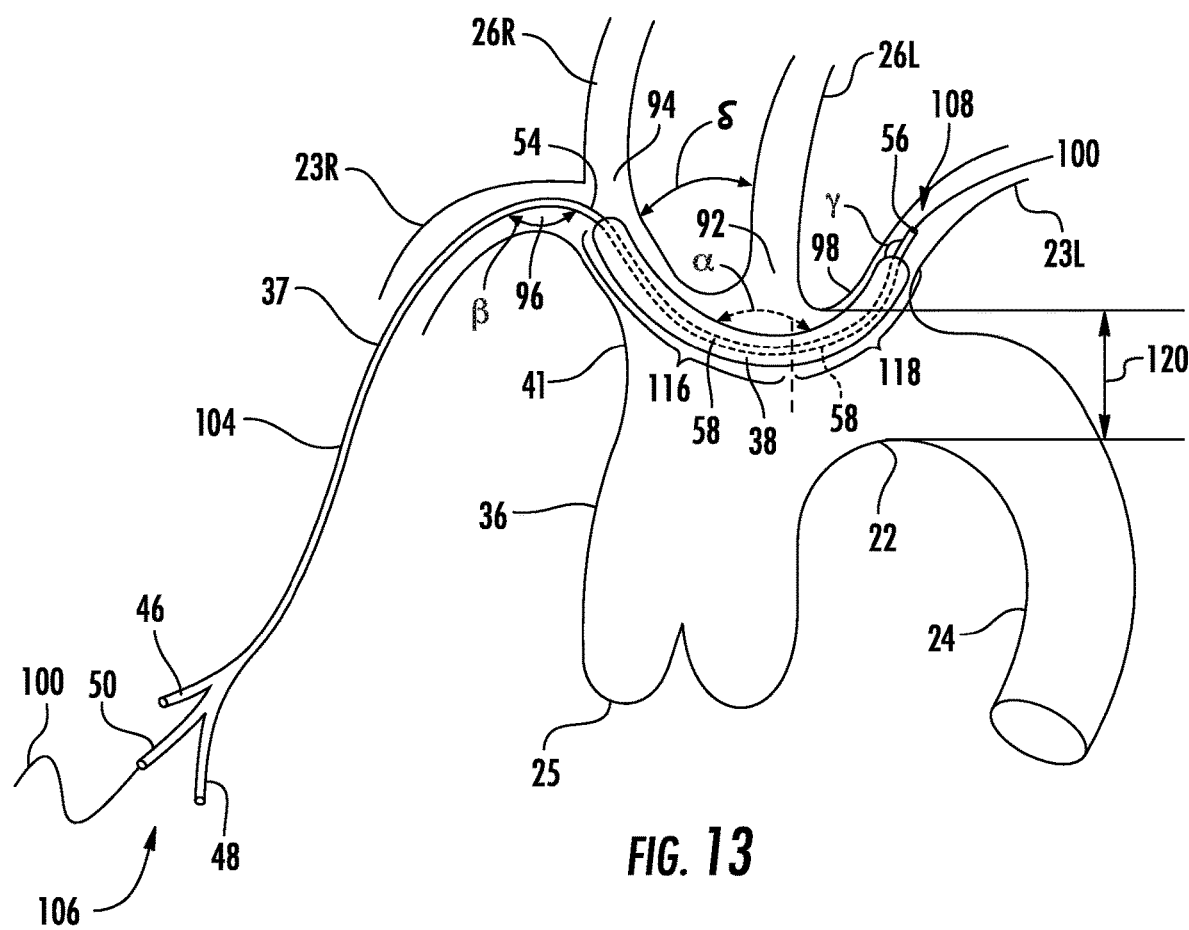
FIG. 13 is a front view of the patient with a deflated occluding catheter introduced via the arteries of the right arm in accordance with another exemplary embodiment.
Figure 15:
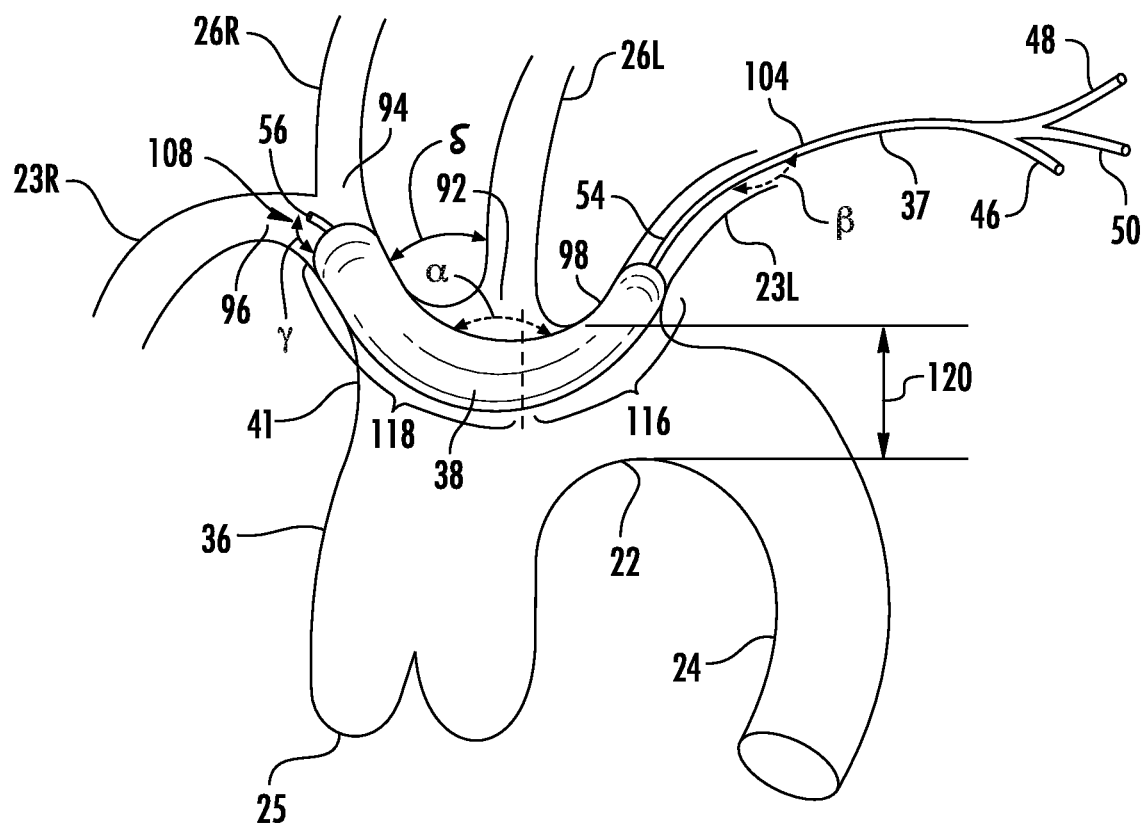
FIG. 15 is a front view of the patient with an inflated occluding catheter of FIG. 13, but introduced instead through the arteries of the left arm in accordance with a still further exemplary embodiment.

Another embodiment would include a single elongated balloon extending through the segment 44 with its distal portion corresponding to the distal balloon 42 and the proximal portion—corresponding to the proximal balloon 38 (FIGS. 13, 14, 15). To assure a synchronous and adequate degree of expansion in relation to a larger innominate artery and a smaller left carotid artery, such a single balloon may have at least one of the following features: different compliance of the proximal versus distal segment, different shape of the proximal vs. distal balloon segment and/or different diameter and relative volume of the proximal vs. distal balloon segment. In this case, an inflation of this type of a single balloon via a single source may lead to a preferential balloon expansion within a larger innominate artery and a lesser expansion within a smaller carotid artery with a goal ratio of 2:1 as determined by an average ratio of the diameter of innominate artery in relation to the diameter of the left carotid artery in every single patient.

According to our findings the diameter ratio of innominate artery 41 to left carotid artery 26L in humans closely approximates 2:1 with the majority of innominate arteries being less than 20 mm in diameter and left carotid arteries—less than 10 mm in diameter. Based on these data one of the optimal embodiments of an adequate balloon diameter that would fit the majority of patients would be a proximal balloon 38 being 20 mm in diameter and a distal balloon 42 being 10 mm in diameter. However, in case, if these balloons are made of a similar material and/or are have identical compliance in order to achieve an even and synchronous inflation of these balloons to their required diameters, the volumes of these balloons must, be equal and/or adjusted to the discrepancies of the balloon diameters, balloon shapes and the forces of surface tension according to the Laplace's Law. For example, in the one of the embodiment of a 2-balloon, single inflation catheter disclosed in our art, the proximal balloon 38 may be a sphere with a diameter of 20 mm and a calculated volume ($V_{prox}$) equal to:

$$V_{prox} = 4/3 \times \pi \times r^3_{prox} = 4/3 \times \pi \times 10^3 = 4188.79 \text{ mm}^3$$

where $\pi$—Pi value equal to 3.141828; $r_{prox}$—proximal balloon Radius (equal to 10 mm), whereas, the distal balloon 42 may be a cylinder with a diameter of 10 mm and a calculated volume ($V_{dist}$) equal to:

$$V_{dist} = \pi r^2_{dist} \times h,$$

where $\pi$—Pi value equal to 3.141828, $r_{dist}$—distal balloon Radius (equal 10 mm), and h—is the height(length) of the cylinder-shaped distal balloon.

Assuming that the volumes of proximal and distal balloons must, be made equal ($V_{prox} = V_{dist}$) one may calculate the required height "h" (length) of the distal cylindrical balloon 42 using following equations:

$$V_{prox} = V_{dist}$$

$$V_{prox} = 4/3 \times \pi \times r^3_{prox}$$

$$V_{dist} = \pi r^2_{dist} \times h$$

$$4/3 \times \pi r^3_{prox} = \pi r^2_{dist} \times h,$$

where $r_{dist} = 5$ mm and $r_{prox} = r_{dist} \times 2 = 10$ mm

In this case the height (length) "h" in millimeters can be calculated as follows:

$$h = \frac{4/3 \times \pi r^3_{prox}}{\pi r^2_{dist} \times h} = 4/3 \times \frac{r^3_{prox}}{r^2_{dist}} \times h =$$

$$4/3 \times \frac{(r_{dist} \times 2)^3}{r^2_{dist}} = 4/3 \frac{(5 \times 2)^3}{(5)^2} = 4/3 \frac{1000}{25} == 4/3 \times 40 = 53 \text{ (mm)}$$

Therefore, if the proximal balloon diameter needs to be 20 mm (radius 10 mm) and the distal balloon diameter needs to be 10 mm (radius 5 mm) then—to create conditions for simultaneous and equal degree and rate of expansion using a single and/or common inflation channel for both balloons one must create equal volumes for both balloons 38 and 48 and this is achievable by creating a length (height) "h" of a distal balloon equal to 53 mm, provided a distal balloon 42 has a cylindrical configuration.

As an example of equalizing the balloon volumes in presence of significant differences of their diameters in order to be able to synchronously inflate these balloons, one may calculate the required, dimension, of a proximal spheric balloon with an expanded radius of 10 mm and a cylindrical distal balloon with the radius of expansion of 5 mm. The calculations of size and volume may be taken assuming there is no restrictive forces against the balloons 38, 42 such that the volume are measured in their maximum inflate state. The volumes are not measured assuming the balloons 38, 42 are inside of the arteries and being compressed.

Equal total balloon surfaces of both balloons, in spite of a proximal balloon having a radius 2 times larger than a distal balloon, would assure equal balloon wall tension inside, leading to an equal rate of balloon expansion, if inflated via a common channel.

For example (FIG. below), if a proximal balloon 38 has a diameter of 2 cm (radius=1 cm), then its volume will be 4,189 cm3 according to a standard formula of volume calculation for a sphere. In this case in order to match the volume of a proximal balloon 38 (4.189 cm$^3$) the distal balloon 42, while having a smaller diameter of 1 cm (radius=0.5 cm) and a shape of a cylinder, must have an increased length (i.e. height of a cylinder) which according to standard formulas for calculation of a cylinder volume should be equal to 5.33 cm with a calculated volume of a distal balloon being 4,186 cm$^3$, i.e closely approximated to the volume of the proximal balloon 38. As a result the occluding catheter with the balloons of these dimensions will be able to be used for simultaneous occlusion of 2 independent vessels of different sizes, while using a single source for inflation of both occluding balloons 38 and 42, in spite of differences in their diameters.

Balancing the differences in the balloons' volumes, diameters and compliances would allow one to achieve a goal of a controlled balloon expansion in order to perform an adequate occlusion of a larger innominate artery 41 and a smaller carotid artery 26L (or left subclavian artery 23L).

Similar approach to determine the variations in sizes and shapes of the occluding balloons while preserving their equal degree and rate of expansion using a single inflation channel may be used while calculating same parameters for different variations and combinations of occluding balloons in the shapes of spheres, cylinders, cones, cubes, capsules, spherical caps, ellipsoids and combinations of thereof.

For example, in the embodiment, where both balloons are represented with ellipsoids, a proximal balloon 38 that needs to be 20 mm in diameter and 30 mm in length, would have a volume of 6283.18 mm$^3$ as per the following formula:

$$\text{volume} = \frac{4}{3}\pi abc$$

where a, b, and c are, the radial lengths (radiuses) of the vertical, horizontal and long (longitudinal) axes respectively In this case to create a distal balloon 42 that would have a diameter of 10 mm (vertical axis or radius "a"="b"=5 mm) and yet have a similar volume of 6283, 18 mm³ one must vary the horizontal axis "b" and long axis "c" of the distal balloon 42, i.e.:

$$V_{dist} = V_{prox} = 6{,}283 \text{ mm}^3, \text{ or } 4/3 \times \pi a_{prox} b_{prox} c_{prox} = 4/3 \times \pi a_{dist} b_{dist} c_{dist}$$

where $a_{prox} = b_{prox} = 10$ mm
$a_{dist} = b_{dist} = 5$ mm $= \frac{1}{2} a_{prox} = \frac{1}{2} b_{prox}$
$c_{prox} = 15$ mm,
and $$C_{dist} = \frac{a_{prox} b_{prox} c_{prox}}{a_{dist} b_{dist}} = \frac{a_{prox} b_{prox} c_{prox}}{\left(\frac{1}{2} a_{prox} \times \frac{1}{2} b_{prox}\right)} = 4 \frac{a_{prox} b_{prox} c_{prox}}{a_{prox} \times b_{prox}} = 4 \times C_{prox} = 60 \text{ mm}$$

i.e.: the whole length of the distal occluding balloon 42 would have to be 60 mm×2=120 mm in order to match the volume of the proximal balloon 38, when the diameter of the proximal balloon is 20 mm and the diameter f the distal, balloon is 10 mm.

Similarly, if one or both of the balloons are represented by a different shape such as a capsule, cone, hemisphere, sphere, etc., one may calculate the required size and, length of the balloons in order to maintain the required ratio of their diameters approximating 2:1 (proximal balloon 38 to distal balloon 42). For example, for a capsule, these calculations will be derived from the formula of a capsule volume and will be compared with the calculations of volumes from formulas of other geometric shapes using a similar approach as described above.

$$\text{Capsule Volume Formula: volume} = \pi r^2 h + \frac{4}{3}\pi r^3 = \pi r^2 \left(\frac{4}{3}r + h\right)$$

where r is radius and h is height of the cylindrical portion.

In some embodiments the length of the distal occluding balloon 42 that exceeds 10-30 mm may not be desirable, while the length of the proximal balloon 38 must be at least 15-45 mm. In this case it would be difficult to achieve an equal balloon volume in the setting, where the maximal acceptable diameter of the distal balloon is close to 10 mm and the minimal acceptable diameter of the proximal balloon is close to 20 mm, without an undue (ill-indicated) elongation of the distal balloon 42 and/or undue shortening of the proximal balloon 38.

In order to resolve these issues and yet to preserve a similar rate of expansion of both balloons while they are inflated via a common and/or communicating inflation channel 132 and/or 68, one may change a relative compliance of a proximal vs. distal balloon, where the distal balloon 42 that has a smaller volume would expand with an equal rate as a proximal balloon 38 that has a larger volume and both balloons will reach the goal of occlusion of arteries 41 and 26L (and/or 23L) simultaneously, in spite of differences in their (balloons and arteries) sizes, volumes and diameters. To achieve this goal, we disclose a compliance ratio of the distal vs. proximal occluding balloon that is dependent on the ratio of the dimension parameters of both balloons. This ratio reflects an interrelationship between the structural and dimensional characteristics of both balloons, such as balloon's compliance, size, shape and volume and may be assessed by measuring the inflation rate of balloons 38 and 42. As we have shown during our bench experiments, the larger proximal balloon 38 would expand much faster, than the distal smaller balloon 42 when both balloons are inflated (actuated) via a common channel 132, unless at least one of several important alteration to the structure of the catheter and its balloons are made.

For example, in some embodiments the decrease of the distal balloon 42 in volume may be compensated by a proportional increase of its material's compliance and/or proportional decrease in the compliance of the material representing the proximal occluding balloon 38. In accordance with various embodiments, the proximal occluding balloon 38 may have a diameter that is 50 percent greater (0.5 times greater) than the diameter of the distal occluding balloon 42, or may have a diameter that is 100 percent greater (therefore 2:1) than the diameter of the distal occluding balloon 42.

Yet, in another embodiment the surface tension of both balloons may be equilibrated by adjusting their shapes with the larger proximal balloon 38 being more round and/or oval and therefore having less degree of the surface tension, whereas the distal smaller balloon 42 would be more cylinder-like having a relative increase in the numbers of surface tension to approximate these numbers in the proximal balloon 38.

The goal of preserving the equal rate of balloon expansion during their inflation via a common and/or communicating channel 132 may be obtained by varying the ratio of the degree of compliance (C) of the material used for the distal balloon 42 (less or more complaint) in relation to the compliance of the material used for the proximal balloon 38 (less or more compliant) or vice versa with the result being a 2:1 expansion of the proximal (innominate) balloon 38 in relation to the distal (left carotid) balloon 42 while having a single port for injection that is connected to both balloons. Considering the fact that the proximal balloon 38 is much larger than the distal balloon 42, the compliance of the former may have to be lower, while the compliance of the latter—may have to be higher in order to counteract the effect of the Laplace's law, where the balloon of a larger volume will experience a much higher surface tension than the balloon of a smaller size in case when both balloon are inflated via the same channel 132.

For example, if we assume (in order to simplify our calculations) that both proximal larger balloon 38 and distal smaller balloon 42 have a spherical shape, we may apply a Laplace's Law formula to calculate tension T for each balloon ($T_{prox}$ and $T_{dist}$) depending on their Radiuses ($R_{prox}$ and $R_{dist}$),
where $R_{prox} = 2 \times R_{dist} = 2 \times 5$ mm = 10 mm,
i.e.:

$$T_{prox} = F/2\pi \times R_{prox} = F/2\pi \times 2R_{dist} \qquad [1]$$

and $$T_{dist} = F/2\pi \times R_{dist} = F/2\pi \times \tfrac{1}{2}R_{prox} \qquad [2]$$

If we calculate the ratio of $T_{prox}$ (formula [1]) to $T_{dist}$ (formula [1]), we will obtain:

$$T_{prox}/T_{dist}=1:2.$$

i.e.: the ratio of surface tension of the larger proximal balloon 38 to the tension of the smaller distal balloon 42 when the radius of the proximal balloon 38 is 2 times larger than the radius of a distal balloon 42 equals 1:2, regardless of a numeric size of the balloons.

Furthermore, assuming that the Compliance (C) of each balloon is inversely proportional to their surface tension T (C=1/T), one may calculate that the compliance ratio of the balloons 38 and 42 would be 2:1, where $$C_{prox}=1/T_{prox} \text{ and } C_{dist}=1/T_{dist}$$

and therefore:

$$C_{prox}/C_{dist}=T_{dist}/T_{prox}=2:1$$

or $C_{dist}=C_{prox} \times 2$.

Therefore, should both balloons be expanded by inflation via the common channel 132 or communicating channel 68, the proximal balloon 38 will expand two times faster than the distal balloon 42 proportionally to their compliance ratio. As a result the proximal balloon 38 may expand and occlude the artery 41 way before the distal balloon 42 has begun its expansion. Moreover, the distal balloon 42 in this setting may never fully expand as with incremental expansion of a larger balloon 38, its compliance will proportionally increase leading to incremental decrease in the compliance of a distal balloon and its eventual collapse, as occurs in two communicating bubbles of different diameter.

To solve this problem we are disclosing a structural modification of the balloon composition consisting in choosing a balloon material of lower compliance for a larger balloon 38 in relation to the smaller balloon 42. The compliance of the proximal balloon material may be higher by the same factor as a calculated ratio of the balloons' surface tension, radii and other dimensions, necessary to calculate their surface ratio (these dimensions and formulas may vary depending on the shape of the balloon and can be calculated similarly to our examples presented above). For example, if a calculated compliance ratio of the proximal versus distal balloon is found to be 2:1 (as discussed above) then the compliance of the proximal balloon must be increased by the factor of 2. This can be achieved by choosing a balloon material of a higher durometer number. For example, if the compliance of the material representing a distal, balloon 42 is 0.5 durometers, than the compliance of the material, used to build a proximal balloon must be 1.0 durometers. This arrangement will create conditions for a synchronous expansion of the balloons of the disclosed catheter, while using a common channel 132 and/or communicating channel 68 for their actuation.

Assuming that balloon compliance (C) is inversely proportional to its wall tension, i.e. C=1/T (Tension), or $$C = k \times \frac{1}{T},$$

we may conclude that the compliance(C) of an occluding balloons 38, 42 is an inversion value of tension (T).

On the other hand, if one or more of the occluding ballooned have a different shape the formulas of Tension (T) and Compliance (C) need to be adjusted accordingly to the shape of each balloon, yet the principle of the inverse correlation between the diameters, radiuses, volumes and compliances of the proximal vs distal balloons will remain, yet it will have to be adjusted to the volumes, tension and compliances calculated for each specific shape and size of the occluding balloon.

For example, the Tension (T) of the spheric balloon is calculated using the formula T=PR/2, whereas for a balloon of a cylinder shape, the Tension (T) is calculated as T=PR, where P—pressure inside the balloon and R is its radius. Therefore, the compliance C=1/T of a spherical balloon would be 2 times higher than the compliance (C) for a Cylindrical balloon, if their radiuses and materials are equal. However, if we apply the disclosed 2:1 diameter (or radius) ratio of the proximal versus distal balloon then the resulting calculations would allow to create a synchronous inflation pattern via a common inflation channel allowing for a synchronous expansion of balloons of a similar rate and degree with simultaneous occlusion of a larger innominate artery 41 and a left carotid artery 26L, or a left subclavian artery 23L.

In this case we may apply a Laplace's Law formula to calculate the tension T for each balloon ($T_{prox}$ and $T_{dist}$) depending on their radii ($R_{prox}$ and $R_{dist}$), where $R_{prox}$ may be equal to $2 \times R_{dist} = 2 \times 5$ mm=10 mm, and where a proximal balloon 38 is a cylinder, whereas a distal balloon 42 is a sphere, i.e.:

$$T_{prox(Cylinder)}=P \times R_{prox} \text{ and } T_{dist(Sphere)}=\frac{1}{2}(P \times R_{dist}),$$

where P—mean pressure in the artery (mmHg)

If $C_{(Compliance)}=1/T,$ then for a proximal (cylinder-shape) balloon 38 and a distal (spheric) balloon 42:

$$C_{dist}/C_{prox}=T_{prox}/T_{dist}=(P \times R_{prox})/\tfrac{1}{2}(P \times R_{dist})=2 \times R_{prox}/R_{dist}$$

and, if $R_{prox}=2R_{dist}$(such as $R_{prox}=10$ mm and $R_{dist}=5$ mm), then; $C_{dist}/C_{prox}=2 \times R_{prox}/R_{dist}=2 \times 2R_{dist}/R_{dist}=4,$ or $C_{dist}=4 \times C_{prox}$ In other words, in a catheter embodiment, where a distal balloon 42 is represented by a sphere, and a proximal balloon 38 is represented by a cylinder, prox is their relative compliance ratio $C_{dist}/C_{proportional}$ to the "double" (i.e. ×2) inverse ratio of their respective diameters ($2 \times R_{prox}/R_{dist}$).

For example, if we want to assure that the rate of a proximal balloon 38 and distal balloon 42 expansion during their inflation via a common channel 132 has the same rate, then we may calculate the required compliance ratio of each balloon, depending on their size and shape in order to satisfy a disclosed requirement of the proximal balloon radius (or diameter) to be at least 180%-220% (average 200%) larger than its counterpart. As a result, the larger proximal balloon may be made of a less compliant material than a distal balloon 42 with their compliance being adjusted to assure a similar degree of resistance to inflation, when the inflation is performed via the common inflation channel.

Thus, if a distal balloon 42 is a sphere with a radius of $R_{dist}$ of 5 mm, and a proximal balloon 38 is a cylinder with a radius $R_{prox}$ of 10 mm, where a tension (T) according to the Law of Laplace equals:

$$T_{prox\ Cylinder}=PR_{prox} \text{ and } T_{dist\ Sphere}=PR_{dist}/2,$$

where P—pressure in both balloons needed to reach the patient's mean arterial pressure (normal—60 mm Hg) in order to induce vessel occlusion;

then, $T_{prox\ Cylinder} = PR_{prox} = 60\ mmHg \times 10\ mm = 600$ and $T_{dist\ Sphere} = PR_{dist}/2 = (60\ mmHg \times 5\ mm)/2 = 150$, and:

$T_{prox\ Cylinder}/T_{dist\ Sphere} = 600/150 = 4$.

Hence, the compliance of the materials used to build the respective balloons needs to be adjusted according to their respective ratio of tension (T) created during balloon, inflation in order to induce occlusion of the arteries 41 vs. 26L (or 23L) with the compliance of the material representing the proximal balloon 38 being 4 times lower than the compliance of material representing the distal balloon 42. In other words, if a proximal balloon 38 is a cylinder, whereas a distal occluding balloon 42 is a sphere, and if a radius of a proximal balloon must be 2 times larger, than a radius of a distal balloon, then the compliance of a material of a proximal balloon 38 must be made 4 times lower, than a compliance of a distal balloon 42 in order to achieve a goal of synchronous, symmetrical and/or similar rate of occlusion of the respective arteries 41, 26L and/or 23L.

For example, if:

$C_{dist}/C_{prox} = 2 \times R_{prox}/R_{dist}$ and $R_{prox} = 10\ mm$, whereas $R_{dist} = 5\ mm$, then:

$C_{dist} = 4 \times C_{prox}$, i.e. the compliance of a distal balloon 42 will have to be 4 times higher (or the compliance of a proximal balloon 38 will have to be 4 times lower) to satisfy a requirement of a similar rate of expansion of both balloons, while inflated via the same channel.

In all other shapes and combination of shapes of the respective balloons, (such as cone, cube, capsule, rectangular tank, spherical cap, conical frustum, ellipsoid etc.) these compliance and tension ratios will be similar with the only difference of a coefficient K ($T_{dist} = K \times T_{prox}$ and $C_{dist} = K \times C_{prox}$) calculated specifically for each shape and size of a respective balloon combination.

In yet another embodiment the goal of synchronous rate of expansion of the proximal balloon 38 vs. distal balloon 42 during their inflation via the common channel 132 can be achieved on the basis of modifying the lumen of the inflation channel 132 at the different segments of the catheter shaft (FIGS. 6-D, 7-D, 8-D).

The inner diameter ($ID_1$) of the lumen of the common inflation channel 132 of the part of the catheter shaft extending from the proximal hub 130 to the level of inflation openings 58 of the proximal balloon 38 can be made smaller, than the inner diameter ($ID_2$) of the more distal segment of the inflation channel extending from the level distal to the most distal opening 58 to the level of distal balloon inflation openings 60 (FIGS. 6-D, 7-D, 8-D). As a result, according to the laws of hydraulics the amount of pressure per unit of the inflation channel surface of the narrow segment of the inflation channel 132 with a smaller diameter $OD_1$ will be proportionally less, than the pressure exerted on the wider distal segment of the inflation channel 132 that is connected to the distal balloon 42 via openings 60.

As a result, in spite of a smaller diameter and higher tension of the distal balloon 42 compared to balloon 38, it may inflate at a faster rate, and therefore may approximate and match the rate of expansion of a larger proximal balloon 38 that is inflated via a narrower portion of the inflation channel 132 having a smaller inner diameter ($ID_1$). In further embodiments, where the balloon material may be of a similar compliance, the propensity of a larger balloon 38 to expand faster while inflated via a common channel 132 may be mitigated and, adjusted to the rate of expansion of a distal balloon 42 by calculating the diameter, radius and/or volume ratios of respective balloons and using an inverse, ratio of said parameters in order to modify the ratio of inner diameters of the proximal vs. distal segments of the inflation channel and/or total area of proximal openings 58 in relation to the total area of distal openings 60 of the channel 132 with reference to FIG. 16. As shown in FIGS. 16, 16A and 16B has in inflation channel 132 with different widths. The inflation channel 132 has a diameter D1 within the entire longitudinal length of the proximal balloon 38, and a diameter D2 within the entire longitudinal length of the distal balloon 42. D2 is greater than D1. The ports 58, 60 could be the same size or they may be different in size such that port 58 is of a different diameter than port 60. The inflation channel 132 can be D1 in size in the segment 44 and in portion of the shaft 104 distal to the distal occluding balloon 42.

As it can be derived via equations of the Pascal Law of Hydraulics, fluid will go easier via a larger channel than via a smaller channel. For example, if the diameter, volume, or radius of a proximal balloon 38 is 2 times larger than the diameter, volume, or radius of a balloon 42, then the inner diameter $ID_1$, volume, or radius of the proximal segment 68 of the inflation channel 132 (FIGS. 6-D, 7-D) should be at least 1.5-2 times narrower, than the inner diameter $ID_2$, volume, or radius of the distal part of the inflation channel 132 and/or 70, 72 connected to the distal balloon 42 via openings 60.

In the single trans-aortic balloon embodiment (FIGS. 11, 13-15), where the distal portion of the balloon designated to occlude the left subclavian 23L and/or left carotid 26L artery this goal can be achieved by decreasing the maximal diameter of distal portion of the balloon to the diameter equal or slightly larger than the diameter of arteries 26L and 23L and by increasing compliance of this part of the balloon, while the compliance of the proximal segment of the balloon that is located in the innominate artery 41 and is designed to have a larger diameter would be made out of a less compliant material. Moreover, in some embodiments the compliance of the intermediate part of the trans-aortic balloon (the part Alpha that is designated to be positioned in the aortic arch adjacent to the ostium of the left carotid artery 26L to overlap this ostium and occlude the flow to the left carotid artery 26L may be made out of a compliant or a very compliant material in order to assure a full coverage of the orifice of the left carotid artery at minimal increase of intra-balloon pressure. (FIG. 11, 13-15).

Another embodiment that may reach a similar effect regardless of the values of compliances and volumes of the balloons—would be using a bifurcated common inflation channel that divides into subsequent 2 inflation channels with the channel leading to a larger proximal balloon 38 being proportionally larger than the channel leading to distal balloon 42.

Within the same context, if one desires to build a 2-ballon catheter, or any other, multiple balloon catheter with balloons being inflated via the same port 130 and same channel 132, but if at the same time one desires to obtain the inflation of the distal balloon to happen earlier and at lower inflation volumes, one may use a more compliant material for a distal balloon 42 and less compliant material for a proximal balloon 38, and/or larger volume of the distal balloon 42 compared to the volume of the proximal balloon 38.

Another embodiment would comprise a Y-connector 138 (FIGS. 5-A, 5-D) with the common single hub 138 for 1 syringe or any other source of inflation or injection, divided into at least 2 arms 134 and 136 and releasably attached to a balloon catheter via at least two of the ports 46, 48, 130 or 50 (FIGS. 5-A, B, C) and their respective inflation channels 68, 72, 132 or 70 with the main goal of achieving a synchronous inflation of all occluding balloons using a single inflation source and inflation port (FIGS. 5-A and 5D). This embodiment will solve the problem of, a "one-hand" simultaneous inflation and/or deflation of all balloons simultaneously via one single syringe or inflation/deflation source creating an advantage of performing this procedure in a much quicker and organized fashion, rather than inflating and deflating each balloon sequentially one after another, the process, which would take a much longer time.

FIG. 5-A shows the Y connector 138 with arms 136, 134 disconnected from the ports 46, 48 but it is to be understood that it can be connected so that arm 136 is attached to and in fluid communication with port 46, and arm 134 is attached to an in fluid communication with arm 48. Inflation pressure into the single port of Y connector 138 will then push inflation fluid into both arms 134, 136 and through ports 46, 48 to inflate the balloons. FIG. 5-D likewise shows the Y connector 138 detached from the ports 50 and 130 but could be attached to thereto so that arm 136 is in fluid communication with port 50 and arm 134 is in fluid communication with port 130. This causes inflation through a single port of the Y connector 138 to cause inflation fluid to simultaneously flow through both ports 50, 130 and inflate the balloons 38, 42 at the same time. The Y connector 138 although not shown in FIGS. 5-B and 5-C could be present and likewise attached in these embodiments, and in other embodiments herein, to effect simultaneous inflation and deflation of the balloons 38, 42.

A distal occluding balloon 42 may be smaller and more compliant than a proximal occluding balloon, whereas a proximal occluding balloon may be larger and less compliant than a distal occluding balloon, achieving the goal of more synchronous rate of their expansion during their inflation via a single, combined, or common inflation channel 70, 72, 68 and/or 132.

The degree of compliance, degree of inflation and the sizes of the balloons may be proportionally related and adjusted to achieve a desired ratio leading to the most adequate and simultaneous inflation of the proximal balloon to occlude the innominate artery 41 and the distal balloon to occlude the left carotid artery 26L, using a single source of inflation, a common inflation source and a common or interconnected inflation channel.

The occluding balloons 38, 42 may be inflated to such a pressure and be of such a compliance and/or resiliency that they completely block any blood flow past them and through the particular artery or arteries into which they are positioned. However, it is to be understood that other arrangements are possible in which some amount of blood may flow past the proximal occluding balloon 38 and/or the distal occluding balloon 42.

FIG. 4-A illustrates the flow of blood in the circulatory system upon inflation of the proximal and distal occluding balloons 38 and 42. Temporary interruption of flow at the level of the proximal carotid arteries 26R, 26L leads to divergence of blood flow 35 carrying all potential cerebral emboli 28 into the descending aorta 24. Emboli 28 diverted from cerebral circulation move through the descending aorta 24. The proximal occluding balloon 38 may completely block the innominate artery 41 so that no blood flow or emboli 28 may be transferred through the right carotid artery 26L and the right subclavian artery 23R. The position of the proximal occluding balloon 38 can be made so that it is right at the bifurcation of the innominate artery 41 in order to completely occlude the orifice of the right carotid 26R and right subclavian 23R arteries at the same time.

FIG. 4-B shows another version of the catheter 108 in which the proximal and distal occluding balloons 38, 42 when expanded are not spherical in shape. In this regard, if inflated without restriction by the arteries or another member, the proximal and distal occluding balloons 38, 42 would not be a sphere but would be an object with one end wider than another end. The proximal occluding balloon 38 has a proximal portion 38-P that has a smaller diameter than a distal portion 38-P which would thus have a larger diameter. If not in a shape that would exhibit a diameter, then the proximal portion 38-P is not as wide (is more narrow) than the distal portion 38-D. The width can be measured as the lateral distance of the proximal occluding balloon 38 perpendicular to the shaft of the catheter. When positioned within the patient, the proximal portion 38-P is proximal the distal portion 38-D and could be within the innominate artery 41 while the distal portion 38-D is within the ostium of the innominate artery 41. The distal occluding balloon 42 is not a sphere but instead has a portion that is wider than another portion. The distal occluding balloon 42 has a distal portion 42-D with a smaller width than the width of the proximal portion 42-P. When positioned within the patient, the distal portion 42-D may be within the left carotid artery 26L, and the proximal portion 42-P is within an ostium of the left carotid artery 26L.

Figure 4C:
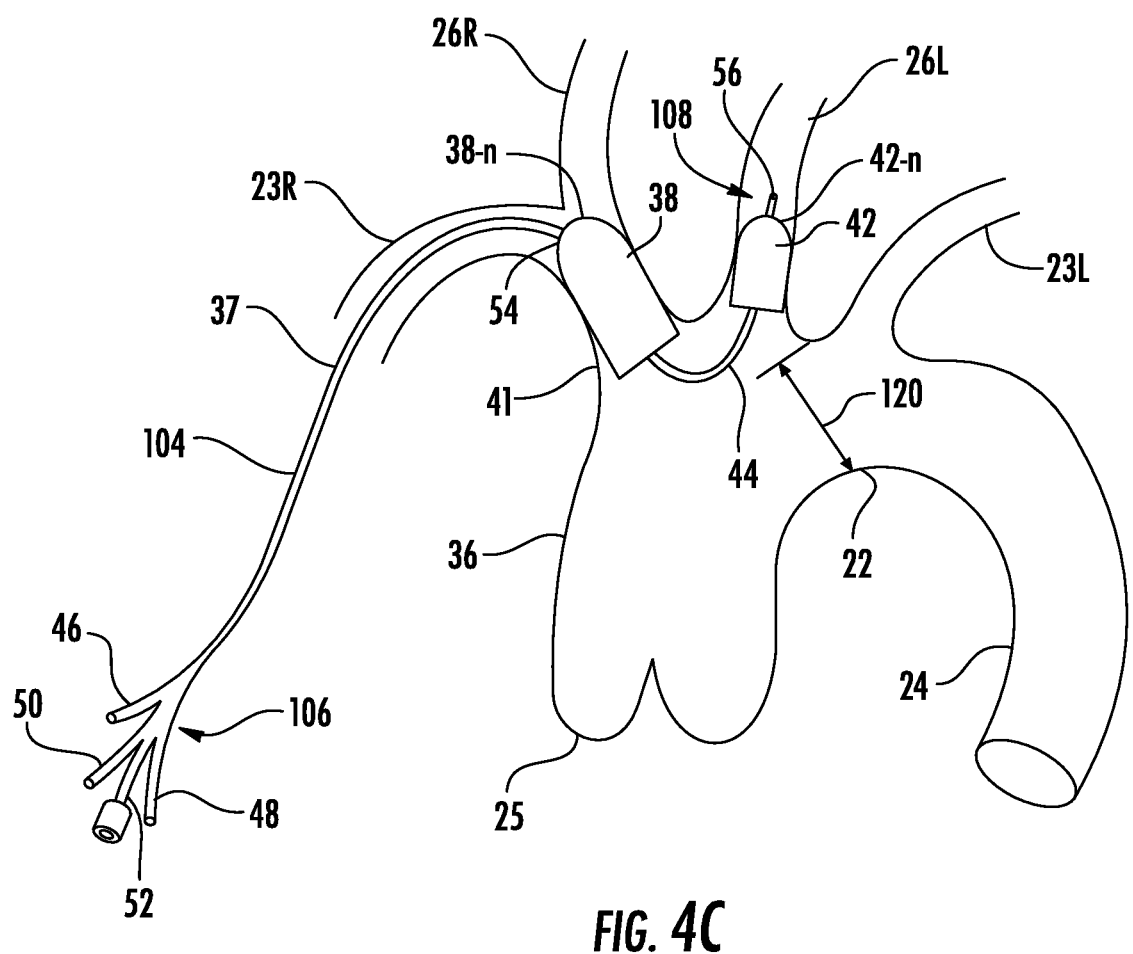

FIG. 4C shows another embodiment in which the proximal occluding balloon 38 is cone shaped. A nose 38-N has a smaller diameter than the distal portion of the proximal occluding balloon 38, and has a smaller diameter than the center portion of the proximal occluding balloon 38. The nose 38-N is positioned within the innominate artery 41, and the larger diameter distal portion of the proximal occluding balloon 38 is at the ostium of the innominate artery 41. The distal occluding balloon 42 when inflated without restriction by an artery is in the shape of a cone. The nose 42-N has a smaller diameter than the center of the distal occluding balloon 42, and has a smaller diameter than the proximal end of the distal occluding balloon 42 opposite to the nose 42-N. When positioned within the patient, the nose 42-N is within the left carotid artery 26L and the end/base is within the ostium of the left carotid artery 26L.

Both distal and proximal occluding balloons 38, 42 are inflated just before proceeding with the part of the procedure prone to generate cerebral emboli 27. This may be the placement or removal of an aortic cross clamp, implantation of valves, endovascular grafts and stents, or other procedures outlined above. The balloon pressure required to completely interrupt flow in carotid arteries 26R, 26L at this point of intervention is usually significantly less and rarely exceed 50-60 mm of mercury. This consideration is based on the fact that the physician may bring the systemic perfusion pressure of the patient to minimal levels at this particular time of the procedure that involves the emboligenic event. Therefore, the occluding balloon 38, 42 pressure required to occlude carotid arteries 26R, 16L at this short period of time can be significantly lower and less damaging to the carotid arterial walls 26R, 26L.

Inflation of the occluding balloons 38, 42 can be such that they are inflated to a pressure exceeding the patient's systemic pressure by 10-20 mm Hg or more just before proceeding with the emboligenic part of the procedure. Adequate occlusion of the carotid arteries 26R and 26L will lead to a known phenomenon of a temporary reduction of flow through vertebral arteries leading to additional divergence of blood and emboli 28 away from both vertebral arteries. This will decrease the risk of stroke in vertebrobasilar circulation. Insertion of the occluding catheter 37 through the right side and inflation of the proximal occluding balloon 38 at the level of the innominate artery 41 may preclude entrance of emboli 28 into the right subclavian artery 23R and right vertebral arterial system. Insertion of the occluding catheter 37 through the left side of the patient may cause the proximal occluding balloon 38 to be at the level of the left subclavian artery 23L to preclude entrance of emboli into the left subclavian artery 23L and vertebral arteries, further reducing the risk of emboli entrance and stroke. Moreover, insertion of a single trans-aortic balloon through both the innominate artery 41 and left subclavian artery 23L, while overlapping the orifice 92 of the left common carotid artery 26L by the mid-portion of this balloon would prevent the entry of emboli into both carotid and vertebral arterial systems (FIGS. 13-15).

The distal and proximal occluding balloons 38, 42 may be deflated 30-90 seconds after this part of the procedure is completed to achieve complete washout of all potential emboli 28 into the descending aorta 24 and distal vasculature, while avoiding migration of emboli 28 into the carotid arteries 26R and 26L. This timing, however, can be either shortened or extended depending on multiple factors that comprise the timing of embolic events, their intensity and the degree of patient's tolerance to transient interruption of cerebral flow such as the degree of hypothermia and the condition of the collateral cerebral flow as measured by EEG, transcranial Doppler, or other means.

The length of most manipulations associated with formation and transgression of emboli into cerebral circulation rarely exceed 1-2 minutes. Temporary interruption of the carotid flow for this period of time, plus 0.5-1.5 min to allow for complete washout of emboli 28 from the aorta 22 is completely safe and feasible.

Partial deflation of said balloons may provide necessary blood flow to the brain while still decreasing the degree of cerebral embolization. Said technology will extend the length of cerebral protection from embolic stroke while assuring continuous cerebral perfusion.

Once the emboligenic procedure is completed both occluding balloons 38 and 42, and/or a trans-aortic balloon, depicted in FIGS. 13-15, may be deflated. Optionally, repeating the whole process of cerebral protection may be conducted if desired once a brief period of cerebral reperfusion is reached. The procedure can be repeated at any time of surgery and on multiple occasions when the emboligenic intervention is anticipated. Upon completion of the main surgical procedure, the occluding catheter 37 can be completely removed or pulled back completely into the right subclavian artery 23R or left arm arteries, including the artery 26L for later removal.

FIGS. 5-8 illustrate an exemplary embodiment of the occluding catheter 37 as being a 2-balloon catheter 37, containing either 1, 2, 3, 4 or more lumen paths and/or and channels depending on the type of the embodiment. The occluding catheter 37 includes a shaft 104 that may have an outer circumference that is circular in cross-sectional shape. However, other cross-sectional shapes of the outer circumference are possible in accordance with other exemplary embodiments to such an extent that the volume, compliance, shape and sizing parameters, of each balloon may be varied and/or adjusted to similar parameters of another balloon, depending on the balloon compliance and surface tension created during inflation to a radius of 10 mm for a proximal balloon 38 and a radius of 5 mm for a distal balloon 42. Ports 46, 48 and 50, 130, 134, 136, 138 may have openings at their extreme proximal ends to allow for communication with their respective channels 68, 70, 72, 132 and can have fittings configured to receive inflation syringes, pressure measurement devices, guide wires 100 and 142, pressure wires to measure pressures at different segments of the catheter, comprising, the area of the tip 56, the inter-balloon segment 44 and the area proximal to the proximal balloon 38 or other components. In addition, the proximal openings of ports 46, 48 and 50, 130 may allow for communication with a Y-type connector 138 or a similar multichannel connector 138 having more than 2 arms for unifying all inflation port to a single inflation channel 138 for a synchronous simultaneous inflation, of all balloons through all connected channels (FIGS. 5-A, 5-D, 6-A, 7-A, 8-A).

Channels 68, 70, and 72 and/or 132 have circular cross-sectional shapes and may be connected at different levels of the shaft to assure a simultaneous inflation of the balloons via a corresponding inflation port. These channels can be of a different diameter $ID_1$ and $ID_2$ with a larger diameter leading towards the larger proximal balloon 38 and a smaller diameter $ID_2$, continuing to the distal balloon, or vice versa depending on the goal of the occlusion catheter. For example, in order to achieve the synchronous occlusion of the larger artery 41 and a smaller artery 26L all, or some of the respective channels 68, 70, 72 and/or 132 can be connected (FIGS. 6-C, 7-C; 9-A, B, C and 10-A, B, C). Moreover a portion of the inflation channel responsible for inflation of the proximal balloon 38 may be narrower (having a smaller diameter $ID_1$) than the distal portion of the inflation channel (having a smaller diameter $ID_2$) responsible for inflation of a distal balloon 42 (FIGS. 6-D, 7-D, 8-D), hence increasing the inflation rate of a smaller and less compliant distal balloon and downregulating the inflation rate of a larger and more compliant proximal balloon 38 in order to a achieve a goal of a most even and uniform rate of balloon expansion and vessel occlusion.

In other arrangements the cross-sectional shapes may be different, their diameters can be the same or variously sized such that they are, not the same size as one another and their arrangement and inner diameter (ID) along the course of the catheter may vary. For example, in some embodiments the arrangement of channels may be coaxial with a larger peripheral or central channel assigned for inflation of the proximal balloon 38 and/or distal balloon 42, depending on the balloon size, compliance of the balloon material, its shape and volume). However, in other embodiments (FIGS. 6, 7, 8) the guidewire channel may be central and larger or equal in total cross-sectional area to the remaining one or two channels used for inflation of the proximal and distal balloons. Moreover in some embodiments the channels may be positioned as stacked one on top of another or next to each other, depending on the structural characteristics of the catheter, its primary, secondary and tertiary curves and materials. In addition, said channels may connect or represent a single channel at various segments of the catheter or throughout most of its length to decrease the diameter of the catheter and to decrease its profile in order to facilitate its insertion into a smaller access artery (such as radial artery) and through a smaller sheath.

The channels 68, 70 and 72 and/or 132 may be in fluid communication with one another or represent a single channel 132, or a double channel 70-72, or any combination of channels 70, 72, 68 and 132 at various segments of the catheter or throughout most of its length for the reason of decreasing the outer diameter of the catheter and to increase the overall cross-sectional area of the inflation channel(s) and/or channel 70 (1 or 2) of a guidewire 142 to achieve a faster inflation or injection rate and faster deflation or aspiration of the media used for this purpose (such as AIR, $CO_2$, Helium, Saline, Contrast Dye or any other media and in any combination thereof). The proximal and distal occluding balloons 38, 42 may be inflated separately from one another such that one is inflated before another one, or such that both inflate simultaneously. Pressure of inflation supplied by a pressure supply 126 may be to a degree greater than the patient's systemic arterial pressure at the time of inflation and may be arranged to self-adjust automatically on the basis of pressure sensors and/or pressure measurement channels throughout the different segments of the catheter. The pressure inside the occluding balloons 38, 42 may exceed only minimally the patient's systemic and carotid arterial 26R, 26L pressures with the goal to achieve complete interruption of the antegrade carotid flow without undue trauma to these vessels 26R, 26L.

Proximal and/or distal occluding balloon inflation port 46 and/or 132 may be in fluid communication with the proximal occluding balloon channel 68. The channel 68 may not terminate at the proximal occluding balloon 38 and may extend past the proximal occluding balloon 38 in the distal direction and be in fluid communication with balloon 42. Moreover, the channel 68 and/or 132 may have a different inner diameter (ID) throughout its course with the part of the channel extending from port 46 to proximal balloon openings 58 being, narrower (diameter $ID_1$), than the part of the channel starting distal from openings 58 and extending to the level of distal balloon openings 60 (diameter $ID_2$), i.e.: $ID_1 < ID_2$. This arrangement would facilitate a more expeditious filling of a smaller distal balloon 42 in order to match the rate of expansion of a larger proximal balloon 38. In some instances, as used herein the rate of expansion may refer to the percentage of total volume of the occluding balloon that is filled. As such, if the proximal and distal occluding balloons 38, 42 have different volumes and sizes they will share the same rate of expansion if at the same point in time one is 50% full by volume and the other is likewise 50% full by volume. The value of ratio $ID_1/ID_2$ must be set to assure a synchronous filling of both balloons in spite of their different sizes, diameters and compliances. A similar goal of achieving a synchronous expansion of balloons 38 and 42, when inflated via a common channel may be achieved by varying the total area of balloon inflation openings for the proximal balloon 38 vs. the distal balloon 42. In this case, the total area of openings 58 that are responsible for inflation of a larger proximal balloon 38 may be diminished in relation to the total area of openings 60 responsible for inflation of a distal balloon 42 to the extent that the force of inflation for both balloons would be balanced against their compliances and diameters. For example, if the total area of inflation of the proximal balloon 38 via openings 58 ($A_{prox}$) is 0.25 mm² and the total area of inflation of the distal balloon 42 via openings 60 ($A_{dist}$) is 1.00 mm², than according to the Pascal's law:

$$F_{prox} = PA_{prox} \text{ and } F_{dist} = PA_{dist},$$

where F—force of inflation applied to the balloon via proximal openings 58 or distal openings 60 and P—pressure inside a common balloon inflation channel 132 and/or 68 that is equal for proximal and distal balloons, then:

$$F_{prox\ Opening}/F_{dist\ Opening} = PA_{prox\ Op.}/PA_{dist\ Op.} = P \times (\pi R^2_{prox\ Op.})/P \times (\pi R^2_{dist\ Op.}) = R^2_{prox\ Op.}/R^2_{dist\ Op.}$$

In other words: the ratio of the inflation force via a total area A of the proximal balloon openings 58 to distal balloon openings 60 will be equal to the ratio of the squares of the total sum of diameters of these openings, i.e.:

$$F_{prox\ Op.}/F_{dist\ Op.} = R^2_{prox\ Op.}/R^2_{dist\ Op.}$$

Similar calculation may be used for determining the optimal ratio of inner diameters ($ID_1$ vs. $ID_2$) of the proximal segment of the inflation channels 68 or 132 ($ID_1$) and their distal segment responsible for inflation of a distal balloon ($ID_2$), i.e.: $F_{prox\ Channel\ Diam\ OD1}/F_{dist\ Channel\ Diem\ OD2} = R^2_{prox\ Chan.\ OD1}/R^2_{dist\ Chan.OD2}$ According to these formulas, if the total area A of inflation openings 58 vs. 60 is equal, then the force of balloon inflation F for both balloons would be also equal:

$$F_{prox\ Op.}/F_{dist\ Op.} = 1 \text{ i.e. } F_{prox\ Op.} = F_{dist\ Op.}$$

In addition, in some embodiments, one or more openings 58 and/or 60 may extend through the shaft 104 in order to place the channel 68 and/or 132 into fluid communication with the interior of the proximal occluding balloon 38 and/or a distal occluding balloon 42. Fluid pressure supplied by a syringe or other source may be introduced through port 46, channel 68 and/or port 130, channel 132 and out of openings 58 and/or 60 in order to inflate the proximal occluding balloon 38 and out of opening 60 to inflate the distal balloon 42 to their inflated state. In addition, in some embodiments, where the simultaneous inflation of both balloons 38 and 42 through a common channel 132 is desired, the goal of obtaining a similar rate of inflation for both balloons, in spite of differences in balloon volumes and/or compliances, can be achieved by adjusting the number and/or sizes of openings 58 and/or 68. For example, for a larger proximal balloon 38, the number and total openings' area of openings 58 may be proportionally less than the respective parameters of holes 60 in a distal balloon 42. As a result, the rate of expansion of the larger proximal balloon 38 will be adjusted and/or downregulated to the rate of expansion of the smaller distal balloon 42, thus achieving a synchronous expansion and deflation of both balloons while they are actuated via the common channel 132 and/or communicating channel 68.

Figure 20A:
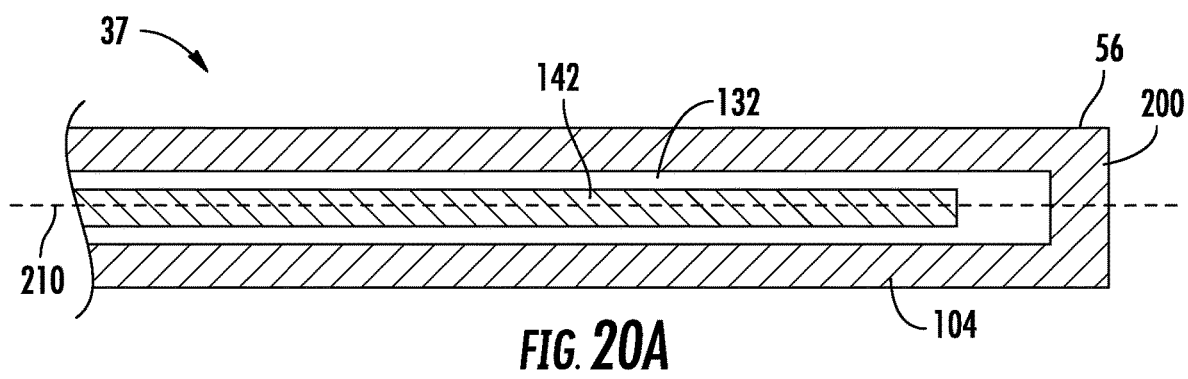
FIG. 20A is a cross-sectional view of a tip of the shaft with a closed occluding mechanism.
Figure 20B:
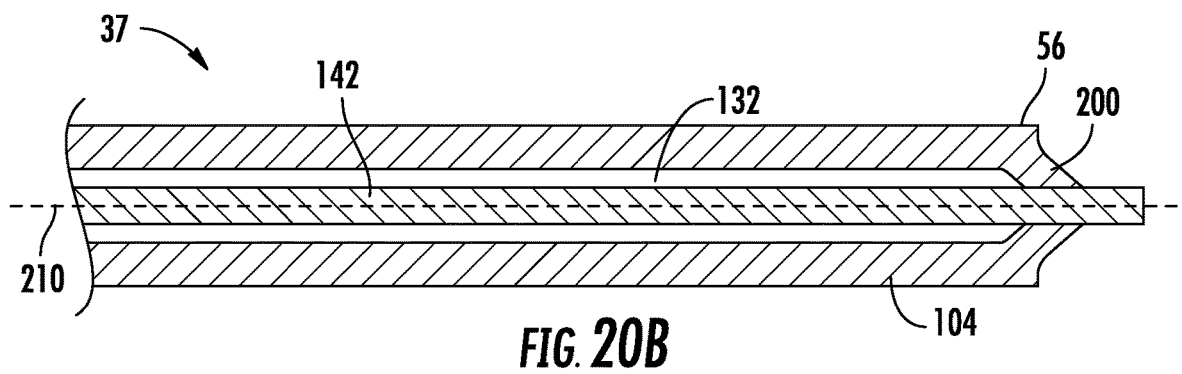
FIG. 20B is a cross-sectional view of the tip of the shaft of FIG. 20A but with the guidewire passed through the occluding mechanism and a seal still in place.

In order to decrease the catheter profile and minimize the number of catheter channels inside the shaft 104, and especially in the segment 44 and the areas of occluding balloons 38 and 42 the occluding catheter may be constructed with its common channel (comprising a balloon inflation channel and a guidewire channel) having an occluding mechanism 200 (as shown in FIGS. 20A and 20B) at the distal tip 56 of the catheter. Such mechanism may be a diaphragm, valve, overlapping stretchable thickening that would let the guidewire 142 through, but would not let the seepage of air or fluid to occur through it Such a mechanism 200 can be made out of compliant protuberations having smooth semioval, oval, round or any other shape of the material of the inner lumen 132 of the catheter 37 that allow for a passage of a one or two guidewires 100, 142 while congruently surrounding the surface of the guidewire 100, 142 thus recreating the seal, and then being able to re-close on themselves after the wire is withdrawn, thus allowing for inflation of occluding balloons through the common inflation/guidewire channel 132 with or without guidewire 100, 142 in place. In FIG. 20A the occluding mechanism 200 is closed and the channel 132 is sealed at the distal tip 56 so that fluid cannot flow through this opening. Pressure from the guidewire 100, 142 distal forces it through the occluding mechanism 200 so that it moves distal to the distal tip 56 as shown in FIG. 20B. The occluding mechanism 200 is urged through its own resiliency against the guidewire 100, 142 to seal it when the guidwire 100, 142 is distally disposed so that a fluid seal likewise exists in this configuration as well. Retraction of the guidwire 100, 142 causes the occluding mechanism 200 to spring back into the FIG. 20A position once the guidewire 100, 142 is not, against the occluding mechanism 200. The occluding mechanism 200 may be made out of the same material as the shaft 104 and can be integrally formed with the shaft 104. Alternatively, the occluding mechanism 200 can be a different material than the shaft 104 and may be a separate piece attached thereto. The occluding mechanism 200 can be any type of component capable of opening and closing such as a valve, flap, or protuberances of the shaft 104 that extend inward.

Such an occluding guidewire 142 and/or 100, where some segments such as a distal segment, or at least 1 segment of a guidewire, may have one or more areas of wider diameter of a guidewire congruently matching the inner diameter ($ID_2$ and/or $ID_2$) of the corresponding segment of the catheter shaft, wherein such thickenings are able to obstruct the distal ostium of the catheter (or its other segment) to achieve inflation of the balloon(s) via the same guidewire-inflation channel without leakage of fluid or gas and air through the distal ostium 56, or other openings 54, 58, 60, 144 of the catheter 37 when they are occluded by the corresponding thickenings on the occluding guidewire 142 with the main goal being an inflation of the occluding balloon via the guidewire 142 channel without spillage of air or fluid via distal or any other ostia, when the thickening is tightly approximated to the area of openings of the catheter that are not designed for balloon inflation. Hence a new method of catheterization and protection from emboli of the aortic arch branches 41, 26L and/or 23L may be used, wherein a guidewire 142 in its embodiment containing the occluding thickenings, may be first inserted into the target artery via a larger standard catheter, where the catheters inner diameter is equal or larger to the outer diameter of the thickenings of the guidewire, and then this catheter is removed and the disclosed balloon catheter 37, comprising a narrower single or double channel, which inner diameter is equal or less then the outer diameter of the thickenings of the guidewire, is inserted.

In order to use the balloon inflation channels (or both channels) for partial insertion of the guidewire 142 one must make sure that these channels would accept a guidewire 142, i.e. the inflation channel of the proximal and/or distal balloons must be equal or larger than the diameter of a guidewire 142 used for insertion, unless a monorail system is used.

Figure 9A:
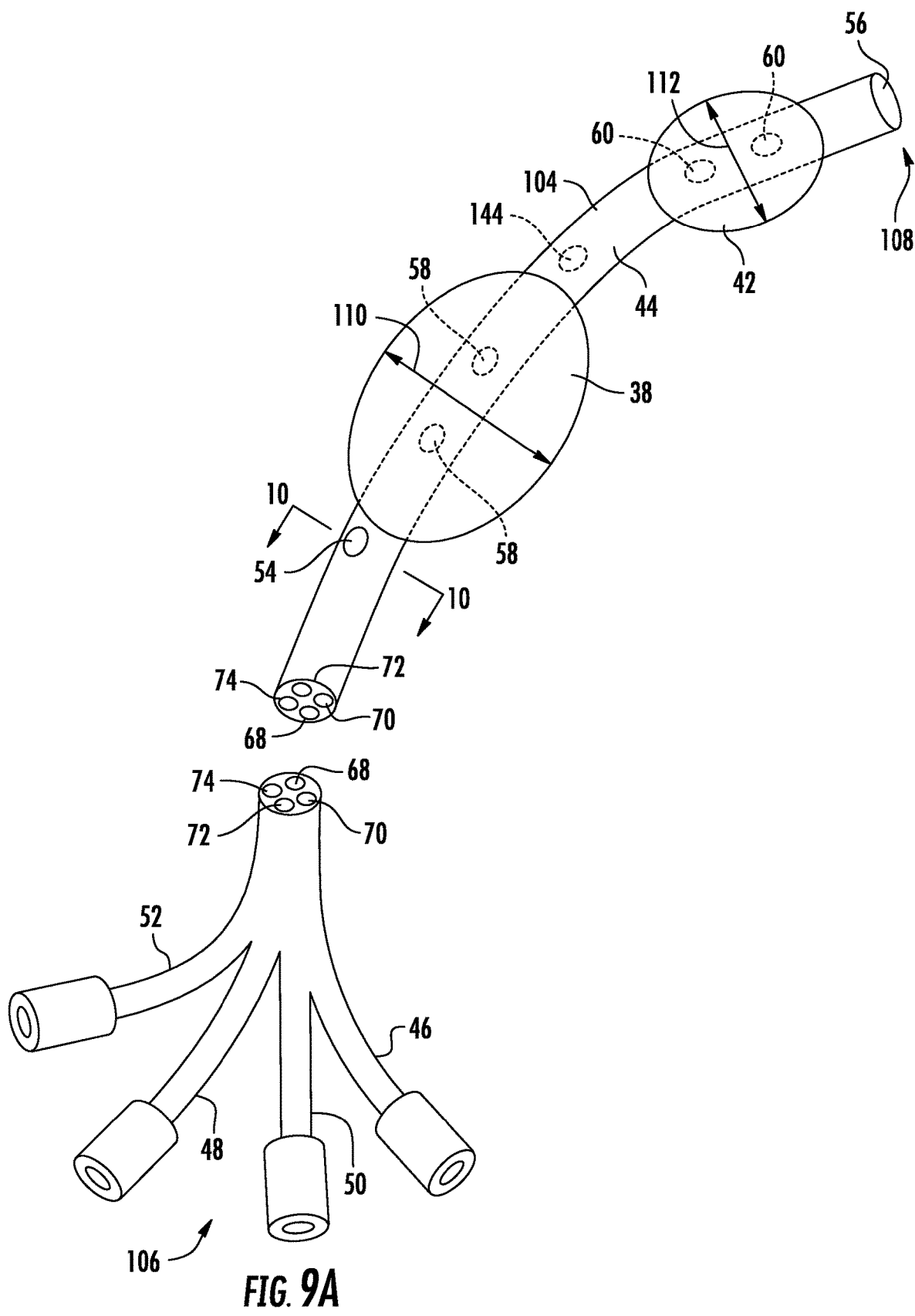
FIG. 9-A is a perspective view of the occluding catheter of FIG. 5-A in an inflated state with a section cut away to view interior portions.
Figure 9B:
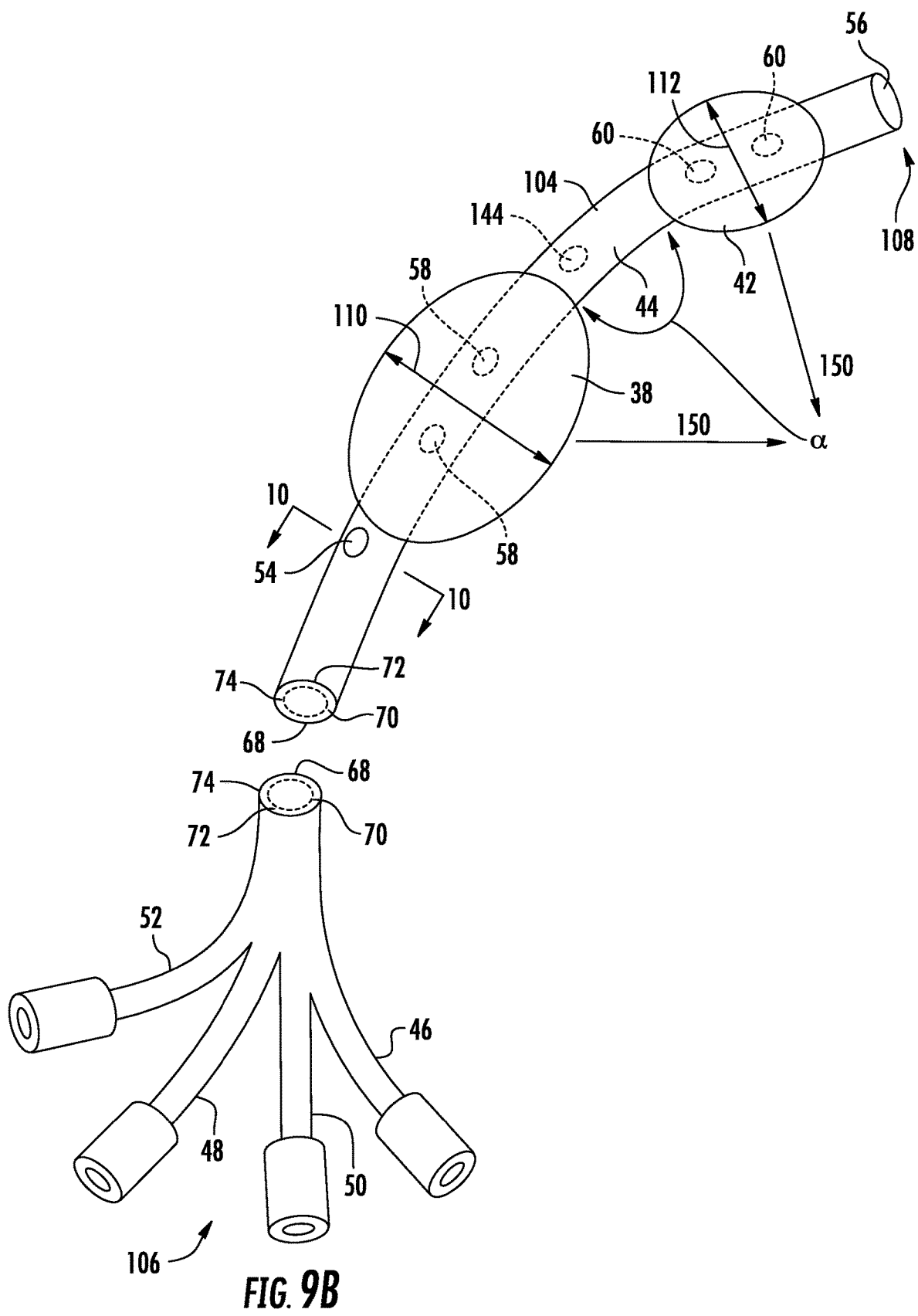

On the other hand, the distal 40 mm-60 mm portion of the catheter: segment 44 (average 30 mm, range 20-60 mm), distal balloon (average 15 mm, range 5-52 mm) and the catheter tip (average 5 mm, range 0-25 mm) will also have a two-lumen configuration: one lumen for inflation of a distal balloon and $2^{nd}$ lumen—for Insertion of a monorail guidewire 142 via an opening 144 in the proximal segment of the inter-balloon portion 44 of the catheter shaft 104 (FIG. 9-A).

Another embodiment permitting minimization of the outer diameter and the external profile of the occluding catheter, allowing its insertion via small peripheral arteries such a radial or ulnar, or brachial artery may be a catheter, where there is a wire channel that starts distal to the proximal balloon 38 at the opening 144 (FIGS. 5-C, 9-A) at the beginning of segment 44 and proximal to the distal balloon 42 (FIGS. 5-C, 9-A), having a monorail configuration. This embodiment would achieve, several goals, such as decreasing the diameter of the catheter shaft, proximal to the area of the inter-balloon segment 44, assisting the process of distal flexion of the distal portion of the catheter (segment 44) by gentle pulling on a monorail guidewire and augmenting the intrinsic strength of the segment 44 and the further distal portion of the catheter, including the area of a distal balloon 42 and catheter tip 108 with a distal part 56 in order to facilitate the catheter insertion (FIG. 4). Such monorail guidewire channel may start at the intermediate pressure measurement channel opening 144 of segment 44, or a proximal pressure measurement channel orifice 54 (FIG. 9-A) and end at the distal catheter tip orifice 56 (FIG. 9.-A) and be present in addition to a guidewire channels 132 or 70, where one, two or more guidewires could be used to facilitate the process of catheter insertion, manipulation and positioning. A monorail channel for the guidewire 142 may be created starting at the distal portion of the proximal balloon (opening 144, 40 mm-60 mm from the catheter tip) and exiting trough the distal end opening 56 of the tip of the catheter 108. This feature would achieve a goal of minimizing the number of channels in a more proximal part of the catheter 37, including the part carrying the proximal balloon, and creating a two-lumen or a single lumen catheter that will have a smaller profile than its 3-lumen counterpart. Moreover, as the bulkiest portion of the catheter would be the area of a large proximal balloon 38, this solution would allow to decrease the outer diameter of the catheter shaft carrying balloon 38, thus decreasing its profile and the size of the vascular introducer sheath, needed for its insertion. On the other hand, the distal 50 mm portion of the catheter (average length 50 mm, range 40-60 mm), segment 44 (average length 30 mm, range 20-60 mm), distal balloon (average length 15 mm, range 5-25 mm) and the catheter tip (length 5 mm, range 0-10 mm) may also have a two-lumen, or one-lumen configuration, where one lumen is dedicated for the insertion of a monorail guidewire and the other lumen is used for inflation of a distal balloon 42.

The proximal occluding balloon 38 may be connected on its distal and proximal ends to the shaft 104 and inflation pressure will cause the proximal occluding balloon 38 to expand so as to have a circular cross-sectional shape. The proximal occluding, balloon 38 may have other longitudinal cross-sectional shapes in other exemplary embodiments such as spherical, oval or elliptical. The occluding balloon 38 may be variously shaped and sized in accordance with different exemplary embodiments. The size and shape of the balloon 38 may be equal or approximately larger than the size and shape of the innominate artery in each particular patient as determined by computerized scanning and/or angiography to achieve an optimal, most effective and atraumatic occlusion of the artery without undue stretching and intimal injury. The proximal occluding balloon 38 may be coaxial with the shaft 104, whereas the shape of the shaft of the catheter may have primary, secondary and tertiary curves aimed at achieving a coaxial position of the balloon 38 in relation to the innominate artery, when the lateral walls of the balloon may occupy are congruent to the shape and curve of the innominate artery, where the balloon is inflated. In accordance with various embodiments, the proximal occluding balloon 38 may be coaxial with the channel 70, 72 or 68. In other embodiments the proximal occluding balloon 38 is not coaxial with the shaft 104 or any of the channels 70, 72 or 68.

In order to achieve a desired degree of flexion of the secondary catheter curve Alpha (angle α on FIGS. 2, 3, 4, 5-A, B, C, D) that may be required to be between 160 and 220 degrees in relation to the more proximal segments of the catheter shaft, the balloon 38 and or 42 may be attached to the catheter shaft 104 further into the segment 44 in such a way that its expansion would lead to further flexion of the catheter shaft, comprising segment 44, in the direction of the secondary curvature Alpha (angle α) along the vector forces 150 (FIGS. 5-C and 5-D). This method will facilitate obtaining a desired degree of flexion of the distal part of the catheter by virtue of varying the degree of flexion (angle Alpha) with the help of an adjustable degree of a balloon expansion in order to position the catheter distal part 108 and its tip 56 against the ostium of the left carotid artery 26L or left subclavian artery 23L with subsequent advancement of one, or two guidewires 100, 142 into these arteries and/or direct advancement of the tip of the catheter into the artery 26L or 23L, using a pull-back technique by pulling the shaft of the catheter 37 back, thus promoting the wireless entry of the catheter tip into the orifice 92 of the left carotid artery 26L.

The process of flexion of the catheter by virtue of expansion of the proximal balloon 38 and/or distal balloon 42 in the direction of forces 150 (FIGS. 5-D, 9-B) may be achieved by mounting at least one of the balloons in an asymmetrical way (i.e. non-coaxial with the axis of the shaft of the catheter being shifted towards the catheter angulation, leaving a higher balloon volume outside the curve alpha, or vice versa), leading to uneven tension on the catheter shaft during the balloon expansion and resulting in catheter flexion. In addition to a non-coaxial mounting of the balloon to the catheter shaft, such uneven distribution of the forces 150 applied to the catheter shaft during the balloon expansion could be achieved by some degree of twisting the balloon around the long axis of the catheter shaft 132 in the area of a segment 44 by 15-180 degrees. Such twisting would create circular forces and tension lines 148 (FIG. 5-C) leading to flexion of the adjacent segment of the catheter shaft with the degree of flexion proportional to the degree of balloon inflation. As a result the physician will be able to tailor the degree of the catheter flexion by changing the degree of the balloon expansion in order to achieve a desired positioning of the distal segment of the catheter 108 and its distal tip and/or opening 56 right against the desired target vessel 26L or 23L. Similar modifications can be applied to the distal balloon 42 in order to affect an angle Gamma (γ) and therefore further improve the maneuverability of the distal segment of the catheter to facilitate the process of catheterization.

Other disclosed ways of achieving the goal of the catheter flexion during balloon expansion would be creating a balloon with asymmetrical ability of the balloon material to stretch with the area of the balloon on the side of required flexion of a radius $R_1$ being less compliant than the opposite and/or other areas of the balloon (FIGS. 5-C, 5-D). In this case with balloon inflation, the less compliant area of the balloon will stretch less, while the opposite area (facing away from the required angle of flexion) would stretch less and therefore leading to flexion of the catheter shaft in the direction of the less compliant balloon area. Such "less compliant" area may be incorporated into the surface of the balloon as a straight and/or curved line or spiral being between 20% and 150% of the balloon length and circumference, and if needed, rolling around the balloon surface in a spiral fashion. As a result the further the balloon is expanded, the more flexion of the adjacent portions of the shaft is achieved. In FIG. 5-D reference number 151 is a more compliant section of the distal occluding balloon 42 so that upon inflation the tip will bend so as to reduce angle gamma and bend towards the angle alpha/inwards towards the point R1.

Similar effect can be obtained by attaching the proximal and/or distal balloon in, a non-coaxial (eccentric) position in relation to the long axis of the catheter shaft so the larger volume of the balloon during its expansion is located on the opposite side of the required angle of flexion. In this case the larger portion of the balloon, i.e. the portion with a larger radius of the balloon surface will expand more in the direction 148, than the area of a smaller radius $R_1$ that will expand less in the direction 168 (FIG. 5-C) according to the Laplace's law. As a result the catheter shaft will flex towards the balloon area of a smaller radius $R_1$ and a smaller degree of the balloon expansion in the direction 150 (FIGS. 5-C and 5-D). Some of the embodiments may comprise one, two, or more of the mentioned features to achieve a desired effect. In addition, the goal of decreasing the profile (outer diameter) of the occluding balloons in order to facilitate their insertion via a smallest possible vascular sheath and/or vessel can be achieved by stretching occluding balloons along the catheter shaft by 5%-55% depending on their compliance and other material characteristics to decrease their bulky appearance and/or excessive outer diameter upon deflation, which is possible especially in balloons of a high or very high compliance. The stretching of the balloons may be between 5 and 55% of the non-stretched length of the balloon and can be combined with a 5-65 degree twisting in the direction 150 (FIG. 5-D) of the balloon 38 and/or 42 at 0-30 degrees in relation to its longitudinal axis as described above.

The shaft 104 continues in the distal direction past the proximal occluding balloon 38 and channels 70 and 72 may be present past the proximal occluding balloon 38. The distal occluding balloon 42 is located at the distal end 108 of the shaft such that a segment 44 of the shaft 104 is present between the occluding balloons 38, 42 to space them from one another. The distal occluding balloon channel 72 extends from the common occluding balloon inflation port 46, 47 or 48 and terminates at an opening 60 of shaft 104. The distal occluding, balloon channel 72 may be in fluid communication with the proximal occluding channel 68, and/or a guidewire channel 70. The distal occluding balloon 42 is attached at its proximal and distal ends to the shaft 104 and is inflated via pressure supplied through port 48 and/or port 46, channel 72 and/or 62 out of opening 60. It may also be expanded via a common port 130 and/or 138 and via the common channel 132. A single opening 60 may be present, or a plurality of openings 60 may be present through which pressure can be supplied to inflate the distal occluding balloon 42. As discussed above, the number of openings 60 and their total area $A_{dist\ Op.}$ may exceed the number and the total area $A_{prox\ Op.}$ leading to the proximal balloon 38 in order to balance out, the rate of expansion of both balloons during their inflation via a common channel. The distal occluding balloon 42 may have a circular cross-sectional shape, although other cross-sectional shapes are possible in other exemplary embodiments. The longitudinal length of the distal occluding balloon 42 may be less than that of the proximal occluding balloon 38. However, their longitudinal lengths may be the same in other arrangements, or in yet further designs the longitudinal length of the proximal occluding balloon 38 is less than the longitudinal length of the distal occluding balloon 42. The distal occluding balloon 42 may be coaxial with the shaft 104 in certain arrangements, and, in other arrangements may be coaxial with channels 70 or 72. In some embodiments the curve and angulation of the segment 44 of the shaft of the catheter located between the proximal balloons is shaped to achieve a coaxial position of the balloon 42 in relation to the central axis of the left carotid artery and to assure its most adequate occlusion without undue trauma to the wall of the vessel. According to our measurements of the CT scan of multiple patients the optimal angulation of the segment 44 of the catheter shaft that is necessary to achieve an optimal coaxial position of the proximal and/or distal occluding balloons in relation to the central axis of the innominate and/or left carotid arteries respectively, would be the angle of 180±45 degrees for the secondary curve of the catheter corresponding to segment 44 of the catheter shaft. This angle may be 30±15 degrees, if measured between the segments of the shaft of the catheter located at the levels of the proximal and distal occluding balloons. In addition, the optimal diameter ratio of the proximal vs. distal occluding balloon should be about 2.0 with the range of 1.5 to 2.5 as the average diameter ratio between the diameters of the innominate and left carotid arteries is about 2.0 with the range of 1.5-2.5. Therefore, in some embodiments it would be advantageous to design the proximal and distal occluding balloon according to these parameters and principles, where the diameter of the proximal balloon inflated in the innominate artery is 1.5-2.5 (average 2.0) times larger than the diameter of the distal occluding balloon inflated in the left carotid artery. The most appropriate diameter of the proximal occluding balloon upon it's inflation is determined on the basis of CT scan and/or angiography and may be 2.0±0.2 cm, whereas the diameter of the distal occluding balloon may be 1.0±0.2 cm.

In yet other exemplary embodiments, the distal occluding balloon 42 is not coaxial with shaft 104 and is not coaxial with channels 70 or 72. In order to achieve the 2.0 (range 1.5-2.5) diameter ratio of the proximal vs. distal occluding balloon in the embodiments, where both balloons have a common inflation channel 68 and/or 72 and a common inflation port 46 and/or 48 we disclose the following design characteristics of the proximal and distal occluding balloons, based on their particular shape, volume and a relative compliance of the balloon material allowing to reach a required diameter of the occluding balloons for each artery while using a common inflation channel and inflation port when the occluding balloons may be in fluid connection with each other.

The diameter 112 of the distal occluding balloon 42 is less than the diameter 110 of the proximal occluding balloon 38. In other exemplary embodiments diameter 110 may be less than diameter 112, or the diameters 110 and 112 may be equal to one another. The diameters 110 and 112 may be the same along the entire longitudinal lengths of the occluding balloons 38, 42, or the diameters 110 and 112 may be different at different points along the longitudinal lengths of the occluding balloons 110 and 112. The diameters 110 and 112 and cross-sectional shapes of the proximal and distal occluding balloons 38, 42 are described when outside of the body of the patient.

Figure 19:
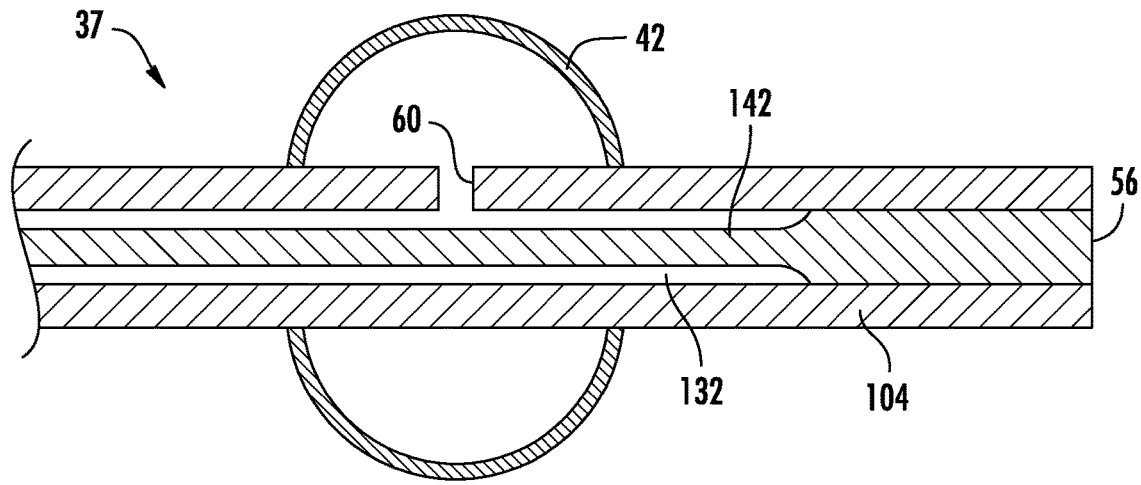
FIG. 19 is a cross-sectional, view of the distal end of the catheter that has a guide wire with a thickened portion.

The distal occluding balloon channel 72 may terminate proximal to the distal end of the distal occluding balloon 42. The end pressure measurement channel 70 and/or a common pressure measurement-guidewire channel 132 may extend distally beyond the distal occluding balloon 42. The distal tip of the shaft 104 terminates at a distal tip opening 56 at its terminal distal end. The shaft 104 extends beyond the distal occluding balloon 42, but in other arrangements, the distal occluding balloon 42 in the inflated state may extend beyond the terminal distal end of the shaft 104 in the distal direction. The end pressure measurement port 50 can be in communication with the end pressure measurement channel 70, 132 or other catheter channels that in turn may or may not terminate at the distal tip opening 56. The channel 70 in other arrangements may be in fluid communication with one or both channels 68 and 72 via connections 152 (FIGS. 7-A, 8-A, 10-A). Likewise, in yet other exemplary embodiments, channel 70 is not in fluid communication with channels 68 and 72, but channels 68 and 72 are in fluid communication with one another, or represent a single channel (FIGS. 9B, 10-B) so that the proximal and distal occluding balloons 38, 42 inflate and deflate with one another. Distal tip opening 56 may be used for pressure measurements distal to the distal occluding balloon 42. However, in some embodiments a distal opening 56 may be completely or partially sealed for at least one of the channels usable for guidewires 100, 142. This arrangement allows for using the same common channel for both the guidewire and for inflation of at least one of the balloons, thus avoiding the need for creating additional separate channels and therefore allowing to decreasing the outer diameter of the catheter shaft 104. In yet additional embodiments the guidewire channel distal opening 56 may be made of inner diameter equal, or closely approximate to the outer diameter of guidewires 100, 142 leaving no space for air or fluid to leak through (FIG. 6C), while the inner diameter of some segments of other areas of the catheter channel(s) is much wider than the opening 56, thus allowing for inflation of the balloons 38, 42 via a common inflation-guidewire channel without leaking the inflation fluid, or via the opening 56 into the vessel upon inflation (as it would be blocked by a congruent tip of the guidewire from inside during its advancement to the area or through the area of distal opening 56. In addition, at least one segment of a guidewire may have one or more thickenings of its outer diameter, wherein such thickenings' outer diameter closely approximates and is congruent to the inner diameter of the catheter's guidewire and/or inflation channel, wherein such thickening is able to obstruct the distal ostium 56 of the catheter 37, or its other segment (FIG. 6-C), in order to achieve inflation of the balloon(s) via the common guidewire-balloon inflation channel (FIGS. 7-C, 8-C) without leakage of fluid or gas or air through the distal opening of the catheter, when it is occluded by the thickened portion of a guidewire and/or narrowed portion of a guidewire channel, and where depending on the position of the guidewire and its thickened segments either just one or both occluding balloons may be inflated, deflated, or excluded from inflation and deflation by virtue of positioning the guidewire in order to either occlude or open the balloon inflation openings 58 and 60. For example, as depicted on FIG. 6-C the space inside the catheter channel 70, or 132 may be totally occluded by the guidewire 142, or not occluded (FIGS. 7-C, 8-C) depending on the relative diameter of a guidewire in relation to the inner diameter (ID) of the catheter channel (FIGS. 6-D, 7-D, 8-D). In some instances the guidewire may have thickenings designated to obstruct certain areas of the catheter channels (such as a distal opening 56, or balloon, openings 58, 60 or pressure measurement channel openings 54 and/or 144) with the goal of achieving selective inflation or deflation of the balloons and/or pressure measurements at different levels of the catheter, and/or insertion of guidewires, depending on the need of a physician during any, particular stage of the procedure. The thickened portions of the guidewire 100 may mean that the thickened portions of the guidewire 100 are portions that have a larger diameter than non-thickened portions of the guidewire 100. FIG. 19 shows a guidewire 142 that has a thickened portion that is located within the inflation channel 132 that is in communication via port 60 to the distal occluding balloon 42. The thickened portion of the guidewire 142 is at the distal opening 56 and is large enough to push up against the inner walls of the inflation channel 132 and completely fill the distal opening 56 so that no fluid can pass out of the distal opening 56. The guidewire 142 is thinner proximally from the thickened portion, and a space is present between the guidewire 142 and the inner walls of the inflation channel 132 to allow inflation fluid to flow between them and through port 60 to inflate the distal occluding balloon 42. The thickened portion thus acts as a plug to seal the distal opening 56 during inflation. Movement of the guidewire 142 proximally so that the thickened portion moves proximally past the port 60 causes fluid in the distal occluding balloon 42 to flow out of the distal opening 56.

FIGS. 9 and 10 illustrate an alternative exemplary embodiment of the occluding catheter 37 that are 1, 2, 3 or 4 channel versions of the occluding catheter 37. Intermediate pressure measurement channel 74 extends from an intermediate pressure measurement port 52 to an opening 54 or 144 of the shaft 104. Opening 54 is located proximal to the proximal occluding balloon 38 and opening 144 is located distal to balloon to the proximal occluding balloon 38. The intermediate pressure measurement channel 74 may or may not be in fluid communication with the other channels 68, 70 and 72 of the occluding catheter 37. The intermediate pressure measurement channel 74 may terminate proximal or distal to the proximal occluding balloon 38. The other components of the occluding catheter 37 are the same as described above and their description need not be repeated. A manometer may be connected to the intermediate pressure measurement port 52 to allow recording of blood pressure from the opening 54. If the proximal occluding balloon 38 is located within the innominate artery 41, the opening 54 may be used to detect the dampening of the arterial pressure in the innominate 41 and right carotid artery 26R, after proximal occluding balloon 38 inflation, confirming adequacy of the flow interruption to the right carotid 26R and subclavian arteries 23R.

In another embodiment bilateral carotid 23R and 23L flow interruption can be achieved by creating a single occluding balloon 38. FIG. 11 shows one exemplary embodiment with a single occluding balloon 38. The occluding balloon 38 may extend throughout the whole distance between the bifurcation of the innominate artery 41 and the main trunk of the left carotid artery 26L. The single occluding balloon 38 may be longer than both the proximal occluding balloon 38 and distal occluding balloon 42 combined (as described in previous exemplary embodiments), with its length being in the range between 6 and 14 cm. When described as a single occluding balloon 38, it is to be understood that complete blockage of flow through the right and left carotid arteries 26R and 26L may be achieved by the single occluding balloon 38 without the use of any other occluding balloons, or without even the presence of another occluding balloon 38 carried by the occluding catheter 37.

The occluding balloon 38 may be constructed so that it has a proximal portion 116, designated to occlude the innominate artery 41, which is larger than a distal portion 118 of the occluding balloon 38 to assure adequate occlusion of the innominate artery 41. Generally, the innominate artery 41 is at least twice as large as the left carotid artery 26L. The single occluding balloon 38 may thus have a proximal portion 118 with a larger diameter than the diameter of the distal portion 118 of the single occluding balloon 38. These differences in diameters/sizes would be present when the single occluding balloon 38 is inflated without being inside of the patient. The other option involves the single occluding balloon 38 being, a large volume, highly compliant occluding balloon that does not have any disparity in the diameters/size of the proximal portion 116 and distal portion 118 when inflated and not inside of the patient. Once inflated inside of the patient and presented with arteries of different sizes, the proximal and distal portions 116, 118 of the highly compliant occluding balloon 38 expand as necessary for complete occlusion of arteries 41 and 26L at minimal pressures and without significant compression of the arterial walls 41, 26L. The single occluding balloon 38 thus expands as necessary to fill the space required for occlusion as it is a very flexible member in construction. Such a single balloon embodiment may also comprise a single inflation-guidewire configuration with all disclosed features achieving a lowest possible catheter profile and a minimal number of internal channels.

In order to facilitate the advancement of the occluding catheter 37 in patients with difficult anatomy, several catheter features are being disclosed:

a guide wire 100 and/or 142 may be used in one, two or more of the channels 70, 74 or 132. For example, to achieve more variability in catheter manipulation with multiple angles of flexion and rotation, both guidewires 100, 142 may be used with a guidewire 100 passing all the way through the catheter channel 70 and leaving the catheter via the distal opening 56, while a guidewire 142 may end at the blunt (sealed) distal channel 72, 68 and/or 132. In this case a guidewire 100 may be used for a further advancement of the catheter, while guidewire 142 may be used for stabilization of the catheter 37 during its insertion via the introducer vascular sheath into the patient's peripheral artery (such as radial artery), its advancement and, if needed—for the catheter angulation at the level of the balloons and segment 44.

With reference to FIG. 12, the guide wire 100 may not have to be used. Here, the shaft 104 is highly compliant and there is a narrow waist that makes up segment 44. The occluding catheter 37 includes a pair of occluding balloons 38, 42 and segment 44 in the middle of these occluding balloons 38, 42 improves flexibility of the occluding catheter 37. As previously described, separate or connected occluding balloon channels 68 and 72 can be used for separate or a common channel inflation of the proximal and distal occluding balloons 38 and 42. This allows for selective or synchronous control of the occlusion of the left carotid artery 26L and innominate arteries 41.

The pair of occluding balloons 38, 42 in FIG. 12 may be rearranged so that they are only a single occluding balloon 38. In this regard, the single occluding balloon 38 will have a proximal portion 116 and a distal portion 118 separated or not separated at all from each other by segment 44 that is not capable of being inflated. A single occluding balloon channel 68 can be used to inflate both the proximal and distal portions 116, 118. Although a single occluding balloon 38 is present, in some embodiments it may be divided into two or more portions via uninflated segments such as segment 44 or by various other bands or waists that effect division. Segment 44, when effecting separation of proximal and distal portions 116, 118, achieves better flexibility of the occluding catheter 37 at the level between the two portions 116, 118.

This option may allow for an easier passage of the occluding catheter 37 in case of a sharp angle between the innominate artery 41 and left carotid artery 26L and/or left subclavian artery 23L. If a pair of occluding balloons 38, 42 is employed, the same goal may be achieved by the segment 44. Measurement of arterial pressure and assessing the pressure waveform via the openings 54, 56, 144 an/or pressure wires imbedded into the surface of the catheter shaft 104 and/or balloons 38,42 before and after inflation will allow confirmation of the adequacy of the flow interruption in the carotid arteries 26L and 26R.

A manometer or electronic pressure recorder 124 may be in communication with the pressure wire imbedded into the catheter shaft, or—the end pressure measurement port 50 and the intermediate pressure measurement port 52 to measure pressures at the opening of the shaft 54 (downstream from the proximal occluding balloon 38 in the innominate artery 41 or right subclavian artery 23R) and at the distal tip opening of the shaft 56 (downstream from the distal occluding balloon 42 in the left carotid artery 26L). A pressure supply 126 is in communication with at least one of the occluding balloon inflation ports 46, 48, 70 or 130 to provide inflation pressure for the occluding catheter 37. An alarm system 114 is in communication with the pressure supply 126 and an electronic pressure recorder-manometer 124. Should the physician or physician's assistant forget to deflate the occluding balloons 38, 42 in a timely fashion, an alarm would go off and the occluding balloons 38, 42 would deflate spontaneously to avoid undue interruption of the cerebral flow. The alarm could be also triggered by the occurrence of emboli 27 detected by transcranial or carotid Doppler 122 (also in communication with the alarm system 114) echocardiography appearance of embolic particles in the heart chambers and/or aorta, thus indicating an urgent need for temporary occlusion of the cerebral flow. Here, the alarm system 114 will cause inflation of the occluding balloons 38, 42. The alarm system 114 along with deflation or inflation of the occluding balloons 38, 42 could be overridden by the physician when clinically indicated.

Another exemplary embodiment of the occluding catheter 37 is shown in FIGS. 13 and 14. This embodiment achieves a temporary interruption of cerebral arterial inflow without placing the occluding catheter 37 into carotid arteries 26L and 26R by creating a single occluding balloon 38 extending the distance between the bifurcation of the innominate artery 41 and the orifice 98 of a left subclavian artery 23L. The single occluding balloon 38 may be provided so that no other occluding balloons, and in some instances no other balloons at all, are present on the occluding catheter 37.

When inflated, the occluding balloon 38 will effectively occlude the orifice of the right subclavian artery 96, the orifice of the right carotid artery 94, the orifice of the left carotid artery 92, and the orifice of the left subclavian artery 98 which are all branches of the aortic arch 22. This inflation will block flow into the brain by blocking flow through the right, and left carotid arteries 26R and 26L and through both the right subclavian and left subclavian arteries 23R and 23L and, therefore, both right and left vertebral arteries. The occluding catheter 37 in this arrangement achieves complete avoidance of any manipulations on the carotid arteries 26R and 26L, thus eliminating the risk of induced injury or emboli 28, leading to stroke, problems that are known to occur in prior devices. As shown, the occluding balloon 38 is not located within the right or left carotid arteries 26R, 26L when inflated. The occluding balloon 38 may also not be located within the right subclavian artery 23R when inflated in some embodiments.

The occluding catheter 37 may be inserted via the peripheral artery, of the right or left arm. FIGS. 13 and 14 show introduction through the right arm for vascular access. A guide wire 100 and/or 142 may first be passed via the brachial artery and advanced first into the innominate artery 41, then the aortic arch 22, and finally into the left subclavian artery 23L. The occluding catheter 37 will be next advanced over the guide wire 100 and consequently first into the innominate artery 41, then the aortic arch 22 and finally into the left subclavian artery 23L. The occluding balloon 38 extends from the level of the innominate artery 41 to the level of the left subclavian artery 23L.

The left arm is used for insertion as shown in FIG. 15. The occluding catheter 37 is first advanced into the left subclavian artery 23L, then the aortic arch 22, and then into the innominate artery 41 and right subclavian 23R artery. The occluding balloon 38 extends through the whole distance between the left and right subclavian arteries 23L, 23R. Inflation of the occluding balloon 38 occludes the orifices 96, 94, 92, and 98 to completely prevent the emboli 28 from entering cerebral circulation via all potential ways of arterial inflow. Pressure in the right subclavian artery 23R may be measured using the distal tip opening 56, and opening of the shaft 54 can be used to measure blood pressure in the left subclavian artery 23L.

Although the occluding balloon 38 is a single occluding balloon introduced through the left arm of the patient in FIG. 15, should the occluding catheter 37 include proximal and distal occluding balloons 38, 42 and be desired for insertion through the left arm the relative occluding balloon 38, 42 sizes may be varied. For example, the distal occluding balloon 42 may be larger in diameter 112 than the diameter 110 of the proximal occluding balloon 38. The distal occluding balloon 42 when inflated may block flow through the innominate artery 41, and the proximal occluding balloon 38 would block flow through the left carotid artery 26L. The segment 44 would be between the balloons 38, 42 and would be located in the aortic arch 22. The proximal portion of the occluding catheter 37 may be located within the left subclavian artery 23L. Placement may be effected by first inflating the distal occluding balloon 42 to allow arterial blood flow to naturally pull it into the innominate artery 41. The distal occluding balloon 42 may be deflated to allow for determination of the positioning of the occluding catheter 37. The proximal occluding balloon 38 may be inflated to determine its positioning as it may block flow through both the left carotid artery 26L and the left subclavian artery 23L.

Although described as blocking flow through both of the carotid arteries 26R and 26L, it is to be understood that only one of the carotid arteries 26R or 26L may be blocked in certain arrangements and uses of the occluding catheter 37.

The size and shape of the occluding balloon 28 can vary depending on the patient's anatomy and the size of the arteries discussed herein. For this purpose it may be the case that low pressure, highly compliant occluding balloons 38 of conical and ovoid shape are used with larger central segments corresponding to the patient's innominate artery 41, and aortic arch 22, and the narrower peripheral segments corresponding to the level of right and left subclavian arteries 23R and 23L. The large segment of the occluding balloon 38 should be large enough to occlude the innominate artery 41 and the orifice 92 of the left carotid artery 23L, but not too large to compromise the lumen of the aortic arch 22. It may be made sufficiently compliant to assure slight herniation into the orifices 96, 94, 92 and 98 during inflation. Thus in some arrangements, the occluding balloon 38 may extend into any one of or all of the arteries 23R, 26R, 26L and 23L. As used herein, the term cone or conical is understood to include shapes that also are known as frustums in which the tip of the cone is flat so that a point is not present.

The diameter 120 of the aortic arch 22 may be significantly larger than the diameter 110 of the occluding balloon 38 when the occluding balloon 38 is inside of aortic arch 22 and is inflated. This arrangement will block blood flow through the carotid arteries 26R, 26L but will allow for divergence of blood flow carrying the emboli 28 into, the distal aorta 24 and away from the cerebral circulation. The maximal diameter 110 of this segment of the occluding balloon 38 within the aortic arch 22 may not exceed 60-70% of the diameter 120 of the aortic arch 22. In other arrangements, the diameter 110 within the aortic arch 22 may be up to 25%, up to 35%, 50%, or up to 60% of the diameter 120.

Although described as preventing emboli 28 from flowing through the carotid arteries 26R, 26L, the occluding catheter 37 may also be used to prevent emboli 28 from flowing through the right subclavian artery 23R and/or the left subclavian artery 23L. This prevention may be in addition to or alternatively to prevention of flow through the carotid arteries 26R and/or 26L.

Figure 17A:
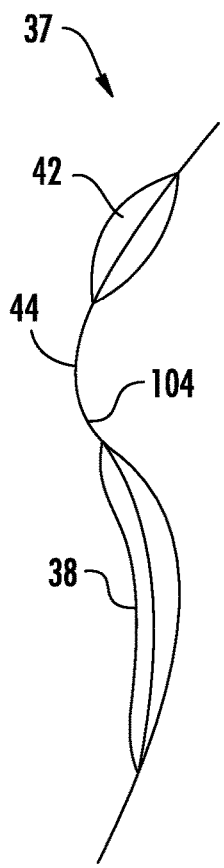
FIG. 17A is side view of a distal end of the catheter in one embodiment.
Figure 17B:
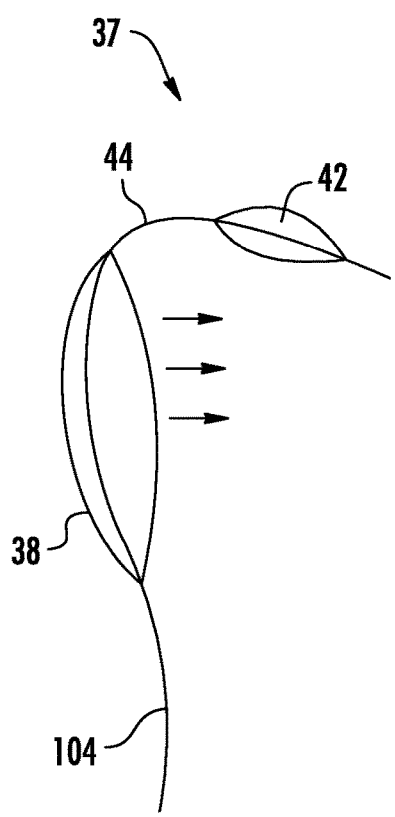
FIG. 17B is a side view of the catheter of FIG. 17A with the proximal occluding balloon inflated to cause desired flexing of the shaft.
Figure 17C:
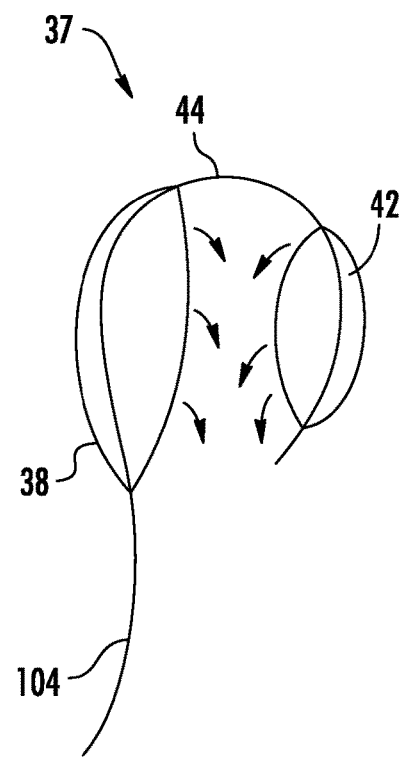
FIG. 17C is a side view of the catheter of FIG. 17B with the distal occluding balloon inflated along with the proximal occluding balloon to cause additional flexing of the shaft.
Figure 18:
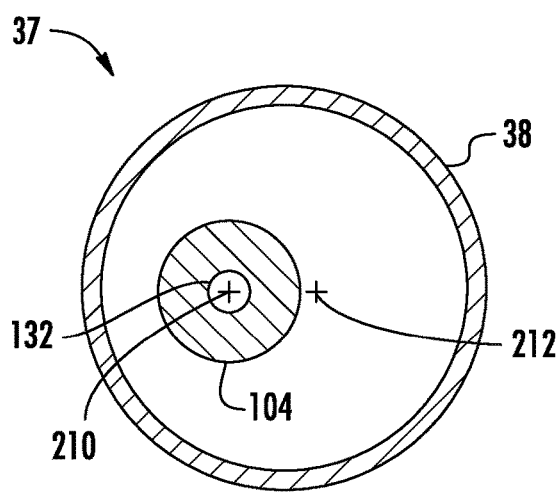
FIG. 18 is a cross-sectional view of an asymmetrically positioned occluding balloon and shaft.

FIGS. 17A-17C illustrate an exemplary embodiment of the catheter 37 that features progressive, controllable flexion of the shaft 104 upon inflation of the proximal and distal occluding balloons 38, 42. FIG. 17A shows proximal and distal occluding balloons 38, 42 in deflated states. They may be asymmetrically centered on the shaft 104, have more and less compliant portions, or feature any of the above mentioned means of causing tension to be imparted onto the shaft 104 upon inflation. FIG. 18 is a cross-sectional view that shows the shaft 104 asymmetrically positioned relative to the proximal occluding balloon 38 so that inflation may cause the shaft 104 to bend. In this regard, the shaft 104 is not coaxial with the proximal occluding balloon 38 but is instead off center. The shaft 104 has a center 210 which may be an axis 210 that is the longitudinal axis of 210 of the shaft 104 such that the outer walls of the shaft 104 are equal distant therefrom in the radial direction. The proximal occluding, balloon 38 has a center 212 that can also be the longitudinal axis 212 of the proximal occluding balloon 38. The longitudinal axes 210 and 212 are not co-axial but are instead offset and a distance from one another. The proximal occluding balloon 38 is inflated in FIG. 17B and the distal occluding balloon 42 remains deflated. The catheter shaft 104 is bent into a fish-hook shape and flexes in the direction of the illustrated arrows due to the tension imparted thereon through the design of the proximal occluding balloon 38.

Although FIG. 18 shows the proximal occluding balloon 38, the distal occluding balloon 42 could be configured in a similar manner regarding the axes and the offset arrangement of these centers/axes. The occluding balloon 38, 42 may be described as being eccentric. Inflation causes more tension on one side of the shaft 104 so the shaft 104 is, bent or twisted accordingly upon inflation. As described herein, instead of or in combination with eccentric positioning of the balloon 38, 42 relative to the shaft 104, the balloon 38, 42 may be made so that one portion of the balloon 38, 42 is more compliant than another portion of the balloon 38, 42. Inflation of the balloons 38, 42 causes unequal expansion due to this compliance difference so that more tension is applied to the shaft 104 on one side than the other leading to bending and/or twisting of the shaft 104 upon inflation.

The user may then inflate the distal occluding balloon 42 as shown in FIG. 17C to further curve the shaft 104 in the direction of the arrows so that a generally round, curved distal end of the shaft 104 results. The distal occluding balloon 42 may extend towards the pivot point of the shaft 104 upon inflation. With the inflation of both balloons 38, 42 a greater degree of flexion of the shaft 104 results. The shaft 104 achieves a shepherds hook shape and has a radius of curvature. The proximal occluding balloon 38 may extend into the opening of this shepherds hook shape from 15% to 50% of the length of the radius of curvature. Deflation may result in an opposite movement of the shaft 104 so that it returns back to the shape of FIG. 17A in a progressive manner.

To bend or twist the shaft 104, the proximal and distal occluding balloons 38, 42 could have necks that are offset from a central longitudinal axis of the shaft 104 so that 25% to 75% of the balloon circumference, volume, and surface is located on one side of the shaft 104 or is located on one side of the central longitudinal axis of the shaft 104.

Figure 21:
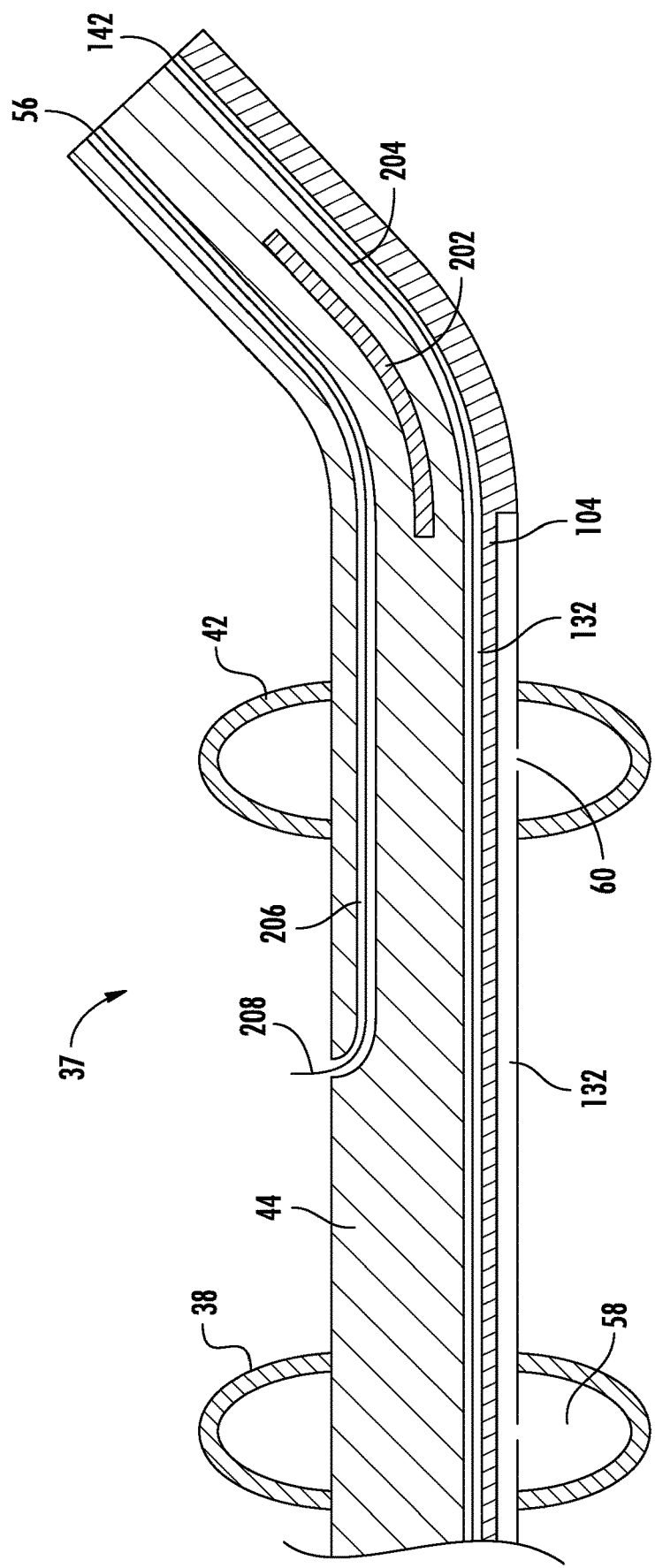
FIG. 21 is a cross-section view of an end of an occluding catheter that has a pair of guidewire channels.

FIG. 21 shows the coil 202 in the shaft 104 that imparts a bend to the distal end 56 so the tip of the shaft 104 is bent to effect placement within certain anatomy of the patient. The shaft 104 in FIG. 21 has a common inflation channel 132 through which inflation fluid may be transported into both the proximal and distal occluding balloons 38, 42 to cause their inflation and deflation. There is a guidewire channel 204 separate the common inflation channel 132 through which the guidewire 142 can be disposed. The guidwire channel 204 could be closed at its distal end so that the guidewire 142 does not extend past the terminal distal end of the shaft 104. A second guidewire channel 206 is separate from both, the common inflation channel 132 and the first guidewire channel 204 and a second guidewire 208 is disposed within the second guidewire channel 206. The second guidewire channel 206 starts at the segment 44 and extends to the distal tip and may or may not open at the distal tip at the distal terminal end of the shaft 104 in accordance with various exemplary embodiments. The start point of the second guidwire channel 206 may be located from 40-60 millimeters from the terminal distal end of the shaft 104. The catheter 37 may thus be configured so that two guidewires 142, 208 are present each having their own guidewire channel 132, 206 that are separate and not in communication with one another.

Figure 5A:
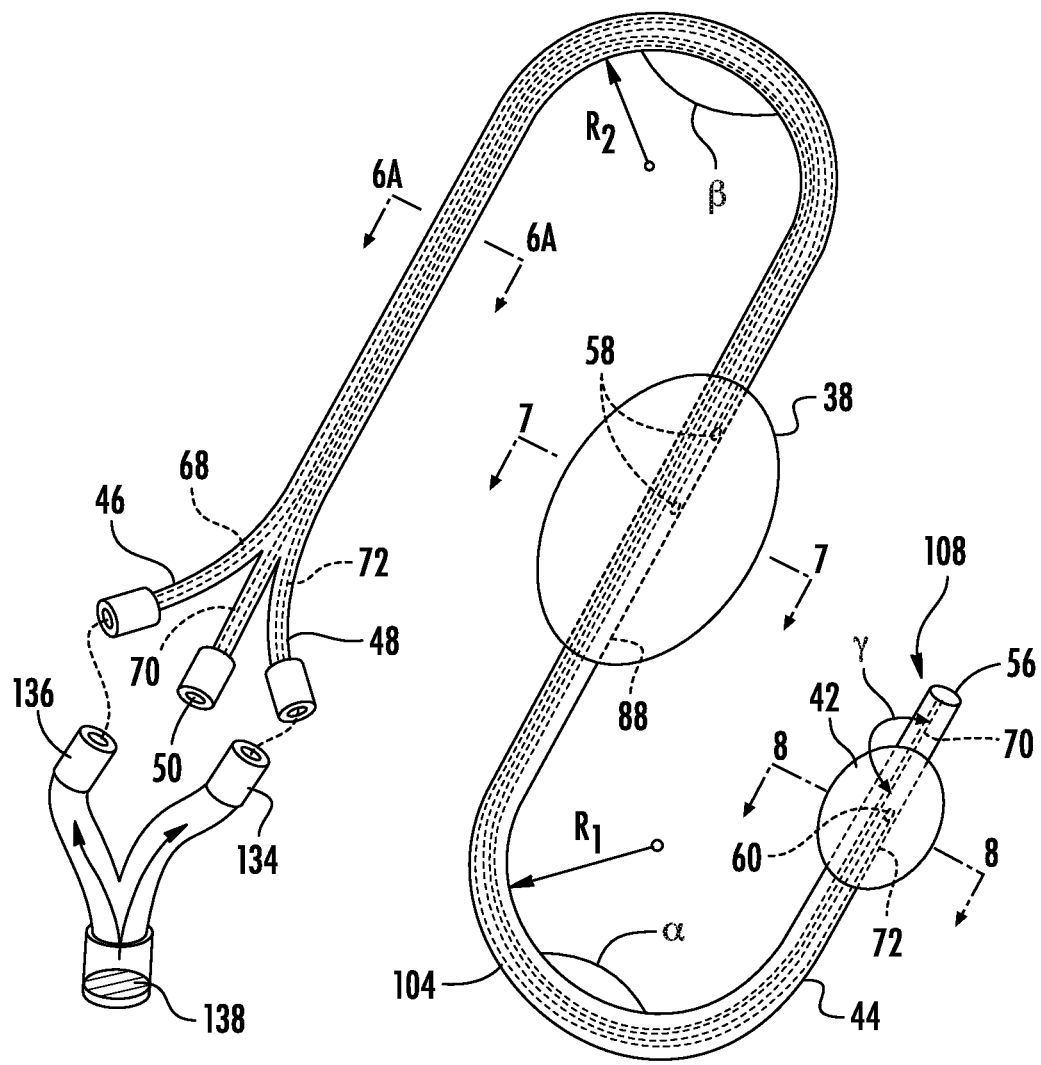
FIG. 5-A is a front view of an occluding catheter in accordance with an exemplary embodiment with angles and curvatures of segments of the catheter.
Figure 5B:
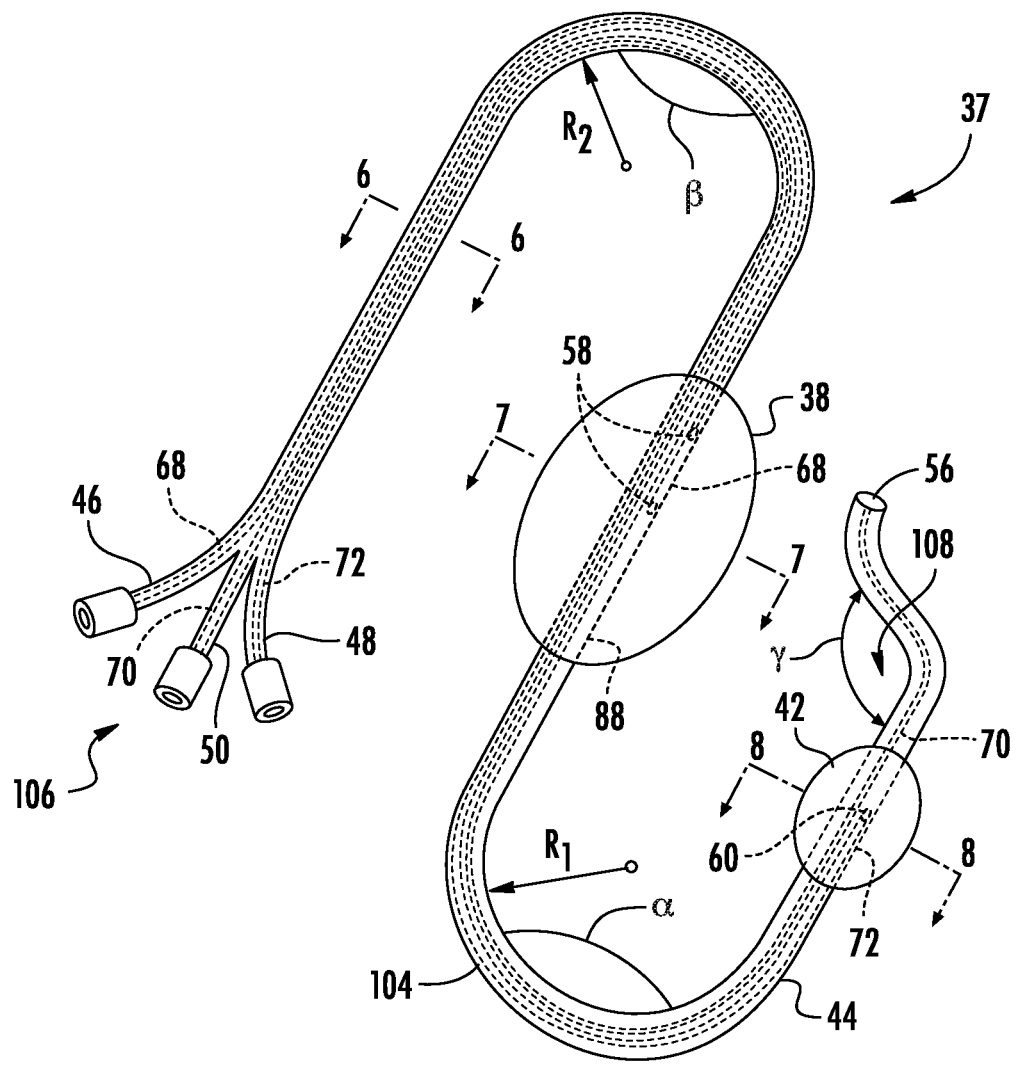
Figure 5C:
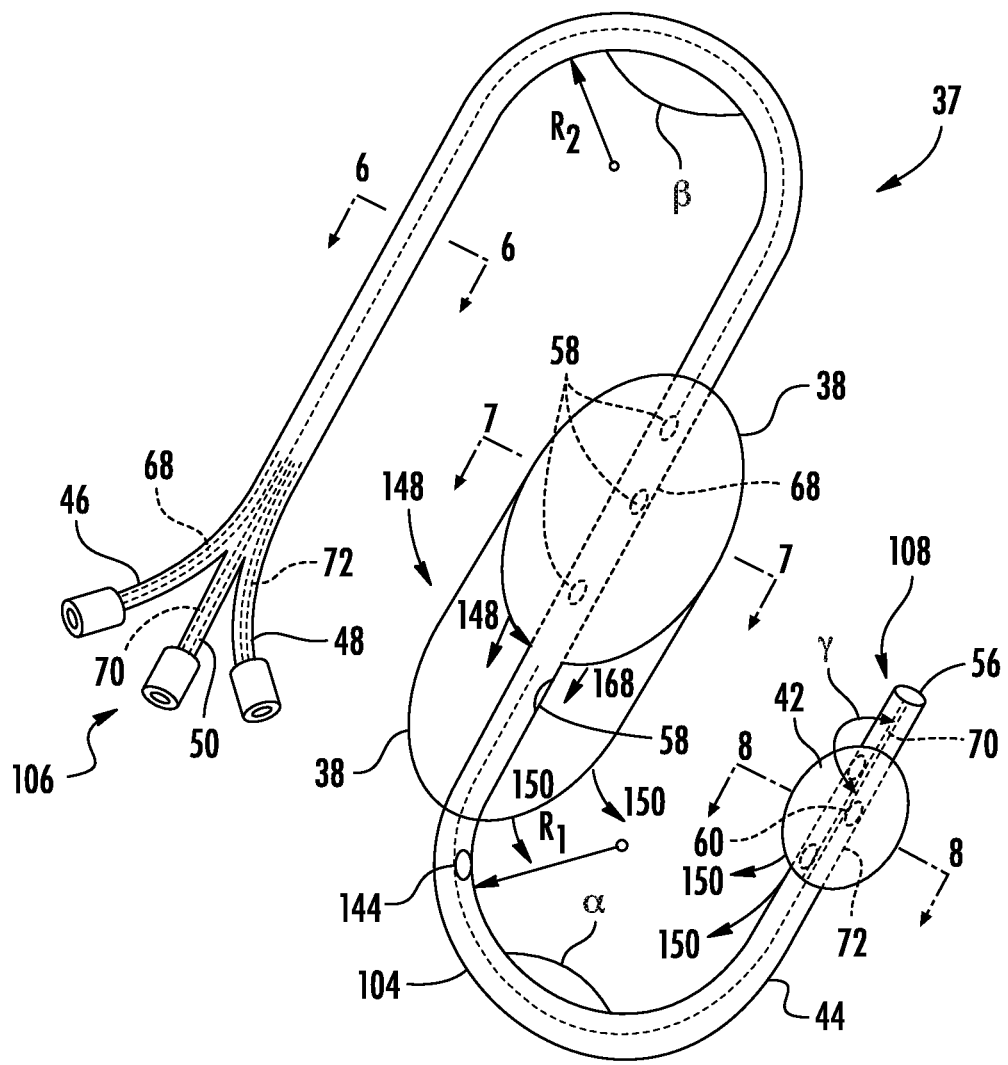
Figure 5D:
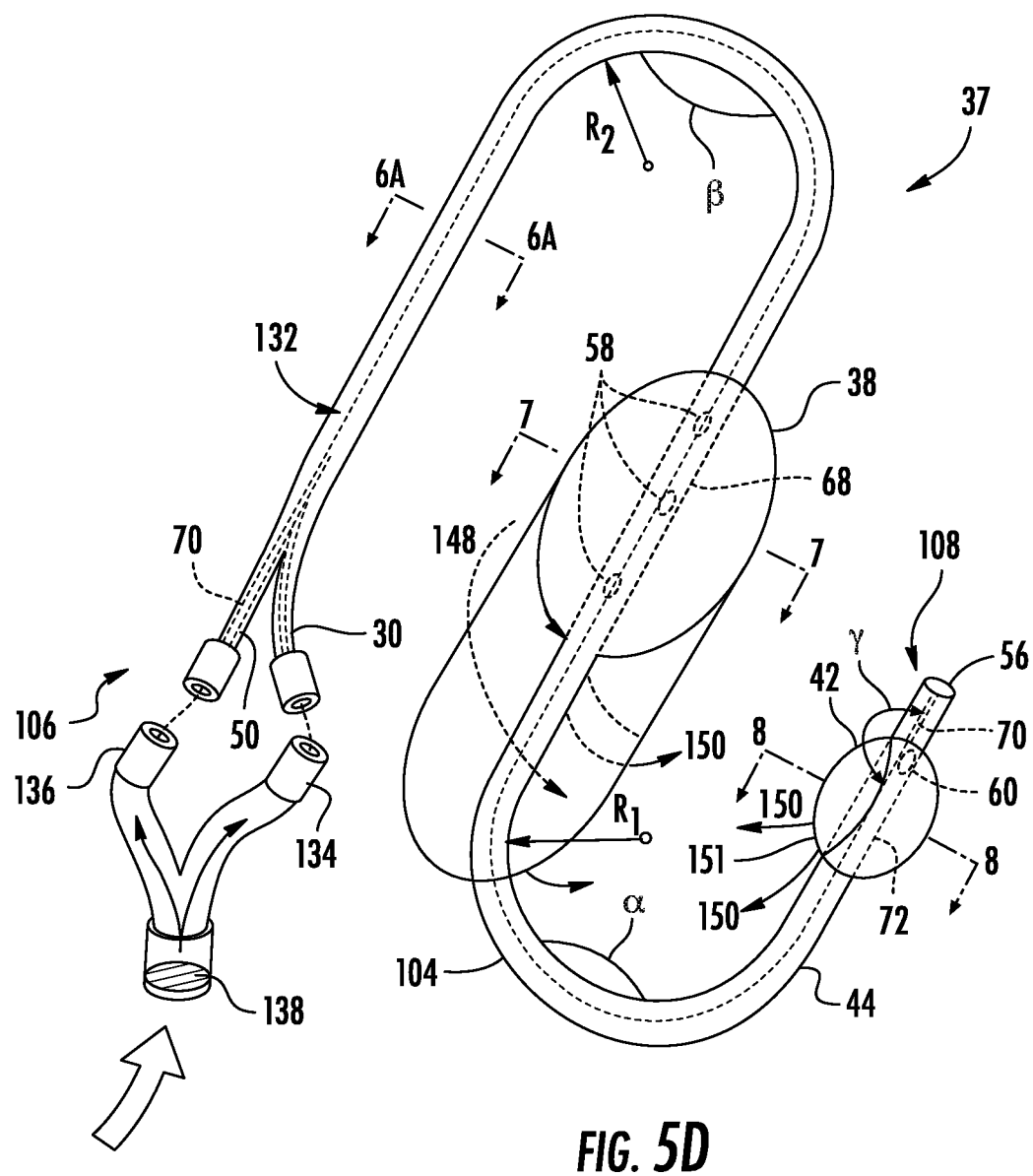
Figure 6A:
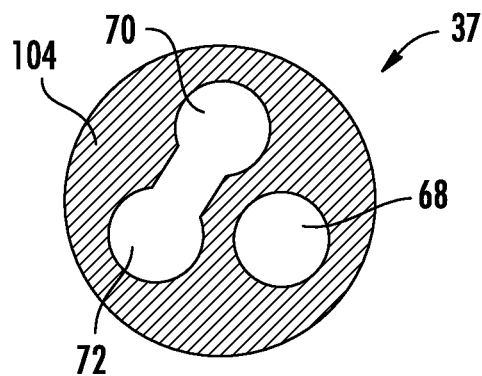
FIG. 6-A is a cross-sectional view taken along line 6-6 of FIG. 5-A.
Figure 6B:
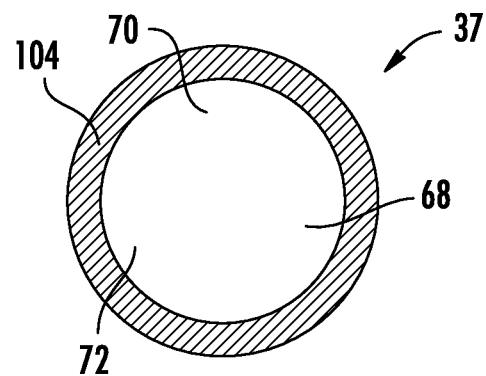
Figure 6C:
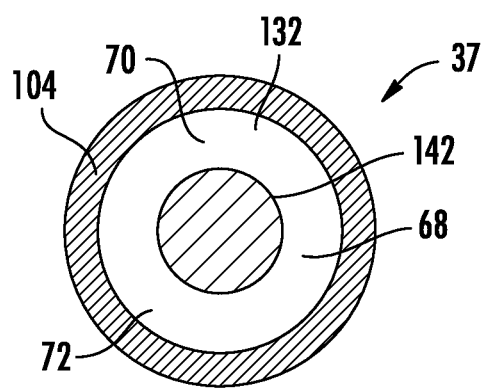
Figure 6D:
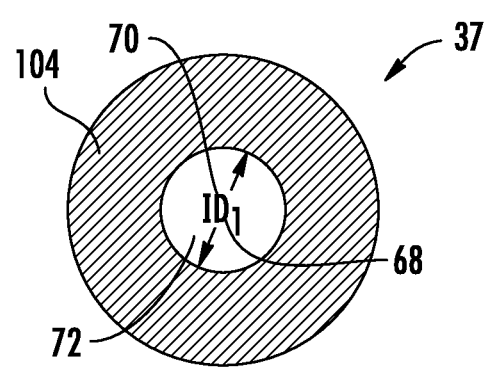
Figure 7A:
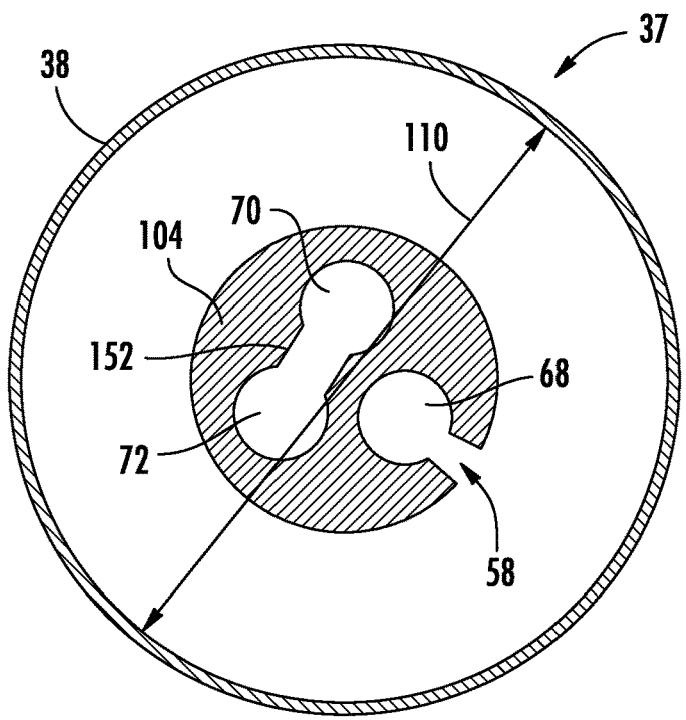
FIG. 7-A is a cross-sectional view taken along line 7-7 of FIG. 5-A.
Figure 7B:
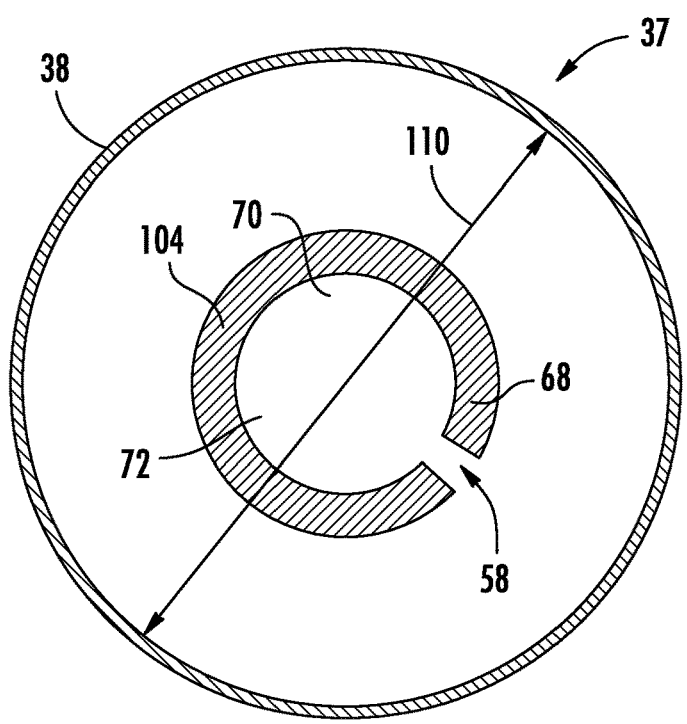
Figure 7C:
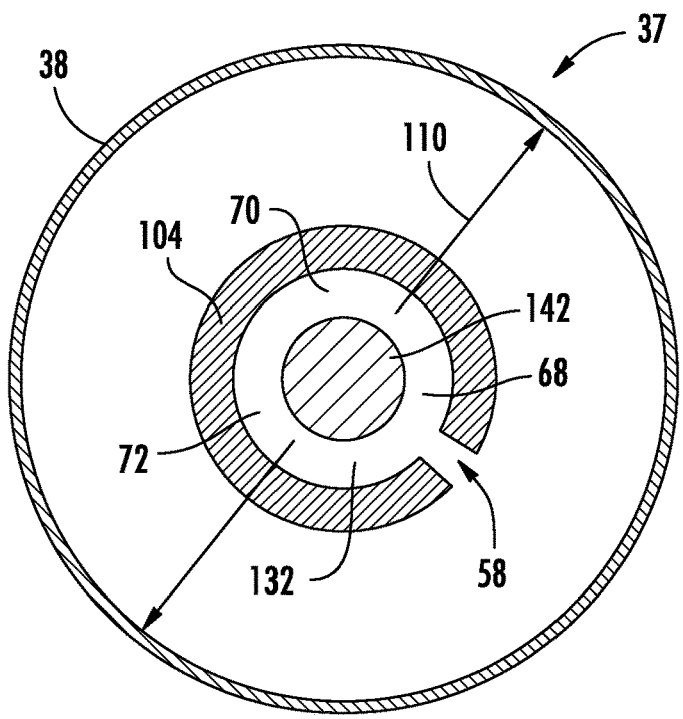
Figure 7D:
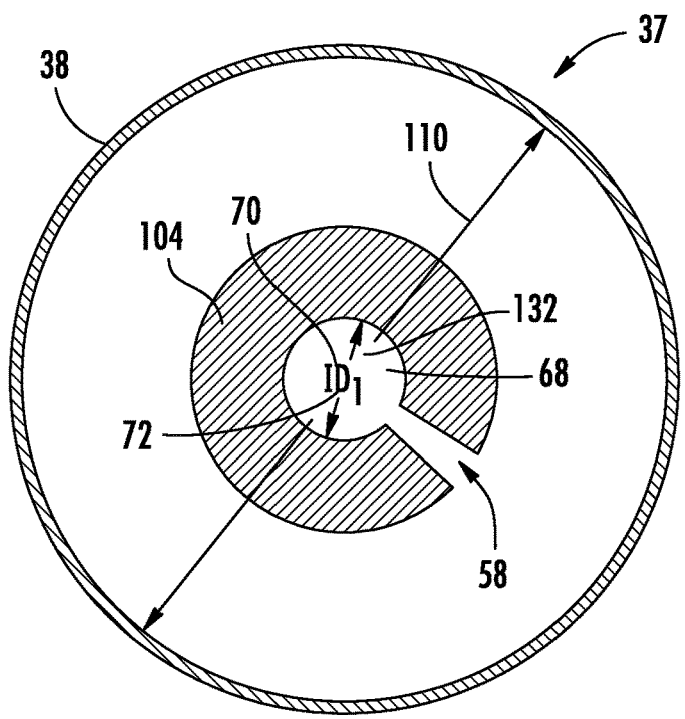
Figure 8A:
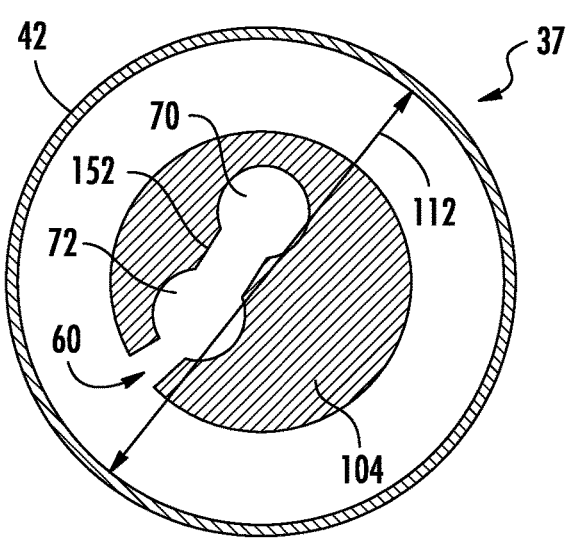
FIG. 8-A is a cross-sectional view taken along line 8-8 of FIG. 5-A.
Figure 8B:
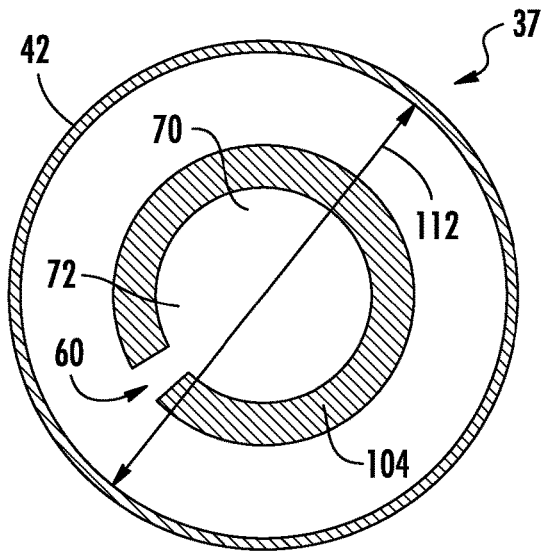
Figure 8C:
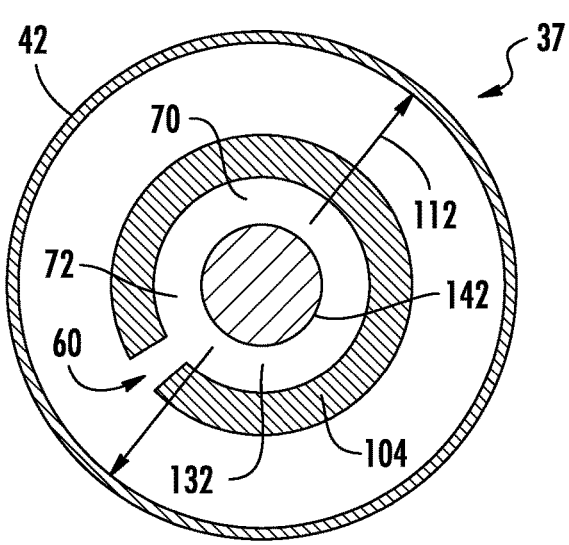
Figure 8D:
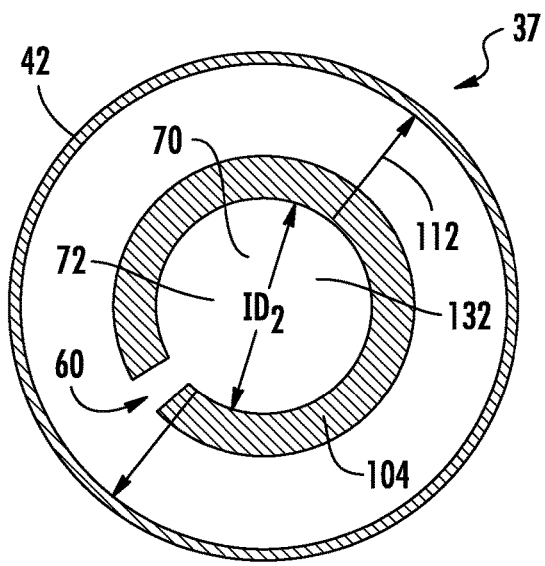

The various catheters 37 have been described as having a common inflation channel 132 through which inflation fluid flows to inflate both the proximal and distal occluding balloons 38, 42. The occluding balloons 38, 42 can be said to be in communication with one another as a passageway exists from between them via this common inflation channel 132. Alternate embodiments of the common inflation channel 132 are also possible in which a passageway in the shaft 104 extends to the proximal occluding balloon 38, and a separate passageway extends to the distal occluding balloon 42. These two separate passageways still comprise a common inflation channel because inflation fluid upstream could be pumped into both of them from a common source at the same time so that inflation fluid splits upstream into the two passageways for subsequent inflation of the occluding balloons 38, 42. As such, it is to be understood that the term common inflation channel also includes embodiments in which each occluding balloon 38, 42 has its own channel but they are both fed from a common port or source. For example, two syringes of inflation fluid could be linked or tied into one another via a connection so that their injection and retraction of inflation fluid is simultaneous. FIG. 5A shows an example of a common inflation channel 132 in which two channels are present but are serviced via the same, linked single inflation port opening 138. Also, the term common inflation port may also mean a single port through which inflation fluid flows to both proximal and distal occluding balloon 38, 42 that have separate channels, such as the single port 138 in FIG. 5A that services two passageways that could be described as a common inflation channel. Also, the term common inflation port could be multiple ports that are linked in that inflation fluid flows simultaneously through. As an example, with reference to FIG. 5A one could connect two (or more) syringes that are linked to one another to ports 46, 48, and/or 50 so that, these syringes simultaneously inject fluid into separate ports 46, 48, 50. Although two or more physically separate ports 46, 48, 50 exist, a common inflation port is defined because inflation fluid is simultaneously injected through these separate ports 46, 48, 50 at the same time to inflate any occluding balloons they are associated with in the manner described herein. As such, the use of the terms common inflation channel and common inflation port may refer to arrangements in which the occluding balloons 38, 42 are inflated via simultaneous injection of inflation fluid which can inflate the occluding balloons 38, 42 at a simultaneous rate of inflation even through multiple ports and channels to them could exist.

The following Clauses describe different embodiments of the present occluding catheter and method:

Clause 1 An occluding catheter for preventing stroke by occluding blood flow to a right carotid artery and a left carotid artery or left subclavian artery of a patient, comprising:
a shaft that has a proximal end and a distal end;
a proximal occluding balloon carried by the shaft, wherein the proximal occluding balloon is inflated to occlude blood flow to the right carotid artery;
a distal occluding balloon carried by the shaft, wherein the distal occluding balloon is inflated to occlude blood flow to the left carotid artery or a left subclavian artery;
wherein, the shaft has a segment that is located between the proximal occluding balloon and the distal occluding balloon;
wherein, the proximal occluding balloon is configured to occlude the innominate artery and the distal occluding balloon is configured to occlude the left carotid artery, and
wherein, a tip of the shaft at the distal end assumes a designated curvature and shape to assure entry of the tip of the shaft into the left carotid artery or left subclavian artery while the proximal occluding balloon is located in an innominate artery, and
wherein the degree of shaft flexion is adjusted by at least one of a guidewire position, the proximal occluding balloon inflation and/or deflation, the distal occluding balloon inflation and/or deflation, or combinations thereof.

Clause 2 An occluding catheter as set forth above,
wherein a radius of the curvature of the segment between the proximal and distal occluding balloons is 6 mm+/−3.4 mm;
wherein a length of the segment between the proximal and distal occluding balloons is 18 mm+/−5.1 mm; and
wherein an angle of curvature of the segment between the proximal and distal occluding balloons is 180+/−30 degrees.

Clause 3 An occluding catheter as set forth above, wherein the proximal occluding balloon and the distal occluding balloon are inflated through a common inflation channel and are in fluid communication with each other.

Clause 4 An occluding catheter as set forth above, wherein the shaft has a first channel and a second channel that both start at the proximal end of the shaft and end at the distal end of the shaft, wherein a guidewire is insertable through the second channel, and wherein the first channel is an inflation channel, and wherein the first channel and the second channel are two separate channels and are not in fluid continuity with each other.

Clause 5 An occluding catheter as set forth above, wherein the shaft has a channel that starts at the proximal end of the shaft and ends at the distal end of the shaft, wherein a guidewire is present within the channel and the channel is configured for having the guidewire therein and inflation fluid transferred through the channel at the same time the guidewire is present within the channel.

Clause 6 An occluding catheter as set forth above, wherein the shaft has a first guidewire channel that has a distal opening at the tip of the shaft, wherein the shaft has a second guidewire channel that does not have an opening at the distal end of the shaft, and wherein the first guidewire channel and the second guidewire channel are two separate channels.

Clause 7 An occluding catheter for preventing stroke by occluding blood flow to at least one of a right carotid artery, an innominate artery, a left carotid artery, a right subclavian and a left subclavian artery of a patient, comprising:
a shaft that has a proximal end and a distal end;
a proximal occluding balloon carried by the shaft, wherein the proximal occluding balloon is inflated to occlude blood flow to at least one of the right carotid artery, the innominate artery, and the right subclavian artery;
a distal occluding balloon carried by the shaft, wherein the distal occluding balloon is inflated to occlude blood flow to at least one of the left carotid artery and the left subclavian artery;
wherein the shaft has a segment that is located between the proximal occluding balloon and the distal occluding balloon;
wherein the catheter has a proximal occluding balloon inflation channel for the proximal occluding balloon;
wherein the catheter has a distal occluding balloon inflation channel for the distal occluding balloon and wherein said channels are not in fluid communication with each other;
wherein the catheter has at least one guidewire channel that starts at the proximal end of the shaft and ends at the distal end of the shaft, and wherein the guidewire channel is in fluid communication and shares a portion of a lumen with either the proximal occluding balloon inflation channel or the distal occluding balloon inflation channel.

Clause 8 The occluding catheter as set forth above, wherein there is a common inflation channel for inflation of the proximal and distal occluding balloons comprising a single inflation port and wherein the inflation via a common inflation port leads to a synchronous expansion of the proximal and distal occluding balloons with an expansion ratio in which the proximal occluding balloon exceeds expansion of a distal balloon by a factor of 1.3-2.5.

Clause 9 The occluding catheter as set forth above, wherein the proximal occluding balloon is located within an innominate artery of the patient and upon inflation has a larger diameter than the distal occluding balloon and is configured to occlude blood flow to the right carotid artery and the innominate artery and a right subclavian artery of the patient, and wherein the distal balloon is located within the left carotid artery of the patient and upon inflation has a smaller diameter than the proximal occluding balloon and is configured to occlude blood flow to the left carotid artery.

Clause 10 The occluding catheter as set forth above, wherein a diameter of the proximal occluding balloon upon inflation is equal to or larger than a diameter of an innominate artery of the patient, and wherein a diameter of the distal occluding balloon is equal to or larger than a diameter of the left carotid artery, and wherein a ratio of a diameter of the proximal occluding balloon to a diameter of the distal occluding 2:1.

Clause 11 The occluding catheter as set forth above, wherein the volume of the proximal occluding balloon equals the volume of the distal occluding balloon, wherein a diameter of the proximal occluding balloon is 1.5-2.5 times larger than a diameter of the distal occluding balloon.

Clause 12 The occluding catheter as set forth above, wherein upon inflation the proximal occluding balloon has a diameter that is at least 50% larger than a diameter of the distal occluding balloon upon inflation.

Clause 13 The occluding catheter as set forth above, wherein upon inflation a diameter of the proximal occluding balloon is at least 100% larger than a diameter of the distal occluding balloon.

Clause 14 The occluding catheter as set forth above, wherein a maximum diameter and degree of expansion of at least one of the distal and proximal occluding balloons is limited by at least one of the inflation pressure, volume and balloon compliance.

Clause 15 The occluding catheter as set forth above, wherein a maximum expansion of at least one of the proximal and distal occluding balloons is determined on the basis of at least one of the intraluminal balloon pressure, the amount of fluid/gas volume used for inflation, and compliance of the balloon material.

Clause 16 The occluding catheter as set forth above, wherein the material of the proximal occluding balloon is of an equal or similar compliance as the material of the distal occluding balloon.

Clause 17 The occluding catheter as set forth above, wherein a volume of the proximal occluding balloon is equal to a volume of the distal occluding balloon, and wherein the diameter of the proximal occluding balloon is 2 times larger than the diameter of the distal occluding balloon, wherein, both the proximal and distal occluding balloons are inflated through a single inflation channel and are in a fluid communication with one another.

Clause 18 The occluding catheter as set forth above, wherein the compliance of the proximal occluding balloon is proportionally lower than the compliance of the distal occluding balloon to maintain a diameter ratio between the proximal and distal occluding balloons in the range of 1.5-2.5 when both occluding balloons are inflated through the common inflation channel and are in fluid communication with each other, wherein the pressure in the proximal occluding balloon equals the pressure in the distal occluding balloon.

Clause 19 The occluding catheter as set forth above, wherein the ratios between the dimensions, volumes and compliances of the proximal and distal occluding balloons respectively when inflated through the common inflation channel have a ratio of the proximal occluding balloon diameter to the distal occluding balloon diameter of 1.5-2.5.

Clause 20 The occluding catheter as set forth above, wherein the volume of the distal occluding balloon is proportionally higher as the compliance of the proximal occluding balloon is higher, and wherein the volume of the distal occluding balloon is proportionally lower as the compliance of the proximal occluding balloon is lower, wherein such parameters are maintained in a ratio to keep the diameter of the proximal occluding balloon 1.5-2.5 times larger than the diameter of the distal occluding balloon when both occluding balloons are inflated.

Clause 21 The occluding catheter, as set forth above, wherein a rate of inflation (measured in $cm^3$ per sec or cc/sec) of the larger proximal occluding balloon and the smaller distal occluding balloon are similar when both occluding balloons are inflated, wherein such an equal rate of inflation being achieved by virtue of balancing the parameters determining the degree of surface tension T according to Laplace's Law in the setting of equal Pressures P within the proximal and distal occluding balloons in the setting of the Boyle-Mariotte's Law when P1=P2 while volumes are unequal, wherein a ratio of proximal and distal occluding balloon compliances are inversely proportional to the proximal and distal occluding balloon diameters, achieving synchronous and adequate expansion of the proximal and distal occluding balloons while inflated via the common inflation channel; and wherein a discrepancy in the number, size and total area of proximal and distal occluding balloon inflation holes is a factor influencing the degree of the proximal and distal occluding balloon inflation is added to counteract the differences in the proximal and distal occluding balloon volumes, diameters, type of the balloon material and compliance.

Clause 22 The occluding catheter as set forth above, wherein the proximal and distal occluding balloons are made out of a material of equal compliance and volume, and wherein a diameter of the proximal occluding balloon is at least 1.5 times larger than the diameter of the distal occluding balloon, and wherein the proximal and distal occluding balloons are in fluid communication with each other.

Clause 23 The occluding catheter as set forth above, wherein the proximal and distal occluding balloons are made out of different materials with different compliance, and wherein upon inflation a diameter of the proximal occluding balloon is at least 1.5 times larger than a diameter of the distal occluding balloon, and wherein the proximal and distal occluding balloons are in fluid communication with each other.

Clause 24 The occluding catheter as set forth above, wherein the proximal occluding balloon is a sphere, and wherein the distal occluding balloon is a cylinder, and wherein the radius of the proximal occluding balloon is 2 times larger than the radius of the distal occluding balloon, and wherein both the proximal and distal occluding balloons are in fluid communication with each other, a wherein inflation of the proximal and the distal occluding balloons causes expansion of the proximal and distal occluding balloons in such a way that for each unit of expansion diameter of the distal occluding balloon the respective value of the proximal occluding balloon exceeds by a factor of 2 or stays within a range of 1.5-2.5.

Clause 25 The occluding catheter as set forth above, wherein the proximal occluding balloon is a sphere and is 20±2 mm in diameter when inflated and wherein the distal occluding balloon is a cylinder and is 10±2 mm in diameter when inflated wherein the radius of the proximal occluding balloon is 2 times larger than the radius of the distal occluding balloon, and wherein the compliance of both the proximal occluding balloon and the distal occluding balloon is equal.

Clause 26 The occluding catheter as set forth above, wherein the length ($L_c$) of the distal occluding balloon cylinder is 10 times longer than the radius ($R_s$) of the proximal occluding balloon sphere ($L_c$=10 $R_s$).

Clause 27 The occluding catheter as set forth above, wherein the compliance of the proximal occluding balloon is lower than the compliance of the distal, occluding proportionally to an increase in the ratio of the diameter and volume of the proximal occluding balloon to the diameter and volume of the distal occluding balloon, wherein the adjustments of the balloon material, compliance, and volume can be made on the basis of calculating a conversion factor proportional to 2:1 and 4:1 derived from the Boyle's, Laplace's and Pascal's laws in order to achieve the diameter of expansion of the proximal occluding balloon to be at least 2 times larger than the diameter of expansion of the distal occluding balloon.

Clause 28 The occluding catheter as set forth above, wherein the common occluding balloon channel extends from the distal occluding balloon to the proximal occluding balloon and to a common proximal and distal occluding balloon inflation port located at the proximal end of the shaft.

Clause 29 The occluding catheter as set forth above, wherein the shaft has:
a pressure measurement channel that extends from a distal tip opening of the shaft located at the distal end of the shaft to a pressure measurement port located at the proximal end of the shaft; or a pressure wire.

Clause 30 The occluding catheter as set forth above, wherein the shaft has a pressure measurement channel and/or guidewire channel that at least partially shares the same lumen as a proximal occluding balloon inflation channel of the shaft.

Clause 31 The occluding catheter as set forth above, wherein the pressure measurement and/or guidewire channel and the proximal occluding balloon inflation channel are or are not in fluid communication with each other depending on the position of a guidewire within the pressure measurement and/or guidewire channel, wherein the proximal occluding balloon inflation channel is opened or at least partially blocked by passing the guidewire through the pressure measurement and/or guidewire channel and wherein the outer diameter of the guidewire is approximately equal to an inner diameter of the distal tip of the occluding catheter, and wherein a diameter of the guidewire is substantially less than an inner diameter of the proximal occluding balloon inflation channel, wherein the proximal occluding balloon inflation channel and the pressure measurement and/or guidewire channel are the same lumen.

Clause 32 The occluding catheter as set forth above, wherein the tip is a distal tip and is located within the left carotid artery, wherein the distal tip has a distal tip opening that is located distally from the distal occluding balloon.

Clause 33 The occluding catheter as set forth above, wherein curvature of the tip is created by stretching of at least one of the proximal and distal occluding balloons towards a pivot of curvature of the catheter shaft leading to bending of the catheter shaft upon inflation of the at least one of the proximal and distal occluding balloons and straightening of the catheter shaft upon deflation of the at least one of the proximal and distal occluding balloons.

Clause 34 The occluding catheter as set forth above, further comprising an alarm system that activates an inflation mechanism to inflate the proximal occluding balloon and the distal occluding balloon to cause inflation when microemboli are detected by transcranial Doppler, vascular Doppler, carotid Doppler, ultrasound, or echocardiography, and wherein the alarm system deflates the proximal occluding balloon and the distal occluding balloon when the proximal and distal occluding balloons remain inflated for a cut-off period of time, and wherein the alarm system has a manual override to prevent inflation and deflation by the alarm system.

Clause 35 The occluding catheter as set forth above, wherein the shaft has a guide wire channel that is the same channel as a balloon inflation channel and wherein a diameter of a guidewire at the distal and proximal ends of the catheter shaft is equal to an inner diameter of the guide wire channel at the distal, and proximal ends of the catheter shaft, wherein the diameter of the guidewire is substantially smaller than the inner diameter of the guide wire channel in the parts of the shaft of the catheter other than the distal and proximal ends of the catheter shaft allowing for fluid communication between a balloon inflation port, the balloon inflation channel and the proximal and distal occluding balloons, when the distal and proximal ends of the catheter shaft and the guide wire channels are occluded by the guidewire.

Clause 36 The occluding catheter as set forth above, wherein the portion of the shaft that has the segment that is located between the proximal occluding balloon and the distal occluding balloon is configured and made of a specific length that is from 1 to 5 centimeters and curvature congruent and conforming to an anatomy and angles between an innominate and left carotid arteries and/or left subclavian arteries and approximating angles Alpha (the angle of the segment), Beta (the angle of the shaft immediately proximal to the proximal balloon), Gamma (the angle of the tip), and Delta (the angle between the innominate artery and the left carotid artery) of the takeoff of these vessels from an Aortic arch and in relation to each other with the angle Alpha between 0 and 45 degrees in a hook configuration configured in a such way that when inserted into the aorta the distal catheter tip and/or the distal occluding balloon face an orifice of the left carotid artery and the proximal occluding balloon is located at least partially within a lumen of the innominate artery, wherein when the distal occluding balloon is positioned in the left carotid artery, the proximal occluding balloon least partially occupies a position within the lumen of the innominate artery.

Clause 37 The occluding catheter as set forth above, wherein the portion of the shaft that has the segment that is located between the proximal occluding balloon and the distal occluding balloon is configured and made of a specific radius of the curvature in the range of 5-12 millimeters.

Clause 38 The occluding catheter as set forth above, wherein the specific radius of curvature is 6 millimeters+/− 3.4 millimeters.

Clause 39 The occluding catheter as set forth above, wherein the proximal and distal occluding balloons are mounted in a stretched and/or axially rotated configuration along a longitudinal axis of the catheter leading to decreased profile and congruency of said proximal and distal occluding balloons in relation to the shaft upon deflation, and wherein expansion of said proximal and distal occluding balloons leads to proportional bending of a distal segment of the shaft creating an angle to achieve a desired position of the tip achieving a gauged degree of flexion and/or axial rotation of the distal segment of the catheter driven by different degrees of the proximal and/or distal occluding balloon inflation.

Clause 40 The occluding catheter as set forth above, wherein the distal and proximal occluding balloons are mounted at an angle under 15-45 degrees towards the longitudinal axis of the shaft.

Clause 41 The occluding catheter as set forth above, wherein the shaft has a curved distal segment having the proximal and distal occluding balloons with the segment between the proximal and the distal occluding balloons being pre-shaped as a curve of a radius of 5-12 mm, and wherein the portion of the proximal and/or distal occluding balloon that is facing inside the curve is made out of material that is less compliant than the area of the proximal and/or distal occluding balloon facing outside the curve, and wherein the expansion of the proximal and/or distal occluding balloons leads to a greater tension and angulation of the curved distal segment inside the curve of the catheter that is proportional to the degree of the proximal and/or distal occluding balloon expansion.

Clause 42 A cerebral protection catheter comprising:

a retractable sheath having pre-packaged folded deflated occluding balloons configured for insertion while two of the occluding balloons are enclosed inside the sheath to facilitate their insertion;

a catheter that is dispensed with a distal segment preloaded inside the vascular sheath with the occluding balloons crimped inside the sheath, and wherein such combination of the sheath and the catheter is inserted as a unit with subsequent advancement of the catheter out of the sheath once, the sheath is positioned inside an artery; and wherein to facilitate entry of this combination into the artery combination has a conical tapered distal tip of the catheter and/or sheath when the catheter is preloaded to act as a vascular dilator during insertion into the artery.

Clause 43 The occluding catheter as set forth above, where at least one segment of a guidewire has one or more thickenings of its outer diameter, wherein such thickenings' outer diameter closely approximates an inner diameter of a shaft's guidewire and/or inflation channel, wherein such thickening is obstructs a distal ostium of the catheter, in order to achieve inflation of the occluding balloons via the common guidewire and/or inflation channel without leakage of fluid through the distal ostium of the catheter when it is occluded by the thickened portion of the guidewire, and wherein depending on the position of the guidewire and, its thickened segments one or both occluding balloons are inflated, deflated, or excluded from inflation and deflation by depending on the relative diameter of the guidewire in relation to the inner diameter of the catheter channel.

Clause 44 An occluding catheter for preventing stroke by occluding blood flow through a right carotid artery and a left carotid artery of a patient, comprising:

a shaft that has a proximal end and a distal end; and a single occluding balloon carried by the shaft, wherein the occluding balloon is configured to occlude blood flow to both the right carotid artery and the left carotid artery when inflated, wherein the occluding catheter does not have more than the one single occluding balloon.

Clause 45 The occluding catheter as set forth above, wherein the occluding balloon has a segment that is uninflated that separates the occluding balloon into a proximal portion and a distal portion.

Clause 46 The occluding catheter as set forth above, wherein the shaft has a proximal curvature Beta, a curvature between the proximal and distal occluding balloons Alpha, and a distal curvature Gamma, wherein the Beta curvature is located 1-10 centimeters proximal to the proximal occluding balloon, wherein the Alpha curvature is directed opposite to the Beta curvature, and the curvature Gamma is located distal to the distal occluding balloon and is directed opposite to curvature Alpha, and wherein the distance between the proximal and distal occluding balloons is between 0 and 8 centimeters, and the radius of the curvature Alpha is between 4 and 12 millimeters and the radius of the Beta curvature is between 6 and 12 centimeters, and wherein the shaft is configured to exhibit fixation points, that are points of contact and radial force application between the occluding catheter and vessel walls, between the curvature Alpha and the right or left subclavian artery, and curvature beta and the innominate artery.

Clause 47 The occluding catheter as set forth above, wherein the proximal occluding balloon is located within at least one of the aortic arch and an innominate artery of the patient, and wherein the distal occluding balloon is not located within the left carotid artery of the patient.

Clause 48 The occluding catheter as set forth above, wherein the proximal occluding balloon is not located within the right carotid artery of the patient.

Clause 49 The occluding catheter as set forth above, wherein a distal portion of the proximal occluding balloon when inflated has a diameter that is at least 50% larger than a diameter of a proximal portion of the proximal balloon, and wherein the distal portion of the proximal occluding balloon is at least 30% smaller than a diameter of the aortic arch, wherein the distal portion of the proximal occluding balloon when inflated is located inside the aortic arch creating at least partial overlap of an ostium of the left carotid artery and at least partial barrier to aortic flow and deflecting emboli away from an innominate artery, the left carotid and left subclavian arteries without directly contacting and/or occluding the left-carotid and left subclavian arteries by shielding the arteries from propagation of embolic particles and preventing the embolic particles from entering orifices of the left carotid and/or left subclavian arteries by creating at least a partial mechanical and/or hydraulic barrier to the blood flow on the outer curve of the aortic arch.

Clause 50 A catheter for prevention of cerebral emboli, comprising:

a distal portion made out of a floppy compliant material that creates a protective veil over an orifice of an innominate artery, an orifice of a left carotid artery, and an orifice of a left subclavian artery preventing emboli from entering cerebral circulation, wherein said veil may have an unfolding and recoil folding capacity and be expanded with every cardiac contraction, and ejection (systole) and collapse back to a folded position with each cardiac relaxation (diastole), thus creating hemodynamic conditions preventing the entry of emboli into cerebral circulation.

Clause 51 The catheter as set forth above, wherein the veil is made without a balloon and is a collapsible, expandable and/or unfolding or unrolling mesh carrying pores of variable configuration and size.

Clause 52 The catheter as set forth above, wherein the veil is part of an occluding balloon.

Clause 53 The catheter as set forth above, wherein the distal occluding balloon and a distal portion of the proximal occluding balloon have an amount of flexibility and mobility to be advanced with forward blood flow into branches of the aortic arch allowing for wireless catheterization and at least partial occlusion of the right carotid artery and the left carotid artery.

Clause 54 The catheter as set forth above, wherein the shaft has a guidewire channel and a common inflation channel that are the same channel.

Clause 55 The catheter as set forth above, wherein the guidewire channel and the common inflation channel opens at a distal end of the tip.

Clause 56 The catheter as set forth above, wherein the guidewire channel and the common inflation channel is at the tip is, occluded by the guidewire while the guidewire channel and the common inflation channel remains, in a fluid connection with the distal occluding balloon, wherein an occluding guidewire comprises a distal segment which has an outer diameter that is equal or closely approximated to an inner diameter of the guidewire channel and the common inflation channel at the distal tip of the catheter and is smaller than the inner diameter of the guidewire channel and the common inflation channel proximal to the tip.

Clause 57 The catheter as set forth above, wherein the guidewire channel and the common inflation channel is closed at an end of the tip, wherein an inner diameter of the guidewire channel and the common inflation channel is larger than an outer diameter of the guidewire and wherein inflation of the proximal and distal occluding balloons is possible while the guidewire is inserted and within the guidewire channel and the common inflation channel.

Clause 58 The catheter as set forth above, wherein the guidewire channel and the common inflation channel at the tip has an occluding mechanism that is a distal catheter guidewire channel valve made out of compliant protuberations of a material of an the shaft that allow for a passage of a guidewire while congruently surrounding the surface of the guidewire creating a seal and wherein the distal catheter guidwire channel valve re-close on itself after the guidewire is withdrawn.

Clause 59 The catheter as set forth above, wherein the shaft has a wire channel that starts distal to the proximal occluding balloon and ends at the tip of the, wherein there is no wire channel at the proximal occluding balloon and proximal to the proximal occluding balloon.

Clause 60 The catheter as set forth above, wherein the shaft has a wire channel that starts distal to the proximal occluding balloon (40-60 millimeters from the tip) and proximal to the distal occluding balloon and has a monorail configuration and exits through the distal end of the tip.

Clause 61 The catheter as set forth above, wherein the shaft has balloon inflation holes for inflation of the distal and proximal occluding balloons, wherein the number and orientation of the balloon inflation holes is designed to promote flexion of the shaft toward the curvature Alpha and curvature Gamma, curvature Beta, wherein the majority of the inflation holes face inner curvature of the shaft and the minority of inflation holes or no inflation holes face the outer curve of the shaft, and wherein the balloon inflation holes are of a smaller size than an inner inflation channel of the shaft.

Clause 62 The catheter as set forth above, wherein at least one of the proximal and distal occluding balloons induces bending of the shaft at the level of the balloons upon inflation of the balloons, wherein the bending is effected by an asymmetrical position of the proximal and/or distal occluding balloon relative to the shaft such that a central proximal and/or distal occluding balloon axis is not coaxial with a central axis of the shaft.

Clause 63 The catheter as set forth above, wherein at least one of the proximal and distal occluding balloons induces bending of the shaft at the level of the balloons upon inflation of the balloons, wherein compliance of the proximal and/or distal occluding balloons material on one side of the occluding balloon(s) in relation to a central axis of the shaft is different from compliance of the balloon(s) material on the opposite side in relation to the central axis of shaft, wherein upon inflation the degree of stretching of the balloon(s) material on the side with lower compliance is less than the degree of stretching of the balloon(s) material on the side with higher compliance to induce bending of the shaft within and adjacent to the balloon(s), wherein different degrees of balloon(s) inflation induces a different degree of the bending of the shaft.

Clause 64 The catheter as set forth above, wherein the shaft has a guidewire channel that is in fluid communication with the proximal occluding balloon and the distal occluding balloon, wherein the guidewire channel does not have a distal opening, and wherein the tip of the catheter has no opening, and wherein the inflation of the proximal and distal occluding balloon is possible with or without insertion of a guidewire due to differences in an inner diameter of the guidewire channel and an outer diameter of the guidewire allowing for inflation fluid to pass through the guidewire channel when the guidewire is inserted progressing through residual space between the guidewire and the inner walls of the guidewire channel.

Clause 65 The catheter as set forth above, wherein the shaft has a guidewire channel that is in fluid communication with the proximal occluding balloon and the distal occluding balloon, wherein the guidewire channel has a diameter that is approximate or equal to an outer diameter of a guidewire at the tip and wherein the guidewire channel has a diameter that is larger than the outer diameter of the guidewire at the distal occluding balloon such that inflation fluid is capable of flowing past the guidewire and into the distal occluding balloon to effect inflation of the distal occluding balloon, and wherein the guidewire at the tip blocks inflation fluid from flowing out of the tip when the guidwire is present therein.

Clause 66 The catheter as set forth above, wherein the proximal occluding balloon is larger than the distal occluding balloon, wherein a number of inflation-deflation openings and their total area is proportionally less than the inflation-deflation openings of the distal occluding balloon, wherein the rate of expansion/deflation of the larger proximal occluding balloon is adjusted via the smaller distal occluding balloon to achieve a synchronous expansion and deflation of both occluding balloons.

Clause 67 The catheter as set forth above, wherein in order to achieve a desired degree of flexion of the shaft to achieve a curvature Alpha (angle α) between 160 and 220 degrees the proximal occluding balloon is attached to the shaft in such a way that its expansion leads to further flexion of the shaft, wherein the degree of such flexion is achieved by the degree of proximal occluding balloon expansion;

wherein the flexion is further achieved by a mechanism selected from the group consisting of: stretching, axial rotation, coaxiality, and heterogeneous compliance in which compliance of the proximal occluding balloon surface facing inside of the angulation of the shaft, is lower than the rest of the proximal occluding balloon;

wherein stretching of the proximal occluding balloon upon inflation is between 5 and 55% of a non-stretched length of the proximal occluding balloon, and inflation of the proximal occluding balloon effects a 5-65 degree twisting of the balloon at 0-30 degrees along a longitudinal length of the proximal occluding balloon.

Clause 68 The catheter as set forth above, wherein the shaft of the catheter flexes during expansion of the distal and proximal occluding balloons due to asymmetrical ability of the proximal and, distal occluding balloon material to stretch with the area of the proximal and distal occluding balloon on a side of required flexion being less compliant than the opposite side wherein less or more compliant areas of the proximal and distal occluding balloons are incorporated into the surface of the proximal and distal occluding balloons as a straight line and/or a curved line and/or a spiral at throughout 20%-150% of the proximal and distal occluding balloon length and circumference.

Clause 69 The catheter as set forth above, wherein a desired degree of shaft flexion is achieved through expansion of the proximal occluding balloon in which the proximal occluding balloon extends along a length of the shaft upon inflation of the proximal occluding balloon along the segment by an amount from 5-55% from a deflated state of the proximal occluding balloon.

Clause 70 The catheter as set forth above, wherein a desired degree of shaft flexion is achieved by extending of the distal occluding balloon along the shaft upon inflation of the distal occluding balloon.

Clause 71 The catheter as set forth above, wherein the shaft flexes by mounting the proximal and distal occluding balloons in eccentric and non-coaxial fashions, wherein a larger area of the proximal and distal occluding balloons face the side of the shaft to which curvature is imparted upon inflation.

Clause 72 The catheter as set forth above, wherein at least one of the occluding balloons is stretched along the shaft leading to a 5-55% stretching of the occluding balloon material with a resultant decreased outer diameter of a deflated occluding balloon, thus decreasing the occluding balloon outer profile and improving ability to be passed through narrower space.

Clause 73 The catheter as set forth above, wherein at least one of the proximal and distal occluding balloons is at an eccentric position relative to the shaft such that an occluding balloon neck is located with 25-75% of the occluding balloon circumference, volume, surface located offset from a central axis of the shaft to promote desired flexion and/or extension and/or torqueing of the shaft to facilitate a process of catheterization of a target vessel with or without a guidewire.

Clause 74 The catheter as set forth above, further comprising a coil embedded into a distal end of the shaft to maintain the curvature of the tip at the required shape, wherein the shape of curvature has a curvature angle gamma that is 180+/−30 degrees and a radius of 6.0+/−3.4 mm to facilitate catheterization of a branching vessel.

Clause 75 The catheter as set forth above, wherein the proximal occluding balloon has a proximal portion and a distal portion wherein the distal portion is wider than the proximal portion when the proximal occluding balloon is inflated without engagement with the patient, wherein a center portion of the proximal occluding balloon is more narrow than the distal portion of the proximal occluding balloon when the proximal occluding balloon is inflated without engagement with the patient;

wherein the distal occluding balloon has, a proximal portion and a distal portion wherein the proximal portion of the distal occluding balloon is wider than the distal portion of the distal occluding balloon when the distal occluding balloon is inflated without engagement with the patient, wherein a center portion of the distal occluding balloon is more narrow than the proximal portion of the distal occluding balloon when the distal occluding balloon is inflated without engagement with the patient.

Clause 76 The catheter as set forth above, wherein the proximal occluding balloon when inflated is frustum in shape, wherein the distal occluding balloon when inflated is frustum in shape.

Clause 77 The catheter as set forth above, wherein the proximal occluding balloon has a portion that is more compliant than another portion of the proximal occluding balloon that expands at a different rate than the less compliant portion of the proximal occluding balloon;

wherein the distal occluding balloon has a portion that is more compliant than another portion of the distal occluding balloon that expands at a different rate than the less compliant portion of the distal occluding balloon.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. An occluding catheter for preventing stroke, comprising:

a shaft that has a proximal end and a distal end, wherein the shaft has a common inflation channel and a common inflation port, wherein the shaft has a center;

a proximal occluding balloon carried by the shaft, wherein the proximal occluding balloon is in fluid communication with the common inflation channel;

a distal occluding balloon carried by the shaft and distal to the proximal occluding balloon, wherein the distal occluding balloon is in fluid communication with the common inflation channel;

wherein the shaft has a segment that is between the distal occluding balloon and the proximal occluding balloon;

wherein when inflated the proximal occluding balloon expands to a distance from the center of the shaft that is different than the distance from the center of the shaft to the distal occluding balloon when the distal occluding balloon is inflated;

wherein the proximal occluding balloon and the distal occluding balloon are both inflated via the common inflation channel, wherein the proximal occluding balloon and the distal occluding balloon have a simultaneous rate of expansion;

wherein compliance of the proximal occluding balloon is different than compliance of the distal occluding balloon to account for the simultaneous rate of expansion.

2. An occluding catheter for preventing stroke, comprising:

a shaft that has a proximal end and a distal end, wherein the shaft has a common inflation channel and a common inflation port, wherein the shaft has a center;

a proximal occluding balloon carried by the shaft, wherein the proximal occluding balloon is in fluid communication with the common inflation channel;

a distal occluding balloon carried by the shaft and distal to the proximal occluding balloon, wherein the distal occluding balloon is in fluid communication with the common inflation channel;

wherein the shaft has a segment that is between the distal occluding balloon and the proximal occluding balloon;

wherein when inflated the proximal occluding balloon expands to a distance from the center of the shaft that is different than the distance from the center of the shaft to the distal occluding balloon when the distal occluding balloon is inflated;

wherein the proximal occluding balloon and the distal occluding balloon are both inflated via the common inflation channel, wherein the proximal occluding balloon and the distal occluding balloon have a simultaneous rate of expansion;

wherein a volume of the distal occluding balloon is not the same as a volume of the proximal occluding balloon, and wherein a compliance of the distal occluding balloon is not the same as a compliance of the proximal occluding balloon, wherein such parameters are set in a ratio to keep a diameter of the proximal occluding balloon 1.5-2.5 times larger than a diameter of the distal occluding balloon when both occluding balloons are inflated.

3. An occluding catheter for preventing stroke, comprising:
- a shaft that has a proximal end and a distal end, wherein the shaft has a common inflation channel and a common inflation port, wherein the shaft has a center;
- a proximal occluding balloon carried by the shaft, wherein the proximal occluding balloon is in fluid communication with the common inflation channel;
- a distal occluding balloon carried by the shaft and distal to the proximal occluding balloon, wherein the distal occluding balloon is in fluid communication with the common inflation channel;
- wherein the shaft has a segment that is between the distal occluding balloon and the proximal occluding balloon;
- wherein when inflated the proximal occluding balloon expands to a distance from the center of the shaft that is different than the distance from the center of the shaft to the distal occluding balloon when the distal occluding balloon is inflated;
- wherein the proximal occluding balloon and the distal occluding balloon are both inflated via the common inflation channel, wherein the proximal occluding balloon and the distal occluding balloon have a simultaneous rate of expansion;
- wherein a rate of inflation (measured in cm3 per sec or cc/sec) of the proximal occluding balloon, which is larger than the distal occluding balloon, and the distal occluding balloon are similar, when both occluding balloons are inflated via the common inflation channel, wherein such an equal rate of inflation being achieved by virtue of balancing the parameters determining the degree of surface tension T according to Laplace's Law in the setting of equal Pressures P within the proximal and distal occluding balloons in the setting of the Boyle-Mariotte's Law when P1=P2 while volumes are unequal wherein a ratio of proximal and distal occluding balloon compliances are inversely proportional to the proximal and distal occluding balloon diameters, achieving the goal of synchronous and adequate expansion of the proximal and distal occluding balloons, while inflated via the common inflation channel; and
- wherein a discrepancy in the number, size and the total area of proximal and distal occluding balloon inflation holes is a factor influencing the degree of the proximal and distal occluding balloon inflation and is added to counteract the differences in the proximal and distal occluding balloon volumes, diameters and compliance.

4. An occluding catheter for preventing stroke, comprising:
- a shaft that has a proximal end and a distal end, wherein the shaft has a common inflation channel and a common inflation port, wherein the shaft has a center;
- a proximal occluding balloon carried by the shaft, wherein the proximal occluding balloon is in fluid communication with the common inflation channel;
- a distal occluding balloon carried by the shaft and distal to the proximal occluding balloon, wherein the distal occluding balloon is in fluid communication with the common inflation channel;
- wherein the shaft has a segment that is between the distal occluding balloon and the proximal occluding balloon;
- wherein when inflated the proximal occluding balloon expands to a distance from the center of the shaft that is different than the distance from the center of the shaft to the distal occluding balloon when the distal occluding balloon is inflated;
- wherein the proximal occluding balloon and the distal occluding balloon are both inflated via the common inflation channel, wherein the proximal occluding balloon and the distal occluding balloon have a simultaneous rate of expansion;
- wherein the shaft has a guide wire channel that is the same channel as the common inflation channel and is open at the distal end of the shaft, wherein a diameter of a guidewire at the distal end of the shaft is equal to the an inner diameter of the common inflation channel at the distal end of the shaft, wherein the diameter of the guidewire is smaller than the inner diameter of the common inflation channel in other parts of the shaft allowing for fluid communication between the common inflation port and the proximal and distal occluding balloons when the distal end of the shaft is occluded by the guidewire, wherein the common inflation channel is open at the distal end of the shaft to the exterior if the guidewire is not present in the distal end but is occluded and closed when the guidewire is within the distal end of the shaft so that inflation fluid does not flow out of the open distal end of the common inflation channel.

5. An occluding catheter for preventing stroke, comprising:
- a shaft that has a proximal end and a distal end, wherein the shaft has a center;
- a proximal occluding balloon carried by the shaft;
- a distal occluding balloon carried by the shaft and distal to the proximal occluding balloon;
- wherein the shaft has a segment that is between the distal occluding balloon and the proximal occluding balloon;
- wherein at least one of the proximal and distal occluding balloon is configured such that inflation of the least one of proximal and distal occluding balloon causes bending of the shaft;
- wherein the segment is made of a specific length that is from 1 to 5 centimeters and has a curvature congruent and conforming to an anatomy between an innominate and left carotid artery of a patient wherein the segment has a curvature Alpha at the segment when the proximal and distal occluding balloons are inflated, wherein the shaft has a curvature Beta immediately proximal to the proximal balloon when the proximal and distal balloons are inflated, wherein the shaft has a curvature Gamma distal to the distal occluding balloon when the distal and proximal occluding balloons are both inflated, wherein a curvature Delta is measured between the innominate artery and the left carotid artery.

6. The occluding catheter as set forth in claim 5, wherein the Beta curvature is located 1-10 centimeters proximal to the proximal occluding balloon, wherein the Alpha curvature is directed opposite to the Beta curvature, and the curvature Gamma is located distal to the distal occluding balloon, and the radius of the curvature Alpha is between 4 and 12 millimeters and the radius of the Beta curvature is between 6 and 12 centimeters, and wherein the shaft is configured to exhibit fixation points that are points of contact and radial force application between the occluding catheter and vessel walls between the curvature Alpha and the right or left subclavian artery, and between the curvature beta and the innominate artery.

7. The occluding catheter as set forth in claim 5, wherein the shaft has a common inflation channel in fluid communication with both the proximal and distal occluding balloons, wherein the shaft has balloon inflation holes for inflation of the distal and proximal occluding balloons, wherein the number and orientation of the balloon inflation holes is designed to promote flexion of the shaft toward the curvature Alpha, curvature Gamma, and curvature Beta;

wherein the majority of the inflation holes face inner curvature of the shaft and the minority of inflation holes or no inflation holes face the outer curve of the shaft, and wherein the balloon inflation holes have a smaller cross-section than a cross-section of the common inflation channel.

8. An occluding catheter for preventing stroke, comprising:

a shaft that has a proximal end and a distal end, wherein the shaft has a center;
  a proximal occluding balloon carried by the shaft;
  a distal occluding balloon carried by the shaft and distal to the proximal occluding balloon;
  wherein the shaft has a segment that is between the distal occluding balloon and the proximal occluding balloon;
  wherein at least one of the proximal and distal occluding balloon is configured such that inflation of the least one of proximal and distal occluding balloon causes bending of the shaft;
  wherein both the proximal and the distal occluding balloons induce bending of the shaft at the level of the proximal and distal occluding balloons upon inflation of the proximal and distal occluding balloons, wherein compliance of the proximal and distal occluding balloons material on one side of the proximal and distal occluding balloons in relation to a central axis of the shaft is different from compliance of the proximal and distal occluding balloons material on the opposite side in relation to the central axis of shaft, wherein upon inflation the degree of stretching of the proximal and distal occluding balloons material on the side with lower compliance is less than, the degree of stretching of the proximal and distal occluding balloons material on the side with higher compliance to induce bending of the shaft within and adjacent to the proximal and distal occluding balloons, wherein different degrees of proximal and distal occluding balloons inflation induces a different degree of the bending of the shaft.

9. An occluding catheter for preventing stroke, comprising:

a shaft that has a proximal end and a distal end, wherein the shaft has a center;
  a proximal occluding balloon carried by the shaft;
  a distal occluding balloon carried by the shaft and distal to the proximal occluding balloon;
  wherein the shaft has a segment that is between the distal occluding balloon and the proximal occluding balloon;
  wherein at least one of the proximal and distal occluding balloon is configured such that inflation of the least one of proximal and distal occluding balloon causes bending of the shaft;
  wherein the segment has a curvature Alpha at the segment when the proximal and distal occluding balloons are inflated that is from 160 to 220 degrees, wherein the proximal occluding balloon is attached to the shaft in such a way that expansion of the proximal occluding balloon leads to flexion of the shaft such that the degree of such flexion is achieved by the degree of proximal occluding balloon expansion;
  wherein upon inflation of the proximal occluding balloon the proximal occluding balloon effects a 5-65 degree twisting of the balloon relative to a central axis of the shaft such that the twisting is imparted to the shaft to bend the shaft.

10. An occluding catheter for preventing stroke, comprising:

a shaft that has a proximal end and a distal end, wherein the shaft has a center;
  a proximal occluding balloon carried by the shaft;
  a distal occluding balloon carried by the shaft and distal to the proximal occluding balloon;
  wherein the shaft has a segment that is between the distal occluding balloon and the proximal occluding balloon;
  wherein at least one of the proximal and distal occluding balloon is configured such that inflation of the least one of proximal and distal occluding balloon causes bending of the shaft;
  wherein both the proximal and distal occluding balloons effect bending of the shaft, wherein differences in compliance of the proximal and distal occluding balloons are present in which the proximal and distal occluding balloons stretch asymmetrically during expansion, wherein the sides of the proximal and distal occluding balloons differ in compliance to effect the bending of the shaft;
  wherein greater areas of compliance are incorporated into the surface of the proximal and distal occluding balloons as straight strips and/or curved strips and/or spiral strips to effect the desired bending of the shaft upon inflation of the proximal and distal occluding balloons, wherein the areas of more compliant balloon material expand at a different rate than the areas of the less compliant balloon material upon expansion.

11. An occluding catheter for preventing stroke, comprising:

a shaft that has a proximal end and a distal end, wherein the shaft has a center;
  a proximal occluding balloon carried by the shaft;
  a distal occluding balloon carried by the shaft and distal to the proximal occluding balloon;
  wherein the shaft has a segment that is between the distal occluding balloon and the proximal occluding balloon;
  wherein at least one of the proximal and distal occluding balloon is configured such that inflation of the least one of proximal and distal occluding balloon causes bending of the shaft;
  wherein the shaft flexes by mounting the proximal and distal occluding balloons in eccentric and non-coaxial fashions, wherein a larger area of the proximal and distal occluding balloons face the side of the shaft to which curvature is imparted upon inflation than the side of the shaft opposite;
  wherein the eccentric and non-coaxial offset is arranged such that necks of the proximal and distal occluding balloons are offset from a central axis of the shaft so that one side of the proximal occluding balloon has from 25% to 75% more volume of inflation fluid than the other side of the proximal occluding balloon, and wherein one side of the distal occluding balloon has from 25% to 75% more volume of inflation fluid than the other side of the distal occluding balloon.

12. An occluding catheter for preventing stroke, comprising:

a shaft that has a proximal end and a distal end, wherein the shaft has a center;
  a proximal occluding balloon carried by the shaft;
  a distal occluding balloon carried by the shaft and distal to the proximal occluding balloon;

wherein the shaft has a segment that is between the distal occluding balloon and the proximal occluding balloon;

wherein the proximal occluding balloon has a proximal portion and a distal portion that has a different width than the proximal portion when the proximal occluding balloon is inflated without engagement with the patient, wherein a center portion of the proximal occluding balloon is more narrow than one of the proximal and distal portions of the proximal occluding balloon when the proximal occluding balloon is inflated without engagement with the patient;

wherein the distal occluding balloon has a proximal portion and a distal portion that has a different width than the proximal portion of the distal occluding balloon when the distal occluding balloon is inflated without engagement with the patient, wherein a center portion of the distal occluding balloon is more narrow than one of the proximal and distal portions of the distal occluding balloon when the distal occluding balloon is inflated without engagement with the patient;

wherein the distal portion of the proximal occluding balloon is wider than the proximal portion of the distal occluding balloon when the proximal occluding balloon is inflated without engagement with the patient, and wherein the center portion of the proximal occluding balloon is more narrow than the distal portion of the proximal occluding balloon when the proximal occluding balloon is inflated without engagement with the patient;

wherein the proximal portion of the distal occluding balloon is wider than the distal portion of the distal occluding balloon when the distal occluding balloon is inflated without engagement with the patient, and wherein the center portion of the distal occluding balloon is more narrow than the proximal portion of the distal occluding balloon when the distal occluding balloon is inflated without engagement with the patient.

13. An occluding catheter for preventing stroke, comprising:

a shaft that has a proximal end and a distal end, wherein the shaft has a center;

a proximal occluding balloon carried by the shaft;

a distal occluding balloon carried by the shaft and distal to the proximal occluding balloon;

wherein the shaft has a segment that is between the distal occluding balloon and the proximal occluding balloon;

wherein the proximal occluding balloon has a proximal portion and a distal portion that has a different width than the proximal portion when the proximal occluding balloon is inflated without engagement with the patient, wherein a center portion of the proximal occluding balloon is more narrow than one of the proximal and distal portions of the proximal occluding balloon when the proximal occluding balloon is inflated without engagement with the patient;

wherein the distal occluding balloon has a proximal portion and a distal portion that has a different width than the proximal portion of the distal occluding balloon when the distal occluding balloon is inflated without engagement with the patient, wherein a center portion of the distal occluding balloon is more narrow than one of the proximal and distal portions of the distal occluding balloon when the distal occluding balloon is inflated without engagement with the patient;

wherein the proximal occluding balloon when inflated without engagement with the patient is frustum in shape, wherein the distal occluding balloon when inflated without engagement with the patient, is frustum in shape.

14. An occluding catheter for preventing stroke, comprising:

a shaft that has a proximal end and a distal end, wherein the shaft has a center, wherein the shaft has a guidewire channel configured for having a guidewire disposed therein;

a proximal occluding balloon carried by the shaft;

a distal occluding balloon carried by the shaft and distal to the proximal occluding balloon;

wherein the shaft has a segment that is between the distal occluding balloon and the proximal occluding balloon;

an occluding mechanism located at the distal end of the shaft that closes the guidewire channel, wherein force applied to the occluding mechanism causes opening of the occluding mechanism;

wherein the guidewire channel starts distal to the proximal occluding balloon at a location from 40-60 millimeters from a distal terminal end of the shaft, and proximal to the distal occluding balloon and exits through the distal terminal end of the shaft.

* * * * *